(12) United States Patent
Karin et al.

(10) Patent No.: US 10,034,462 B2
(45) Date of Patent: Jul. 31, 2018

(54) ANIMAL MODEL OF NASH-INDUCED HEPATOCELLULAR CARCINOMA AND METHODS FOR DEVELOPING SPECIFIC THERAPEUTICS

(71) Applicant: THE REGENTS OF THE UNIVERSITY OF CALIFORNIA, Oakland, CA (US)

(72) Inventors: Michael Karin, La Jolla, CA (US); Atsushi Umemura, Kyoto (JP); Hayato Nakagawa, Tokyo (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/178,935

(22) Filed: Jun. 10, 2016

(65) Prior Publication Data
US 2016/0360735 A1    Dec. 15, 2016

Related U.S. Application Data

(60) Provisional application No. 62/174,878, filed on Jun. 12, 2015.

(51) Int. Cl.
| | | |
|---|---|---|
| A01K 67/027 | (2006.01) | |
| C12Q 1/68 | (2018.01) | |
| G01N 33/50 | (2006.01) | |

(52) U.S. Cl.
CPC ...... *A01K 67/0271* (2013.01); *G01N 33/5011* (2013.01); *G01N 33/5088* (2013.01); *A01K 2207/12* (2013.01); *A01K 2207/25* (2013.01); *A01K 2227/105* (2013.01); *A01K 2267/0331* (2013.01)

(58) Field of Classification Search
None
See application file for complete search history.

(56) References Cited

PUBLICATIONS

He, et al. (2015) "Mouse models of liver cancer: Progress and recommendations", Oncotarget, 6(27): 23306-22.*
Anderson, et al. "Mitochondrial H2O2 Emission and Cellular Redox State Link Excess Fat Intake to Insulin Resistance in Both Rodents and Humans." J Clin Invest, 2009,119:573-581.
Brunt, E.M. "Nonalcoholic Steatohepatitis:Definition and Pathology." Semin Liver Dis, 2001, 21:3-16.
Caldwell, et al. "Hepatocellular Balooning in NASH." J Hepatol, 2010, 53:719-723.
Calle and Thun, "Obesity and Mortality." N Engl J Med, 2005, 353:2197-2199.
Chandler, et al. "Vector Design Influences Hepatic Genotoxicity After Adeno-Associated Virus Gene Therapy." J Olin Invest, 2015, 125:870-880.
Chen, et al. "Metabolic Factors and Risk of Hepatocellular Carcinoma by Chronic Hepatitis B/C Infection: A Follow-Up Study in Taiwan." Gastroenterology, 2008, 135:111-121.
Cohen and Hobbs, "Human Fatty Liver Disease: Old Questions and New Insights." Science, 2011, 332:1519-1523.
Day and James, "Steatohepatitis: A Tale of Two 'Hits'?" Gastroenterology, 1998, 114:842-845.
Denk, et al. "Are the Mallory Bodies and Intracellular Hyaline Bodies in Neoplastic and Non-Neoplastic Hepatocytes Related?" J Pathol, 2006, 208:653-661.
Dezwaan, et al. "The Stress-Regulated Transcription Factor CHOP Promotes Hepatic Inflammatory Gene Expression, Fibrosis, and Oncogenesis." PLoS Genet, 2013, 9:e1003937.
El-Serag, B.H. "Hepatocellular Carcinoma." N Engl J Med, 2011, 365:1118-1127.
Farrell, et al. "NASH is an Inflammatory Disorder: Pathogenic, Prognostic and Therapeutic Implications." Gut and Liver, 2012, 6:149-171.
Goldstein, et al. "Protein Sensors for Membrane Sterols." Cell, 2006, 124:35-46.
Haybaeck, et al. "A Lymphotoxin-Driven Pathway to Hepatocellular Carcinoma." Cancer Cell, 2009, 16:295-308.
Hayes and McMahon, "The Double-Edged Sword of Nrf2: Subversion of Redox Homeostasis During the Evolution of Cancer." Mol. Cell, 2006, 21:732-734.
Hayes and McMahon, "NRF2 and KEAP1 Mutations: Permanent Activations of an Adaptive Response in Cancer." Trends Biochem. 2009, Sci 34:176-188.
He et al. "Identification of Liver Cancer Progenitors Whose Malignant Progression Depends on Autocrine IL-6 Signaling." Cell, 2013, 155:384-396.
Holzer, et al. "Saturated Fatty Acids Induce c-Src Clustering within Membrane Subdomains, Leading to JNK Activation." Cell, 2011, 147:173-184.
Hotamisligil, G.S. "Endoplasmic Reticulum Stress and the Inflammatory Basis of Metabolic Disease." Cell, 2010, 140:900-917.
Ichimura, et al. "Phosphorylation of p62 Activates the Keap1-Nrf2 pathway During Selective Autophagy." Mol. Cell, 2013,51:618-631.
Inami, et al. "Persistent Activation of Nrf2 through p62 in Hepatocellular Carcinoma Cells." J Cell Biol, 2011, 193:275-284.
Jain, et al. "p62/SQSTM1 is a Target Gene for Transcription Factor NRF2 and Creates a Positive Feedback Loop by Inducing Antioxidant Response Element-Driven Gene Transcription." J Biol Chem, 2010, 285:22576-22591.
Kammoun, et al. "GRP78 Expression Inhibits Insulin and ER Stress-Induced Srebp-1c Activation and Reduces Hepatic Steatosis in Mice." J Clin Invest, 2009, 119:1201-1215.
Kaposi-Novak, et al. "Central Role of c-Myc During Malignant Conversion in Human Hepatocarcinogenesis." Cancer Res, 2009, 69:2775-2782.
Komatsu, et al. "Homeostatic Levels of p62 Control Cytoplasmic Inclusion Body Formation in Autophagy-Deficient Mice." Cell, 2007, 131:1149-1163.

(Continued)

*Primary Examiner* — Robert M Kelly
(74) *Attorney, Agent, or Firm* — Wagenknecht IP Law Group PC

(57) ABSTRACT

The invention provides a non-human animal model for non-alcoholic steatohepatitis (NASH)-induced heptocellular carcinoma, methods of screening for agents for treating heptocellular carcinoma, methods of screening for targets useful in suppressing NASH progression to heptocellular carcinoma, methods of treating heptocellular carcinoma, and compositions for treating the same.

4 Claims, 45 Drawing Sheets

(56) References Cited

PUBLICATIONS

Komatusu, et al. "p62/SQSTM1/A170: Physiology and Pathology." Pharmacol. Res, 2012, 66:457-462.

Lee, et al. "Regulation of Hepatic Lipogenesis by the Transcription Factor XBP1." Science, 2008, 320:1492-1496.

Lee, et al. "Maintenance of Metabolic Homeostasis by Sestrini2 and Sestrin3." Cell Metab, 2012, 16:311-321.

Li, et al. "SQSTM1 is a Pathogenic Target of 5q Copy Number Gains in Kidney Cancer." Cancer Cell, 2013, 24:738-750.

Maeda, et al. "IKKbeta Couples Hepatocyte Death to Cytokine-Driven Compensatory Proliferation That Promotes Chemical Hepatocarcinogenesis." Cell, 2005, 121:977-990.

Malhi and Kaufman, "Endoplasmic Reticulum Stress in Liver Disease." J Hepatol, 2011, 54:795-809.

Menon, et al."Chronic Activation of mTOR Complex 1 is Sufficient to Cause Hepatocellular Carcinoma in Mice." Sci Signal, 2012, 5:ra24.

Mori, et al. "Critical Role for Hypothalamic mTOR Activity in Energy Balance." Cell Metab, 2009, 9:362-374.

Muller, et al. "p62 Links Beta-Adrenergic Input to Mitochondrial Function and Thermogenesis." J Clin Invest, 2013, 123:469-478.

Nakagawa, et al. "ER Stress Cooperates with Hypernutrition to Trigger TNF-Dependent Spontaneous HCC Development." Cancer Cell, 2014, 26:331-343.

Ota, et al. "Inhibition of Apolipoprotein B100 Secretion by Lipid-Induced Hepatic Endoplasmic Reticulum Stress in Rodents." J Clin Invest, 2008, 118:316-332.

Ozcan, et al. "Chemical Chaperones Reduce ER Stress and Restore Glucose Homeostasis in a Mouse Model of Type 2 Diabetes." Science, 2006, 313:1137-1140.

Park, et al. "Dietary and Genetic Obesity Promote Liver Inflammation and Tumorigenesis by Enhancing IL-6 and TNF Expression." Cell, 2010, 140:197-208.

Puri, et al. "Activation and Dysregulation of the Unfolded Protein Response in Nonalcoholic Fatty Liver Disease." Gastroenterology, 2008, 134:568-576.

Qiu, et al. "Hepatic Autophagy Mediates Endoplasmic Reticulum Stress-Induced Degradation of Misfolded Apolipoprotein B." Hepatology, 2011, 53:1515-1525.

Rutkowski, et al. "UPR Pathways Combine to Prevent Hepatic Steatosis Cause by ER Stress-Mediated Suppression of Transcriptional Master Regulators." Dev Cell, 2008, 15:829-840.

Sakurai, et al. "Hepatocyte Necrosis Induced by Oxidative Stress and IL-1 Alpha Release Mediate Carcinogen-Induced Compensatory Proliferation and Liver Tumorigenesis." Cancer Cell, 2008, 14:156-165.

Salomao, et al. "The Steatohepatitic Variant of Hepatocellular Carcinoma and its Association with Underlying Steatohepatitis." Hum Pathol, 2012, 43:737-746.

Sandgren et al. "Complete Hepatic Regeneration After Somatic Deletion of an Albumin-Plasminogen Activator Transgene." Cell, 1991, 66:245-256.

Sanz, et al. "The Atypical PKC-Interacting Protein p62 Channels NF-kappaB Activation by the IL-1-TRAF6 Pathway." EMBO J, 2000, 19:1576-1586.

Schramm, et al. "Adalimumab Could Suppress the Activity of Non Alcoholic Steatohepatitis (NASH)." Zeitschrift fur Gastroenterologie, 2008, 46:1369-1371.

So et al. "Silencing of Lipid Metabolism Genes Through IRE1alpha-mediated mRNA Decay Lowers Plasma Lipids in Mice." Cell Metabolism, 2012, 16:487-499.

Soon, et al. "Stress Signaling in the Methionine-Choline-Deficient Model of Murine Fatty Liver Disease." Gastroenterology, 2010, 139:1730-1739,1739 e1731.

Suzuki, et al. "Toward Clinical Application of the Keap1-Nrf2 Pathway." Trends Pharmacol. Sci, 2013, 34:340-346.

Tilg and Moschen, "Evolution of Inflammation in Nonalcoholic Fatty Liver Disease: The Multiple Parallel Hits Hypothesis." Hepatology, 2010, 52:1836-1846.

Toffanin and Llovet, "Obesity, Inflammatory Signaling,and Hepatocellular Carcinoma—an Enlarging Link." Cancer Cell, 2010, 17:115-117.

Umemura, et al. "Liver Damage, Inflammation, and Enhanced Tumorigenesis After Persistent mTORC1 Inhibition." Cell Metab, 2014, 20:133-144.

Valencia, et al. "Metabolic Reprogamming of Stromal Fibroblasts Through p62-mTORC1 Signaling Promotes Inflammation and Tumorigenesis." Cancer Cell, 2014, 26:121-135.

Wang, et al. "Endoplasmic Reticulum Stress Response in Cancer: Molecular Mechanism and Therapeutic Potential." American Journal of Translational Research, 2010, 2:65-74.

Weglarz, et al. "Hepatocyte Transplantation into Diseased Mouse Liver. Kinetics of Parenchymal Repopulation and Identification of the Proliferative Capacity of Tetraploid and Octaploid Hepatocytes." Am J Pathol, 2000, 157:1963-1974.

Xu, et al. "Endoplasmic Reticulum Stress: Cell Life and Death Decisions." J Clin Invest, 2005, 115:2656-2664.

* cited by examiner

| | Histology | Adenoma | HCC |
|---|---|---|---|
| 32 weeks | LFD | 0/5 (0%) | 0/6 (0%) |
| | HFD | 3/6 (50%) | 1/6 (16.6%) |
| | p | 0.045 | 0.29 |
| | Histology | Adenoma | HCC |
|---|---|---|---|
| 40 weeks | LFD | 0/11 (0%) | 0/11 (0%) |
| | HFD | 10/14 (71.4%) | 7/14 (50%) |
| | p | 0.0057 | 0.0093 |
FIG. 9B
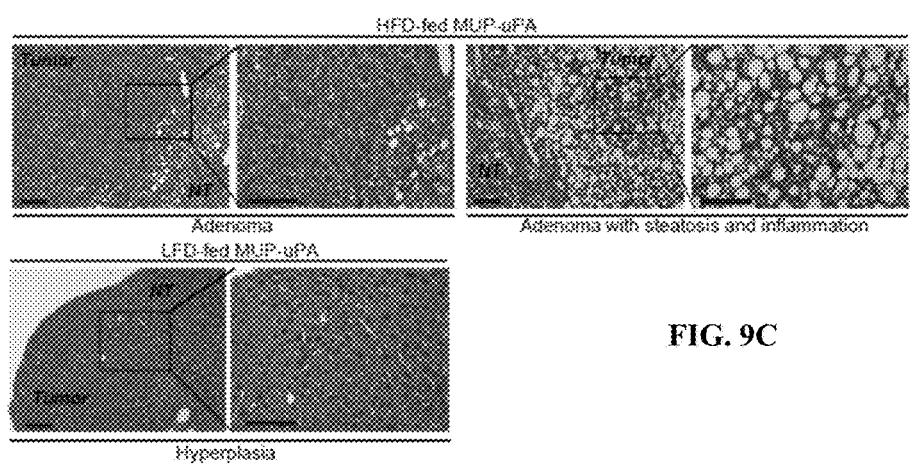
FIG. 9C
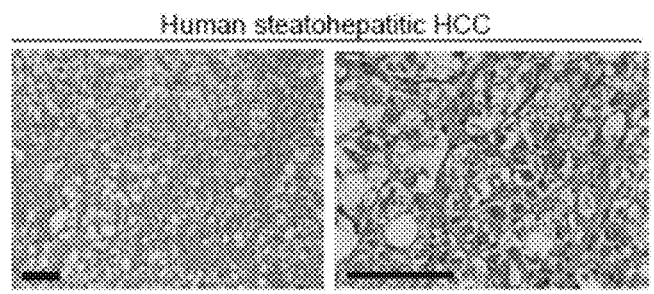
FIG. 9D

ANIMAL MODEL OF NASH-INDUCED HEPATOCELLULAR CARCINOMA AND METHODS FOR DEVELOPING SPECIFIC THERAPEUTICS

CROSS REFERENCE TO RELATED APPLICATION(S)

This application claims the benefit of priority under 35 U.S.C. § 119(e) of U.S. Ser. No. 62/174,878, filed Jun. 12, 2015, the entire content of which is incorporated herein by reference.

GRANT INFORMATION

This invention was made with government support under Grant Nos. CA118165, CA155120, and ES10337 awarded by The National Institutes of Health. The United States government has certain rights in the invention.

BACKGROUND OF THE INVENTION

Field of the Invention

The invention relates generally to cancer, and more particularly to use of genetically modified non-human animal models for screening for agents for use in treating hepatocellular carcinoma.

Background Information

Hepatocellular carcinoma (HCC) is the fifth most common cancer worldwide and a leading cause of cancer deaths. A common malignancy linked to chronic tissue damage, stress, and environmental carcinogen exposure is HCC, most of which arises as the end stage of chronic liver disease and persistent inflammation, with hepatitis B or C virus (HBV, HCV) infections being the current leading causes. However, obesity and alcohol consumption, which cause hepatic steatosis (non-alcoholic steatohepatitis (NASH) or alcoholic steatohepatitis (ASH), respectively) and fibrosis, are rapidly growing in their importance as HCC risk factors.

Thus, more than 90% of HCC develops in the context of chronic liver disease, with HBV or HCV infections being the main causes. However, 30-40% of Western HCC patients do not exhibit viral infections. Most of these patients are obese with manifestations of the metabolic syndrome, and suffer from NASH, a severe form of non-alcoholic fatty liver disease (NAFLD) (Cohen et al., 2011). Indeed, obesity increases male HCC risk by up to 4.5-fold (Calle et al., 2005) and also increases HCC risk in viral hepatitis (Chen et al., 2008). Because the prevalence of obesity has been increasing worldwide, its association with hepatocarcinogenesis has attracted much attention. A need therefore exists for an animal model to study the development of NASH and its progression to HCC, and to test/evaluate treatments that prevent or ameliorate NASH and attenuate its progression to HCC.

SUMMARY OF THE INVENTION

The present invention relates to genetically modified non-human animals for use as models to identify, test, and evaluate treatments that prevent or ameliorate NASH and attenuate its progression to HCC. The results provided herein suggest that NASH and progression to steatohepatitic HCC may be prevented or ameliorated by anti-TNF drugs.

Accordingly, in one aspect, the invention provides a method of inducing hepatocellular carcinoma (HCC) or HCC-like symptoms in a non-human animal. The method includes transplanting HCC progenitor cells (HcPCs) into a non-human animal and subjecting the mammal to a high fat diet (HFD). In various embodiments, the non-human animal is a transgenic mouse, such as a mouse including the major urinary protein-urokinase plasminogen activator (MUP-uPA) gene.

In another aspect, the invention provides a transgenic non-human animal as a model of NASH progression to HCC. The transgenic non-human animal includes the MUP-uPA gene and has transplanted therein HcPCs, wherein when subjected to HFD, the non-human animal exhibits symptoms of HCC. In various embodiments, the non-human animal is a transgenic mouse. Thus, the invention also provides primary cells and cell lines derived from the transgenic non-human animal of the invention. In various embodiments, the primary cells or cell lines are derived from the liver of the transgenic non-human animal.

In another aspect, the invention provides a method of screening for an agent for its efficacy in treating heptocellular carcinoma (HCC) in a subject. The method includes administering a candidate agent to a non-human transgenic animal having had transplanted therein HCC progenitor cells and subsequently having been subjected to a high fat diet (HFD), measuring a response in expression or activity of TNF, p62, NRF2, mTORC1, or c-Myc to the candidate agent, and comparing the measured expression or activity with that of one or more control animals, wherein reduced or suppressed expression or activity after administration of the candidate agent is indicative of efficacy in treating HCC. In various embodiments, the non-human mammal is a transgenic mouse that may include the major urinary protein-urokinase plasminogen activator (MUP-uPA) gene.

In another aspect, the invention provides a method of suppressing development of hepatocellular carcinoma (HCC) in a subject. The method includes administering to the subject an effective amount of an agent that modulates expression or activity of human TNF or p62, thereby suppressing development of HCC. In one embodiment, expression and/or activity of human TNF or p62 is suppressed. The subject may be a mammal, such as a human, and may have been diagnosed as having or at risk for non-alcoholic steatohepatitis (NASH). The method may further include administering tauroursodeoxycholic acid (TUDCA) in combination with the agent.

BRIEF DESCRIPTION OF THE DRAWINGS

FIG. 1A shows that serum ALT in LFD- or HFD-fed WT and MUP-uPA mice was measured at indicated ages. HFD feeding was initiated at 6 weeks. Data are means±S.D. (n=3-5 per group). *$p<0.05$. FIG. 1B shows the results of H&E staining of liver sections from 5 weeks old mice on LFD and 24 weeks old mice kept on LFD or HFD (scale bar=100 μm). Bottom two panels show infiltration of immune cells in HFD-fed MUP-uPA mouse livers (left, portal area; right, liver parenchyma). FIG. 1C shows the results of Sirius red staining of liver sections described in B (scale bar=100 μm). FIG. 1D shows the results from TUNEL and IHC analyses of Ki67 and K19 in 24 weeks old mice that were kept on LFD or HFD (scale bar=100 μm). Bar graphs show numbers of apoptotic and necrotic cells and Ki67-positive cells per 200× field. Data are means±S.D. (n=5 per group). *$p<0.05$. See also FIGS. 8A-8F.

FIG. 2A shows representative images of livers from 32 and 40 weeks old mice that were kept on LFD or HFD. FIG. 2B shows representative H&E staining of tumor sections from 40 weeks old HFD-fed MUP-uPA mice. Left two panels show trabecular HCC and right two panels show steatohepatitic HCC (scale bar=100 μm). See also FIGS. 9A-9J.

FIGS. 3A and 3B show the results of immunoblot (IB) analysis of ER stress markers in livers of 5 weeks old WT and MUP-uPA mice (FIG. 3A) and 16 week old WT and MUP-uPA mice kept on LFD or HFD (FIG. 3B). FIG. 3C shows the results of IHC analysis of CHOP in livers of 5 weeks old mice on LFD and 16 week old mice kept on LFD or HFD (scale bar=100 μm). FIG. 3D shows the results of Oil Red O staining of mouse livers described in C (scale bar=100 μm). (FIG. 3E) TG and cholesterol content of mouse livers described in C. FIG. 3F shows the results from IB analysis of unprocessed precursor SREBP1 (P-SREBP1) in whole liver extract and mature SREBP1 (M-SREBP1) in liver nuclei of mice described in A (upper panels) and B (lower panels). FIG. 3G shows the results from real time PCR analysis of liver FAS mRNA. FIG. 3H shows the results from Hepatic FA composition in 16 week old mice kept on LFD or HFD, analyzed by gas-chromatography. $*p<0.05$, compared with LFD-fed WT mice. $\#p<0.05$, compared with HFD-fed WT mice. FIG. 3I shows accumulation of reactive oxygen species (ROS) in 16 week old mice that were kept on LFD or HFD. Decreased GSH:GSSG ratio indicates elevated oxidative stress. All bar graphs represent means±S.D. (n=3 per group). $*p<0.05$. See also FIGS. 10A-10J.

FIG. 4A shows that primary hepatocytes from WT and MUP-uPA mice were incubated with 300 μM palmitic acid (PA) for 24 hr with or without 500 μM tauroursodeoxycholic acid (TUDCA) or 1 mM 4-phenylbutyric acid (4-PBA). Cell viability was assessed using Cell Counting Kit-8 assay. Data are means±S.D. of triplicate wells. $*p<0.05$. FIG. 4B shows that primary hepatocytes from WT and MUP-uPA mice were incubated with 200 μM PA with or without 4-PBA as above. CHOP expression, SREBP1 maturation, and JNK phosphorylation were assessed by IB. FIGS. 4C-4D show the effect of GRP78 overexpression. MUP-uPA hepatocytes were infected with adenoviruses encoding LacZ or GRP78 and then incubated with PA. SREBP1 maturation (FIG. 4C) and cell viability (FIG. 4D) were assessed as above. FIG. 4E shows that hepatocytes from WT and MUP-uPA mice were incubated with 300 μM PA for 24 hr with or without 10 μM D-JNKi (JNK inhibitor), and cell viability was assessed. Data are means±S.D. of triplicate wells. $*p<0.05$. FIGS. 4F-4I show the effect of TUDCA on NASH in HFD-fed MUP-uPA mice. 16 week old HFD-fed MUP-uPA mice were i.p. injected with TUDCA (250 mg/kg) or vehicle, and after 4 weeks of daily treatment, liver histology (scale bar=100 μm) (FIG. 4F), serum ALT (FIG. 4G), liver TG (FIG. 4H) and liver cholesterol (FIG. 4I) were evaluated. Bar graphs are means±S.D. (n=5 per group). $*p<0.05$. See also FIGS. 11A-11M.

FIG. 5A shows relative inflammatory cytokine mRNA in livers of 24 weeks old mice kept on LFD or HFD determined by real-time Q-PCR. Data are means±S.D. (LFD-fed WT, n=3; others, n=5 per group). $*p<0.05$. FIG. 5B shows that TNF protein in livers from A was measured by ELISA. Means±S.D. $*p<0.05$. FIG. 5C shows the results from Double IF analysis of F4/80 (green) and TNF (red) of liver sections from A (scale bar=100 μm). Nuclei were labeled with DAPI (blue). FIGS. 5D-5H show the effect of TNFR1 ablation on NASH and tumorigenesis in HFD-fed MUP-uPA mice. MUP-uPA and Tnfr1$^{-/-}$/MUP-uPA mice were fed HFD from 6 to 40 weeks of age. Representative images of livers (FIG. 5D), tumor numbers and maximal sizes (FIG. 5E), H&E staining of non-tumor areas (scale bar=100 μm) (FIG. 5F), and serum ALT (FIG. 5G) are shown. Bar graphs represent means±S.E.M. (MUP-uPA, n=14; Tnfr1$^{-/-}$/MUP-uPA, n=11). $*p<0.05$. FIG. 5H shows triglycerides (TG) and cholesterol content in non-tumor tissue of HFD-fed MUP-uPA and Tnfr1$^{-/-}$/MUP-uPA mouse livers. Bar graphs represent means±S.D. (n=7 per group). $*p<0.05$. FIG. 5I shows the results from IB analyses showing effects of TNFR1 ablation on SREBP1 maturation and JNK phosphorylation in non-tumor tissue of HFD-fed MUP-uPA mice. See also FIGS. 12A-12F.

FIG. 6A shows HCC progenitor cell (HcPC) isolation from diethylnitrosamine (DEN)-treated WT and Tnfr1$^{-/-}$ mice and transplantation into MUP-uPA mice. HcPC-transplanted MUP-uPA mice were divided into two groups that were fed with either LFD or HFD, and 5 months later tumorigenesis was assessed. FIG. 6B shows representative images of non-transplanted and HcPC-transplanted MUP-uPA mouse livers. FIG. 6C shows tumor numbers and maximal sizes. Results are means±S.E.M. (n=10-11 per group). $*p<0.05$. FIG. 6D shows Ki67 IHC and TUNEL staining of tumor areas in livers from C (scale bar=100 μm). Bars represent numbers of apoptotic and necrotic cells and Ki67-positive cells per field. Results are means±S.D. (n=6 per group). $*p<0.05$. FIG. 6E shows tumor tissues from WT or Tnfr1$^{-/-}$ HcPC-transplanted MUP-uPA mice kept on LFD or HFD were IB analyzed for phosphorylation of ERK, STAT3, JNK, and S6, and expression of cyclin D1. Data were quantified using Image J software and are presented as means±S.D. (n=5-6 per group). $*p<0.05$. FIG. 6F shows the results from activation of NF-κB analyzed by p65/RelA IHC in tumor tissues from MUP-uPA transplanted with WT or Tnfr1$^{-/-}$ HcPC and kept on LFD or HFD (scale bar=25 μm). Bars show numbers of nuclear p65 positive cancer cells per 200× field. Data are means±S.D. (n=6 per group). $*p<0.05$. FIG. 6G shows the effect of IKKβ ablation on HFD-stimulated HcPC progression. HcPCs isolated from DEN-injected liver-specific Ikkβ$^{\Delta hep}$ were transplanted into MUP-uPA mice as in A and the HcPC-transplanted mice were kept on LFD or HFD. 5 months later, tumor multiplicity and maximal sizes were determined. Data are means±S.E.M. (n=10 per group). See also FIGS. 13A-13J.

FIG. 7A shows the results from H&E analysis of tumors from WT or Tnfr1$^{-/-}$ HcPC in MUP-uPA mice that were kept on LFD or HFD (scale bar=100 μm). FIG. 7B shows the results from real time PCR determination of immune cell marker mRNAs in tumor tissues. Data are means±S.D. (n=5 per group). $*p<0.05$. FIG. 7C shows the results from IHC analysis of F4/80- and B220-positive cells in tumor tissues from A (scale bar=100 μm). FIG. 7D shows the results from IF analysis of CCL7 expression in tumor tissues (scale bar=25 μm). See also FIG. 14.

FIG. 8A shows body weights of LFD- or HFD-fed WT and MUP-uPA mice. HFD was started at 6 weeks of age. Data are means±S.D. (n=6-8 per group). *p<0.05. FIG. 8B shows the results from glucose tolerance tests of 24 weeks old WT and MUP-uPA mice that were kept on LFD or HFD. Blood glucose was measured at the indicated time points after i.p. injection of 0.8 g/kg (right graph) or 2.0 g/kg (left graph) glucose. (n=4-5 per group). FIG. 8C shows that expression of the uPA transgene was examined by real-time PCR. Results are presented as means±S.D. (n=3 per group). FIG. 8D shows a comparison of liver histology between HFD-fed MUP-uPA mouse (24 weeks old) and human NASH by H&E and Sirius red staining (scale bar=100 µm). Bottom panel shows high magnification image of Sirius red staining of HFD-fed MUP-uPA mouse liver (scale bar=100 µm). Sirius red positive areas in livers from 24 weeks old WT and MUP-uPA mice that were kept on LFD or HFD were quantified with Image J software and shown as bar graphs. Data are means±S.D. (n=4 per group). *p<0.05. (FIG. 8E) Relative mRNA amounts of type 1 collagen a1 were examined by real-time Q-PCR. Data are presented as means±S.D. (LFD-fed WT, n=3; others, n=5 per group). *p<0.05. (F) Immunoblot evaluation of cyclin D1 in livers of 24 weeks old mice kept on LFD or HFD.

FIGS. 9A-9J are pictorial and graphical diagrams showing characteristics of liver tumors in HFD-fed MUP-uPA mice. FIG. 9A shows the average numbers of liver tumors in LFD- or HFD-fed MUP-uPA mice at 32 and 40 weeks of age. FIG. 9B shows the frequencies of liver adenoma and HCC in LFD- or HFD-fed MUP-uPA mice at 32 and 40 weeks of age. FIG. 9C shows representative H&E staining of tumor sections from 40 weeks old LFD- or HFD-fed MUP-uPA mice. Upper four panels show adenomas from HFD-fed MUP-uPA mice and lower two panels show hyperplastic nodule from LFD-fed MUP-uPA mice (scale bar=100 µm). FIG. 9D shows representative images of H&E stained human steatohepatitic HCC (scale bar=100 µm). FIG. 9E shows the results from IHC analysis of the indicated antigens in non-tumor (NT) and tumor areas of 40 weeks old HFD-fed MUP-uPA livers (scale bar=100 µm). FIG. 9F shows the results of IHC of YAP and EpCAM in tumor and non-tumor (NT) areas of HFD-fed MUP-uPA mouse livers (scale bar=100 µm). FIG. 9G shows relative CD44 and Myc mRNAs in tumor and NT areas of HFD-fed MUP-uPA mouse livers. Data are means±S.D. (NT, n=3; Tumor, n=5). *p<0.05. FIG. 9H shows the results from IB analysis of the indicated proteins in liver tumors and non-tumor liver tissue (NT) from 40 weeks old HFD-fed MUP-uPA mice. FIG. 9I shows the results of IHC of Ki67 and AFP in hyperplastic lesion from 40 weeks old LFD-fed MUP-uPA livers (scale bar=100 µm). FIG. 9J shows the results of IHC of p62 and YAP in liver premalignant foci of 24 weeks old HFD-fed MUP-uPA mice (scale bar=100 µm).

FIG. 10A shows relative mRNA amounts of ER stress markers in livers of 5 weeks old WT and MUP-uPA mice and 16 week old WT and MUP-uPA mice that were kept on LFD or HFD. FIG. 10B shows relative mRNA amounts of downstream targets for ER stress signaling in livers of 16 week old WT and MUP-uPA mice kept on LFD or HFD and TRAIL mRNA at 24 weeks. FIG. 10C shows electron micrographs showing the ER in hepatocytes of HFD-fed WT and MUP-uPA mice. Arrows indicate dilated ER (scale bar=1 µm). FIGS. 10D-10F show that LFD or HFD-fed 20 weeks old WT mice were intraperitoneally injected with 1.25 mg/kg tunicamycin (TM) or 150 mM dextrose (vehicle). Representative images of livers and H&E (FIG. 10D) and TUNEL (FIG. 10E) staining of liver sections prepared 36 hrs later (scale bar=100 µm). FIG. 10F shows that Serum ALT in LFD- or HFD-fed 20 weeks old WT mice at 36 hrs after injection of tunicamycin or vehicle. Data are means±S.D. (n=3-4 per group). FIG. 10G shows relative expression of apoB mRNA in mouse livers described in A. FIG. 10H shows serum TG and total cholesterol concentrations in 5 weeks and 16 weeks old WT and MUP-uPA mice kept on LFD or HFD. FIG. 10I shows relative expression of lipogenic regulators in mouse livers described in A (left graph, 5 weeks old; right graph, 16 weeks old). FIG. 10J shows relative expression of genes regulated by the IRE1α-XBP1 pathway in mouse livers described in A (left graph, 5 weeks old; right graph, 16 weeks old). All bar graphs represent means±S.D. n=3 per group). *p<0.05.

FIGS. 11A and 11B show cell death and ROS accumulation in livers of TUDCA- or vehicle-treated HFD-fed MUP-uPA mice were examined by TUNEL (FIG. 11A) and DHE staining (FIG. 11B), respectively (scale bar=100 µm). FIG. 11C shows effects of TUDCA treatment on ER stress and SREBP1 activation in HFD-fed MUP-uPA mouse livers. CHOP protein expression in whole liver and mature SREBP1 in the nuclear fraction were examined by IB analysis. Shown are three individual livers per condition. FIGS. 11D and 11E show the effects of GRP78 overexpression. HFD-fed MUP-uPA mice were intravenously injected with $1 \times 10^9$ pfu of Ad-LacZ or Ad-GRP78. After 6 days the mice (n=6 per group) were sacrificed and hepatic steatosis was analyzed by H&E staining (scale bar=100 µm) (FIG. 11D) and GRP78 expression was determined by IB analysis (FIG. 11E). FIG. 11F shows Serum ALT in 5 weeks old $Chop^{\Delta hep}$/MUP-uPA and $Chop^{F/F}$/MUP-uPA mice. Data are means±S.D. (n=3 per group). FIG. 11G shows the results from IB analysis of ER stress markers in livers of 5 weeks old $Chop^{\Delta hep}$/MUP-uPA and $Chop^{F/F}$/MUP-uPA mice. FIGS. 11H-11K show the effect of hepatocyte CHOP ablation on tumor development and severity of NASH in HFD-fed MUP-uPA mice at 40 weeks of age. FIG. 11H shows tumor numbers and maximal sizes are shown. Results are means±S.E.M. ($Chop^{F/F}$/MUP-uPA, n=17; $Chop^{\Delta hep}$/MUP-uPA, n=11). *p<0.05. Serum ALT (FIG. 11O, expression of indicated proteins in non-tumor tissue (FIG. 11J), and H&E staining of non-tumor areas (scale bar=100 µm) (FIG. 11K) are shown. Data are presented as means±S.D. FIG. 11L shows the results from IHC analysis of CHOP expression in preneoplastic foci (24 weeks old) and liver tumors (40 weeks old) of HFD-fed $Chop^{F/F}$/MUP-uPA and $Chop^{\Delta hep}$/MUP-uPA mice (scale bar=100 µm). FIG. 11M shows a bar graph of the numbers of TUNEL positive cells per 200× field of non-tumor (NT) and tumor areas of liver sections from 40 weeks old HFD-fed $Chop^{F/F}$/MUP-uPA and $Chop^{\Delta hep}$/MUP-uPA mice (scale bar=100 µm). Data are means±S.D. (n=5-6 per group).

FIGS. 12A and 12B show the effect of 4 weeks TUDCA treatment on HFD-fed MUP-uPA mouse liver. IHC of F4/80 (scale bar=100 µm) (FIG. 12A) and TNF mRNA expression (FIG. 12B). Data are means±S.D. (n=5 per group). *p<0.05. FIG. 12C shows the results from H&E staining of liver sections from 5 weeks old MUP-uPA and $Tnfr1^{-/-}$/MUP-uPA mice (scale bar=100 µm). FIG. 12D shows Serum ALT in 5 weeks old MUP-uPA and $Tnfr1^{-/-}$/MUP-uPA mice. Data are presented as means±S.D. (n=3 per group). FIG. 12E shows Serum ALT in 40 weeks old LFD-fed MUP-uPA and Tnfr1$^{-/-}$/MUP-uPA mice. Data are presented as means±S.D. (n=5 per group). FIG. 12F shows body weights of 40 weeks old LFD- or HFD-fed MUP-uPA and Tnfr1$^{-/-}$/MUP-uPA mice (LFD group, MUP-uPA, n=11, Tnfr1$^{-/-}$/MUP-uPA, n=10; HFD group, MUP-uPA, n=14; Tnfr1$^{-/-}$/MUP-uPA, n=11). Results are shown as means±S.D.

FIG. 13A shows relative mRNA amounts of CD44 in non-HcPC and HcPC isolated from DEN-treated WT and Tnfr1$^{-/-}$ mice. Data are means±S.D. (n=3 per group). FIG. 13B shows confirmation of TNFR1 deletion in cancer cells but not in non-tumor liver tissues. Left panel shows that the deleted Tnfr1 allele is detected only in tumor tissues of Tnfr1$^{-/-}$ HcPC-transplanted MUP-uPA mice by genomic DNA PCR. Right panel shows an immunoblot of TNFR1 protein expression. FIGS. 13C-13F show no differences in the severity of NASH and TNF expression in the background liver of MUP-uPA mice transplanted with either WT and Tnfr1$^{-/-}$ HcPC. Body weight (FIG. 13C), serum ALT (FIG. 13D), expression of TNF mRNA in non-tumor tissues (FIG. 13E), liver steatosis (FIG. 13F) and fibrosis (FIG. 13G) in MUP-uPA mice transplanted with either WT or Tnfr1$^{-/-}$ HcPC and kept on LFD or HFD are shown (scale bar=100 µm). Data are expressed as means±S.D. (n=10-11 per group). *p<0.05. FIG. 13H shows the effect of the TNF antagonist etanercept on HFD-induced acceleration of tumor growth. WT HcPC-transplanted MUP-uPA mice were kept on HFD for 5 months as shown in FIG. 6A. 5 mg/kg etanercept or vehicle control was i.p. injected three times a week during the last 7 weeks. Representative images of livers and maximal tumor sizes are shown. Data are expressed as means±S.E.M. (control, n=10; etanercept, n=12). FIG. 13I shows that HcPC were isolated from DEN-WT mice and transplanted into Tnfr1$^{-/-}$/MUP-uPA mice. HcPC-transplanted Tnfr1$^{-/-}$/MUP-uPA mice were divided into two groups that were fed with either LFD or HFD, and 5 months later tumorigenesis was assessed. Representative images of livers and maximal tumor sizes are shown. Data are expressed as means±S.E.M. (n=10 per group). FIG. 13J shows non-tumor (NT) and tumor tissues from MUP-uPA mice transplanted with either WT or Tnfr1$^{-/-}$ HcPC and kept on LFD or HFD were IB analyzed for phosphorylation of ERK, STAT3, JNK, and S6, and expression of cyclin D1.

FIG. 15A shows the results of IB analysis of liver tissue lysates from BL6 (WT) and MUP-uPA mice of indicated ages kept on a LFD or an HFD (n=2-3). FIG. 15B shows histochemistry of livers from 5-month-old mice kept on HFD. Lower panel shows p62 staining in tumors of 10-month-old mice on HFD. Arrows indicate tumor portion. Graphs indicate percentage of areas occupied by stained cells. Results are mean±SD (n=3-5). Scale bars, 100 mm. FIG. 15C shows liver triglyceride (TG) content of 5-month-old mice on HFD. Results are mean±SD (n=4). FIG. 15D shows relative mRNA amounts of fibrogenic markers in mice of indicated genotypes. Results are mean±SD (n=4).

DETAILED DESCRIPTION OF THE INVENTION

Figure 1A:
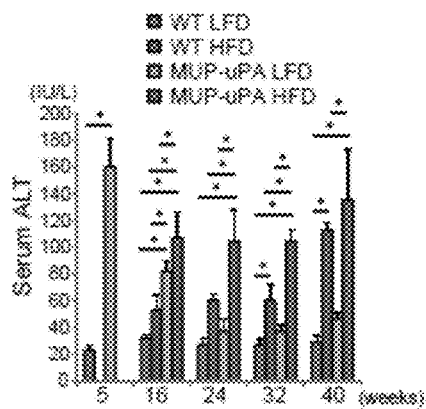
FIGS. 1A-1D are pictorial and graphical diagrams showing that HFD-fed MUP-uPA mice display classical NASH signs.

A common malignancy linked to chronic tissue damage, stress, and environmental carcinogen exposure is HCC, most of which arises as the end stage of chronic liver disease and persistent inflammation, with hepatitis B or C virus (HBV, HCV) infections being the current leading causes (El-Serag, 2011). However, obesity and alcohol consumption, which cause hepatic steatosis (non-alcoholic steatohepatitis (NASH) or alcoholic steatohepatitis (ASH), respectively) and fibrosis, are rapidly growing in their importance as HCC risk factors.

Endoplasmic reticulum (ER) stress has been implicated in the pathogenesis of viral hepatitis, insulin resistance, hepatosteatosis and non-alcoholic steatohepatitis (NASH), disorders that increase risk of hepatocellular carcinoma (HCC). The invention provided herein demonstrates that when combined with hypernutrition, ER stress of liver parenchymal cells results in NASH-like disease that spontaneously progresses to HCC through an inflammatory mechanism dependent on TNF and IκB kinase signaling.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, a "non-human mammal" may be any as long as it is other than human, and includes a transgenic animal and animals for which a production method of ES cells and/or iPS cells has been established. For example, rodents such as mouse, rat, hamster, guinea pig, rabbit, swine, bovine, goat, horse, sheep, dog, cat, monkey are envisioned as non-human mammals.

The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration or administration via intranasal delivery.

As used herein, an "effective amount" is an amount of a substance or molecule sufficient to effect beneficial or desired clinical results including alleviation or reduction in any one or more of the symptoms associated with cancer or NASH. For purposes of this invention, an effective amount of a compound or molecule of the invention is an amount sufficient to reduce the signs and symptoms associated with cancer, such as hepatocellular carcinoma. In some embodiments, the "effective amount" may be administered before, during, and/or after any treatment regimens for cancer.

As used herein, "treatment" is an approach for obtaining beneficial or desired clinical results. For purposes of this invention, beneficial or desired clinical results include, but are not limited to, treatment of cancer, such as hepatocellular carcinoma or NASH.

As used herein, "transgenic organism" refers to an animal in which exogenous DNA has been introduced while the animal is still in its embryonic stage. In most cases, the transgenic approach aims at specific modifications of the genome, e.g., by introducing whole transcriptional units into the genome, or by up- or down-regulating or mutating pre-existing cellular genes. The targeted character of certain of these procedures sets transgenic technologies apart from experimental methods in which random mutations are conferred to the germline, such as administration of chemical mutagens or treatment with ionizing solution. A transgenic organism can include an organism which has a gene knockout or may result for inducing a genetic mutation.

A "genetic knock out" refers to partial or complete suppression of the expression of a protein encoded by an endogenous DNA sequence in a cell. The "knockout" can be affected by targeted deletion of the whole or part of a gene encoding a protein. Alternatively, the transgenic organism can be obtained by the targeted mutation of a functional protein in an embryonic stem cell. As a result, the deletion or mutation may prevent or reduce the expression of the protein in any cell in the whole animal in which it is normally expressed, or results in the expression of a mutant protein having biological function different than the normal/wild-type protein.

The term "knockout animal," and "transgenic animal", refer to a transgenic animal wherein a given gene has been suppressed or mutated by recombination with a targeting vector. It is to be emphasized that the term is intended to include all progeny generations. Thus, the founder animal and all F1, F2, F3, and so on, progeny thereof are included.

The term "chimera," "mosaic," and "chimeric mammal" refer to a transgenic mammal with a knockout or mutation in some of its genome-containing cells.

The term "heterozygote" and "heterozygotic mammal" refer to a transgenic mammal with a knockout or mutation on one of a chromosome pair in all of its genome-containing cells.

The term "homozygote" and "homozygotic mammal" refers to a transgenic mammal with a knockout or mutation on both members of a chromosome pair in all of its genome-containing cells.

A "test agent" or "candidate agent" refers to an agent that is to be screened in one or more of the assays described herein. The agent can be virtually any chemical compound. It can exist as a single isolated compound or can be a member of a chemical (e.g., combinatorial) library. In one embodiment, the test agent is a small organic molecule. The term small organic molecules refers to molecules of a size comparable to those organic molecules generally used in pharmaceuticals. The term excludes biological macromolecules (e.g., proteins, nucleic acids, etc.). In certain embodiments, small organic molecules range in size up to about 5000 Da, up to 2000 Da, or up to about 1000 Da.

Techniques for introducing foreign DNA sequences into the mammalian germ line were originally developed in mice. One route of introducing foreign DNA into a germ line entails the direct microinjection of linear DNA molecules into a pronucleus of a fertilized one-cell egg. Microinjected eggs are subsequently transferred into the oviducts of pseudopregnant foster mothers and allowed to develop. About 25% of the progeny mice inherit one or more copies of the micro-injected DNA. A known technique for generating chimeric and transgenic animals is based on genetically altered embryonic stem cells or embryonic germ cells. A suitable technique for obtaining completely ES cell derived transgenic non-human organisms is described in WO 98/06834.

Embryonic stem (ES) cells are generated and maintained using methods well known to the skilled artisan, such as those described by Doetschman et al. (1985) J. Embryol. Exp. Mol. Biol. 87:27-45). Any line of ES cells can be used, however, the line chosen is typically selected for the ability of the cells to integrate into and become part of the germ line of a developing embryo so as to create germ line transmission of the transgenic/knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934). Still another ES cell line is the WW6 cell line (Ioffe et al. (1995) PNAS 92:7357-7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. (1987)); by Bradley et al. (1986) Current Topics in Devel. Biol. 20:357-371); and by Hogan et al. (Manipulating the Mouse Embryo: A Laboratory Manual, Cold Spring Harbor Laboratory Press, Cold Spring Harbor, N.Y. (1986)).

Variations on the basic technique described above also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targeted gene, resulting in a transgenic animal which expresses a polypeptide of the targeted gene which is defective in one function, while retaining the function of other domains of the encoded polypeptide. This type of "knock-in" mutant frequently has the characteristic of a so-called "dominant negative" mutant because, especially in the case of proteins which homomultimerize, it can specifically block the action of (or "poison") the polypeptide product of the wild-type gene from which it was derived. In a variation of the knock-in technique, a marker gene is integrated at the genomic locus of interest such that expression of the marker gene comes under the control of the transcriptional regulatory elements of the targeted gene. One skilled in the art will be familiar with useful markers and the means for detecting their presence in a given cell.

As mentioned above, the homologous recombination of the above described "knockout" and "knock in" constructs is sometimes rare and such a construct can insert nonhomologously into a random region of the genome where it has no effect on the gene which has been targeted for deletion, and where it can potentially recombine so as to disrupt another gene which was otherwise not intended to be altered. Such non-homologous recombination events can be selected against by modifying the above-mentioned targeting vectors so that they are flanked by negative selectable markers at either end (particularly through the use of the diphtheria toxin gene, thymidine kinase gene, the polypeptide product of which can be selected against in expressing cell lines in an appropriate tissue culture medium well known in the art—e.g., one containing a drug such as ganciclovir. Non-homologous recombination between the resulting targeting vector comprising the negative selectable marker and the genome will usually result in the stable integration of one or both of these negative selectable marker genes and hence cells which have undergone non-homologous recombination can be selected against by growth in the appropriate selective media (e.g., media containing a drug such as ganciclovir). Simultaneous selection for the positive selectable marker and against the negative selectable marker will result in a vast enrichment for clones in which the construct has recombined homologously at the locus of the gene intended to be mutated. The presence of the predicted chromosomal alteration at the targeted gene locus in the resulting stem cell line can be confirmed by means of Southern blot analytical techniques which are well known to those familiar in the art. Alternatively, PCR can be used.

Other methods of making transgenic animals are also generally known. See, for example, Manipulating the Mouse Embryo, (Cold Spring Harbor Laboratory Press, Cold Spring Harbor, N.Y., 1986). Recombinase dependent transgenic organisms can also be generated, e.g. by homologous recombination to insert target sequences, such that tissue specific and/or temporal control of inactivation of a Nod2 gene can be controlled by recombinase sequences.

Animals containing more than one transgenic construct and/or more than one transgene expression construct are prepared in any of several ways. A typical manner of preparation is to generate a series of animals, each containing one of the desired transgenic phenotypes. Such animals are bred together through a series of crosses, backcrosses and selections, to ultimately generate a single animal containing all desired transgenic traits and/or expression constructs, where the animal is otherwise congenic (genetically identical) to the wild type except for the presence of the construct(s) and/or transgene(s).

In another aspect, a transgenic animal can be obtained by introducing into a single stage embryo a targeting vector. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has an advantage in that in most cases the injected DNA will be incorporated into the host gene before the first cleavage (Brinster et al. (1985) PNAS 82:4438-4442). As a consequence, all cells of the transgenic animal will carry the incorporated nucleic acids of the targeting vector. This will in general also be reflected in the efficient transmission to offspring of the founder since 50% of the germ cells will harbor the transgene.

Introduction of the exogenous nucleic acid (e.g., a targeting vector) into the embryo may be accomplished by any means known in the art such as, for example, microinjection, electroporation, or lipofection. Following introduction of the exogenous nucleic acid into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

Reimplantation is accomplished using standard methods. Usually, the surrogate host is anesthetized, and the embryos are inserted into the oviduct. The number of embryos implanted into a particular host will vary by species, but will usually be comparable to the number of offspring the species naturally produces. Transgenic offspring of the surrogate host may be screened for the presence and/or expression of an exogenous polynucleotide (e.g., that of a targeting vector) by any suitable method as described herein. Alternative or additional methods include biochemical assays such as enzyme and/or immunological assays, histological stains for particular marker or enzyme activities, flow cytometric analysis, etc. Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout. Alternatively, the partner may be a parental line. Where in vitro fertilization is used, the fertilized embryo may be implanted into a surrogate host or incubated in vitro, or both. Using either method, the progeny may be evaluated using methods described above, or other appropriate methods.

In previous studies it has been shown that feeding mice exposed to the hepatic carcinogen diethylnitrosamine (DEN) with high fat diet (HFD) strongly enhanced HCC development (Park et al., 2010). Although low grade liver inflammation associated with TNF and IL-6 expression contributes to obesity-promoted HCC development in this model, it should be noted that WT mice do not develop NASH, even after DEN administration and prolonged HFD feeding. Stress responses are elicited by ER and oxidative stresses, viral hepatitis, hemochromatosis, and ASH and NASH (Malhi and Kaufman, 2011), and they control NASH to HCC progression in mice.

In considering possible mechanisms through which obesity may promote HCC development it was therefore decided to study the potential contribution of ER stress, because obesity (Hotamisligil, 2010; Ozcan et al., 2006) and HBV/HCV infections (Malhi and Kaufman, 2011) result in liver ER stress, which promotes hepatosteatosis (Rutkowski et al., 2008). Furthermore, several ER stress markers are elevated in NASH-affected livers (Puri et al., 2008) and ER stress was suggested to cause ballooning degeneration of hepatocytes, a classical sign of NASH (Caldwell et al., 2010). To this end, MUP-uPA mice, that express high amounts of urokinase plasminogen activator (uPA) specifically in hepatocytes and therefore undergo transient ER stress (Sandgren et al., 1991; Weglarz et al., 2000), and WT mice were placed on HFD. Whereas WT mice developed simple steatosis and no HCC, MUP-uPA mice developed NASH-like disease that spontaneously progressed to HCC, whose development was dependent on TNF production by inflammatory liver macrophages and TNFR1-IKKβ signaling in hepatocytes. The results provided herein show that NASH and progression to steatohepatitic HCC may be prevented or ameliorated by anti-TNF drugs.

Accordingly, in one aspect, the invention provides a non-human mammalian model of HCC, and a method of making the same. The non-human mammal includes HCC progenitor cells transplanted therein, and is subjected to a high fat diet (HFD). Thus, the method includes transplanting HCC progenitor cells into a non-human mammal and subjecting the mammal to a high fat diet (HFD). In one embodiment, the non-human mammal is a mouse.

ER stress and the unfolded protein response (UPR) are unregulated in many cancers and may be associated with drug resistance and adaptation to the transformed state (Wang et al., 2010). Elevated ER stress was also detected in precancerous conditions that precede HCC development, including HBV and HCV infections (Malhi and Kaufman, 2011) and NASH (Farrell et al., 2012; Tilg and Moschen, 2010). However, until recently, it has not been examined whether the ER stress response, which contributes to insulin resistance and hepatic steatosis (Hotamisligil, 2010) stimulates HCC development. The results provided herein indicate that although transient ER stress in MUP-uPA mice that are kept on low fat diet (LFD) does not trigger hepatocarcinogenesis, when combined with hypernutrition it elicits a more sustained stress response that also includes extensive oxidative stress. This response leads to spontaneous NASH development and progression to HCC whose features closely resemble steatohepatitic HCC in NASH patients. The studies disclosed herein suggest several potential mechanisms related to ER stress and HFD feeding that cooperate to induce HCC development. First, by stimulating hepatosteatosis (lipid droplet accumulation), HFD sustains a modest degree of ER stress in MUP-uPA mice, which otherwise would be switched off upon extinction of uPA expression. Second, ER stress promotes SREBP1 activation, enhancing lipogenesis and increasing the degree of hepatic steatosis beyond what is achieved by HFD alone. Third, ER stress and steatosis increase ROS production in hepatocytes to cause oxidative stress and its sequalae, which include genomic instability, oncogenic mutations and/or gene copy number changes. Fourth, ER and oxidative stress increase the susceptibility of hepatocytes to lipotoxic death, thereby releasing inflammatory mediators that attract and activate monocytes/macrophages. Fifth, TNF and other mediators produced by activated inflammatory macrophages stimulate compensatory hepatocyte proliferation and expand HCC progenitors. TNF further reinforces the inflammatory microenvironment and induces expression of chemokines (CCL2, CCL7 and CXCL13) and growth factors/cytokines (IL-1β, IL-6, TNF itself, lymphotoxin and HGF) both by HCC progenitor cells (HcPC) and surrounding cells. The concerted action of these factors contributes to the development of NASH-like pathology and NASH to HCC progression. Mutually reinforcing ER stress and hepatosteatosis (Malhi and Kaufman, 2011) are needed to set this pathogenic cascade in motion.

The requirement for two hits (hepatosteatosis and ER stress) for induction of HCC development in MUP-uPA mice supports what has been proposed to drive NASH development, a pre-HCC condition, in humans (Day and James, 1998; Tilg and Moschen, 2010). Although simple steatosis ("not-NASH") is an extremely common disorder, affecting nearly 30% of the US population, only 10%-20% of these patients develop NASH. In the absence of known genetic factors it was proposed that NASH development depends on multiple secondary hits, which may include microbiota related factors, food additives, dysbiosis, IL-6 and TNF from adipose tissue, mitochondrial dysfunction and oxidative or ER stress (Farrell et al., 2012; Tilg and Moschen, 2010). Although these are considered secondary hits, they may act as pre-existing risk factors prior to hepatosteatosis caused by HFD. Nonetheless, in humans, unlike MUP-uPA mice, it has been extremely difficult to detect the presence of such risk factors as they do not lead to overt liver damage (elevated ALT) prior to development of a steatotic liver due to hypernutrition. Given its presence in other pre-HCC conditions (Malhi and Kaufman, 2011), the focus of this study was on the role of ER stress. Remarkably, feeding HFD to MUP-uPA mice resulted in steatohepatitis that closely resembled human NASH and two of the main pathological features, ballooning degeneration and hepatocyte death, were also rapidly induced by administration of tunicamycin to HFD-fed mice. By itself, short term tunicamycin did not damage the liver, but due to toxicity that may be associated with long term use, we did not examine if tunicamycin induces NASH and HCC in HFD-fed WT mice. Notably, NASH-like disease in MUP-uPA mice is associated with the same metabolic alterations linked to NASH in humans, and is not accompanied by weight loss, as seen in other NASH models that are based on feeding mice with toxic diets that induce liver damage (Farrell et al., 2012). Furthermore, the HFD-fed MUP-uPA mouse is currently the only model for studying obesity-induced HCC development that does not rely on administration of liver toxins or carcinogens. The major NASH-promoting effects of ER stress in this system are increased lipogenesis, oxidative stress and susceptibility to lipotoxic cell death. ER stress contributes to SREBP activation, thereby stimulating lipogenesis (Kammoun et al., 2009). ER and oxidative stress also upregulate several cell death mediators including TRB3 and DR5, but the exact mechanisms through which ER stress promotes cell death remain controversial (Xu et al., 2005) and these results indicate that in normal hepatocytes it is CHOP-independent. Although ER stress causes insulin resistance (Hotamisligil, 2010; Ozcan et al., 2006) and insulin resistance was proposed to contribute to HCC development, the results provided herein suggest that insulin resistance has no obvious role in HCC development because it is not higher in MUP-uPA mice than in HFD-fed WT mice.

A consequence of ER stress and lipotoxic hepatocyte death that contributes to HCC development is induction of TNF-dependent steatohepatitis. In addition to amplifying liver inflammation and shaping the inflammatory microenvironment nearby HcPC clusters, TNF contributes to hepatosteatosis and liver damage. Although TNFR1 engagement can trigger apoptosis, it is not responsible for ER stress-induced death in lean MUP-uPA mice and its contribution to liver damage in HFD-fed mice is proportional to its effect on lipogenesis and may be indirect. TNF, however, directly stimulates HCC growth through NF-κB activation. However, additional downstream TNFR1 effectors, such as JNK (Sakurai et al., 2008), may also contribute to HCC growth as well as hepatocyte death. TNF expression is also elevated in human NASH and anti-TNF therapy may reduce NASH activity (Schramm et al., 2008).

ER stress has also been shown to enhance oxidative stress, which is relieved by nuclear factor erythroid 2 (NRF2) by inducing expression of genes encoding antioxidant and detoxifying enzymes (Suzuki et al., 2013). NRF2 is regulated post-translationally by the E3 ubiquitin ligase Keap1, which induces NRF2 ubiquitination and proteasomal degradation. Upon accumulation of reactive oxygen species (ROS) or electrophiles, Keap1 is oxidized and unable to bind newly translated NRF2, which is stabilized and enters the nucleus to activate genes harboring antioxidant response elements. Because products of NRF2-regulated genes detoxify electrophiles and promote glutathione synthesis, transient activation of this system was proposed to inhibit carcinogenesis in liver and other organs (Hayes and McMahon, 2009; Suzuki et al., 2013). Surprisingly, however, KEAP1 inactivating mutations occur in lung cancer and HCC, and activating mutations in the gene encoding NRF2, NFE2L2, that inhibit Keap1-mediated degradation were found in lung, esophageal, skin, and liver cancers. Together, NFE2L2 and KEAP1 mutations occur in 14% of HCC specimens and are considered to be driver mutations. NRF2 was proposed to contribute to liver carcinogenesis by inhibiting senescence or death of initiated hepatocytes undergoing oxidative stress (Hayes and McMahon, 2006), but direct support for this hypothesis, first postulated by Farber (1990), is lacking. Curiously, carcinogen-induced dysplastic lesions in rats, known as foci of altered hepatocytes (FAH), express high amounts of glutathione S-transferase P1 (Gstp1), NAD(P)H:quinone oxidoreductase 1 (Nqo1), and other protective enzymes, now known as NRF2 targets (Hayes and McMahon, 2009). As a result, FAH are probably more resistant to oxidative stress and environmental toxins than the surrounding liver. Thus, antioxidants may promote rather than suppress HCC development, as previously found (Maeda et al., 2005).

It was also questioned whether FAH, also found in human cirrhotic and preneoplastic livers, are true HCC progenitors or reflect compensatory proliferation triggered by liver damage. This controversy was settled by isolating small hepatocytic cells from mouse dysplastic lesions that give rise to HCC after transplantation into a damaged liver (He et al., 2013). In addition to cancer stem cell markers, HCC progenitor cells (HcPC) exhibit elevated p62, which also accumulates in livers of high-fat diet (HFD)-fed MUP-uPA mice that develop NASH and progress to HCC (Nakagawa et al., 2014). p62 is known to accumulate in most, if not all, chronic liver diseases that progress to HCC (Denk et al., 2006).

p62, encoded by SQSTM1, is an autophagy adaptor and a signaling scaffold with an N-terminal oligomerization domain (PB 1) and a ubiquitin association domain (UBA) at its C terminus (Komatsu et al., 2012). p62 also harbors light-chain protein 3 (LC3) motif and Keap1 interacting motif (KIR), through which it binds LC3 on phagophore membranes and cytoplasmic Keap1, respectively. A main p62 function is to deliver polyubiquitinated proteins and organelles for autophagosomal-lysosomal degradation. Interference with autophagic flux attenuates p62 degradation (Komatsu et al., 2012). The latter results in p62 accumulation and oligomerization, aggregation of ubiquitinated proteins, Keap1 titration, and NRF2 stabilization. As NRF2 can induce p62 expression (Jain et al., 2010), p62 accumulation can trigger a self-amplifying autoregulatory loop that sustains NRF2 activation and p62 overexpression. p62 also binds TRAF6 to promote nuclear factor kB (NF-kB) activation (Sanz et al., 2000), and NF-kB can also induce p62 expression. Under nutrient-rich conditions, the p62/TRAF6 interaction also enhances mammalian target of rapamycin complex 1 (mTORC1) activation. Importantly, p62 is a major component of intracellular hyaline bodies, Mallory-Denk bodies (MDB), and hybrid inclusions (Denk et al., 2006), which are hallmarks of chronic liver diseases that greatly enhance HCC risk. p62-containing aggregates have been detected in 50% of surgical HCC specimens (Denk et al., 2006), but their significance remains unknown.

Of note, whole-body p62 disruption suppresses benign adenomas in autophagy-deficient livers. These tumors, however, are not cancerous and thus the role of p62 and its mechanism of action in HCC initiation remain unknown, although it was shown that p62 maintains malignancy of HCC cell lines (Ichimura et al., 2013; Inami et al., 2011). p62 has been suggested to act as an oncoprotein in renal cell carcinoma by promoting mTORC1 activation (Li et al., 2013), while other studies have suggested it acts via NF-kB or oxidative stress. p62 also accumulates in endometrial cancer. Yet in no case was it investigated whether p62 accumulation in a preneoplastic tissue increases the risk of cancer initiation.

Although p62 was upregulated in autophagy-deficient livers and p62 ablation attenuated the genesis of benign hepatic adenomas, and inhibited proliferation and growth of established HCC cell lines (Ichimura et al., 2013; Inami et al., 2011), the role of p62 in HCC initiation within a precancerous liver was not previously investigated. The data provided herein shows that in human patients with early HCC, p62 accumulation in non-tumor liver correlates with much faster post-therapeutic recurrence and reduced disease-free survival. Hence, patients with high p62 expression in non-tumor tissue need closer surveillance and additional intervention. Using four distinct mouse HCC models of differing etiology, it has been shown that p62 is needed for initiation of malignant tumors with classical HCC features. The most dramatic dependence on p62 was exhibited by $Tsc1^{\Delta hep}$ mice, in which HCC development depends on mTORC1, which is also activated by hypernutrition, causing attenuation of autophagy and p62 accumulation. Nonetheless, HFD feeding causes p62 accumulation in MUP-uPA and STZ but not in WT mice. Thus, p62 is not linked to development of steatotic changes; rather, it is strictly required for NASH to HCC progression. The results provided herein also indicate that p62 accumulation can initiate HCC development, suggesting it is a critical preneoplastic event that leads to non-mutational activation of three important cancer drivers: NRF2, mTORC1, and c-Myc.

Another critical mediator of p62-induced hepatocarcinogenesis is NRF2, whose activation by p62 depends on Keap1 binding. A point mutation in the p62 KIR domain, which prevents Keap1 binding (Suzuki et al., 2013), blocks NRF2 activation and abolishes p62 oncogenic activity. Importantly, NRF2 is mutationally activated in approximately 14% of human HCCs. NRF2 is also mutationally activated in chemically induced HCC in rats, where Nfe2l2 or Keap1 mutations occur in 70% of early lesions. Given the dependence of NRF2 activation on p62 in the animal models provided herein, the main driver of NRF2 activation in mouse HCC and human HepG2 cells is p62 rather than mutations. Furthermore, no NRF2 or KEAP1 mutations were observed in human dysplastic lesions. NRF2 ablation in Atg5$^{\Delta hep}$ mice inhibits the development of adenomas, but these are benign tumors that emerge in autophagy-deficient livers and their relationship to HCC is questionable.

NRF2 activation and upregulation of its targets are common in human and rodent HCCs, where they occur in the majority of FAH/dysplastic lesions (Hayes and McMahon, 2006). It was proposed, but never proved, that NRF2 activation and consequent induction of antioxidant and detoxifying enzymes allow these lesions to survive in chronically stressed livers, where ROS accumulation is readily detected (Nakagawa et al., 2014; Sakurai et al., 2008). Curiously, however, chronic upregulation of these protective enzymes does not inhibit ROS-mediated mutagenesis, as human HCCs contain multiple mutations in addition to those that activate NRF2. On the contrary, persistent NRF2 activation promotes survival of HcPC and allows them to accumulate additional mutations. Congruent with this notion, it was found that p62 is required for survival of hepatocytes that accumulate high amounts of superoxides and stain positively with DHE. Although p62 ablation reduces expression of antioxidant enzymes, it decreases rather than increases the number of DHE-positive, ROS-containing cells. Most likely, without NRF2-dependent defenses cells undergoing extensive ROS accumulation die and cannot serve as HCC progenitors. Although exogenous p62 may function by inducing endogenous p62, both this function and activation of the antioxidant response require a functional KIR domain. NRF2 was therefore suggested to induce metabolic reprogramming that favors cell proliferation. However, this effect was mainly detected in cancer cell lines that exhibit sustained AKT activation, which is certainly not the case in livers of Tsc1$^{\Delta hep}$ or HFD-fed MUP-uPA and STZ-HFD mice, in which AKT is not activated due to hepatic insulin resistance.

Without being bound by theory, it appears that NRF2 only increases HCC risk in the presence of activated mTORC1, as occurs in Tsc1$^{\Delta hep}$ livers and during NASH-driven HCC development. Although NRF2 induces Sqstm1 transcription and p62 activates NRF2, the latter effect requires p62 phosphorylation by mTORC1 (Ichimura et al., 2013). The ability of p62 to oligomerize and aggregate ubiquitinated proteins was suggested to promote tumorigenesis by inducing oxidative stress, and p62 ablation in Atg7$^{\Delta hep}$ liver was reported to reduce oxidative stress (Komatsu et al., 2007), results that are not entirely consistent with the current understanding of p62 importance in maintaining liver antioxidant defenses.

Although HFD feeding to MUP-uPA mice results in upregulation of multiple cytokines and growth factors including several that stimulate HCC development, namely HGF and lymphotoxin (Haybaeck et al., 2009), anti-TNF therapy inhibited the obesity-enhanced progression of HcPC to HCC and TNFR1 ablation almost completely blocked HCC development. It is therefore also hypothesized that anti-TNF drugs, perhaps in combination with improved intrahepatic delivery of chemical chaperons, such as TUDCA, should be evaluated for inhibition of NASH to HCC progression and treatment of steatohepatitic HCC along with more conventional chemotherapy.

The results provided herein demonstrate the existence of a common pathway through which diverse etiological factors, including HBV and HCV infections, NASH, and ASH trigger premalignant changes that progress to HCC by inducing p62 accumulation and subsequent NRF2, mTORC1, and c-Myc activation. The p62-Keap1-NRF2 pathway allows HcPC with high ROS content to survive in the chronically stressed liver environment and accumulate numerous mutations that commit them to the malignant fate under conditions where the metabolic and proliferative functions of mTORC1 and c-Myc are also activated. Elevated p62 in human liver predicts rapid recurrence of resectable HCC. Thus, small molecules that interfere with p62 binding to Keap1 and/or TRAF6, which is needed for mTORC1 activation, may be useful for preventing progression of chronic liver disease to HCC as well as attenuate recurrence of resectable HCC.

As such, in another aspect, the invention provides a method of suppressing development of hepatocellular carcinoma (HCC) in a subject. The method includes administering to the subject an effective amount of an agent that modulates expression and/or activity of human TNF, p62, NRF2, mTORC1, and/or c-Myc, thereby suppressing development of HCC. In one embodiment, expression and/or activity of human TNF or p62 is suppressed. The subject may be a mammal, such as a human, and may have been diagnosed as having or at risk for non-alcoholic steatohepatitis (NASH). The method may further include administering tauroursodeoxycholic acid (TUDCA) in combination with the agent.

In another aspect, the invention provides a method of treating hepatocellular carcinoma. The method includes administering to a subject in need thereof an effective amount of an agent that mediates expression and/or activity of human TNF, p62, NRF2, mTORC1, and/or c-Myc, thereby treating hepatocellular carcinoma. In one embodiment, the agent suppresses hepatic inflammation in the subject. In another embodiment, expression and/or activity of human TNF or p62 is decreased. The subject may be a mammal, such as a human, and may have been diagnosed as having or at risk for hepatocellular carcinoma. The subject may be a mammal, such as a human, and may have been diagnosed as having or at risk for non-alcoholic steatohepatitis (NASH). The method may further include administering tauroursodeoxycholic acid (TUDCA) in combination with the agent.

Changes in expression level can be detected by measuring changes in mRNA and/or a nucleic acid derived from the mRNA (e.g., reverse-transcribed cDNA, etc.). In order to measure expression levels of genes of interest, it is desirable to provide a nucleic acid sample for such analysis. In certain embodiments the nucleic acid is found in or derived from a biological sample. The term "biological sample", as used herein, refers to a sample obtained from an organism or from components (e.g., cells) of an organism, or from cells in culture. The sample may be of any biological tissue or fluid. Biological samples may also include organs or sections of tissues such as frozen sections taken for histological purposes.

Frequently it is desirable to amplify the nucleic acid sample prior to assaying for expression level. Methods of amplifying nucleic acids are well known to those of skill in the art and include, but are not limited to polymerase chain reaction (PCR, see. e.g, Innis, et al., (1990) PCR Protocols. A guide to Methods and Application. Academic Press, Inc. San Diego,), ligase chain reaction (LCR) (see Wu and Wallace (1989) Genomics 4: 560, Landegren et al. (1988) Science 241: 1077, and Barringer et al. (1990) Gene 89: 117, transcription amplification (Kwoh et al. (1989) Proc. Natl. Acad. Sci. USA 86: 1173), self-sustained sequence replication (Guatelli et al. (1990) Proc. Nat. Acad. Sci. USA 87: 1874), dot PCR, and linker adapter PCR, etc.).

In another embodiment, amplification-based assays can be used to measure expression (transcription) levels of genes of interest. In such amplification-based assays, the target nucleic acid sequences act as template(s) in amplification reaction(s) (e.g., Polymerase Chain Reaction (PCR) or reverse-transcription PCR, or quantitative PCR (e.g., quantitative RT-PCR). In a quantitative amplification, the amount of amplification product will be proportional to the amount of template in the original sample. Comparison to appropriate (e.g., healthy tissue or cells unexposed to the test agent) controls provides a measure of the transcript level for the gene of interest.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) PCR Protocols, A Guide to Methods and Applications, Academic Press, Inc. N.Y.). One approach, for example, involves simultaneously co-amplifying a known quantity of a control sequence using the same primers as those used to amplify the target. This provides an internal standard that may be used to calibrate the PCR reaction.

Since the non-human animal of the present invention strongly reflects the pathology of HCC in humans, the present invention also provides a method of screening for a substance for the prophylaxis and/or treatment of HCC by using the non-human animal. Particularly, since the non-human animal of the present invention has been demonstrated to develop NASH and progress to HCC, and accumulates p62, thus strongly reflecting the pathology of HCC, the non-human animal or cultured cells prepared from the non-human animal can be applied to screening for a prophylactic or therapeutic drug for HCC, elucidation of the mechanism of HCC, and development of a new treatment method for HCC.

Accordingly, the present invention provides a screening method for a test agent, which characteristically uses the non-human animal of the present invention or tissue or cultured cells prepared from the non-human animal. Particularly, since the non-human animal of the present invention displays NASH-driven HCC, the non-human animal, tissues from the non-human animal, or cultured cells prepared from the non-human animal can be applied to screening for a prophylactic or therapeutic drug for HCC, elucidation of the mechanism of NASH-driven HCC, and development of a new treatment method for NASH and/or HCC.

The method of screening for a substance for the prophylaxis and/or treatment of HCC of the present invention includes (a) a step of administering a test substance to a non-human animal obtained by the present invention, and (b) a step of analyzing the tissue or organ of the aforementioned non-human animal. More specifically, it includes steps of administering a test substance to the aforementioned non-human animal and control group (control), measuring the levels of expression of various markers of HCC, as described herein in both animals, and comparing them, as well as a step of confirming the effect of the test substance based on the aforementioned comparison results.

Virtually any agent can be screened according to the methods of this invention. Such agents include, but are not limited to nucleic acids, proteins, sugars, polysaccharides, glycoproteins, lipids, and small organic molecules. The term small organic molecule typically refers to molecules of a size comparable to those organic molecules generally used in pharmaceuticals. In one embodiment, small organic molecules can range in size up to about 5000 Da, up to 2000 Da, or up to about 1000 Da.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233-1250).

Any of the assays described herein are amenable to high-throughput screening (HTS). Moreover, the cells and/or animal models utilized in the methods of this invention need not be contacted with a single test agent at a time. To the contrary, to facilitate high-throughput screening, a single cell may be contacted by at least two, by at least 5, by at least 10, or by at least 20 test compounds. If the cell scores positive, it can be subsequently tested with a subset of the test agents until the agents having the activity are identified.

High throughput assays for hybridization assays, immunoassays, and for various reporter gene products are well known to those of skill in the art. For example, multi-well fluorimeters are commercially available (e.g., from Perkin-Elmer).

Thus, in another aspect, the invention provides a method of screening for an agent that suppresses development of hepatocellular carcinoma in a mammal. The method includes contacting a cell with a test agent, and detecting decreased expression or activity of TNF, as compared to expression or activity of TNF in a control as an indication that the test agent is an agent that suppresses development of hepatocellular carcinoma in a mammal.

In another aspect, the invention provides a method of screening a drug candidate for treating heptocellular carcinoma in a subject. In one embodiment, the method includes administering a potential drug candidate to a mouse model having had transplanted therein HCC progenitor cells and subsequently having been subjected to a high fat diet (HFD), measuring a response in TNF expression or activity to the drug candidate, comparing the measured TNF expression or activity with that of a wild type mouse, and selecting the drug candidate based on reduced or suppressed TNF expression or activity after the administration of the drug candidate and the comparison with the wild type mouse. In another embodiment, the method includes administering a potential drug candidate to a MUP-uPA mouse model having been subject to HFD, measuring a response in TNF expression or activity to the drug candidate, comparing the measured TNF expression or activity with that of a wild type mouse, and selecting the drug candidate based on reduced or suppressed TNF expression or activity after the administration of the drug candidate and the comparison with the wild type mouse.

All methods may further include the step of bringing the active ingredient(s) into association with a pharmaceutically acceptable carrier, which constitutes one or more accessory ingredients. The term "pharmaceutically acceptable," when used in reference to a carrier, is meant that the carrier, diluent or excipient must be compatible with the other ingredients of the formulation and not deleterious to the recipient thereof.

Pharmaceutically acceptable carriers useful for formulating an agent for administration to a subject are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally, intranasally or any other such method known in the art. The pharmaceutical composition also can contain a second (or more) compound(s) such as a diagnostic reagent, nutritional substance, toxin, or therapeutic agent, for example, a cancer chemotherapeutic agent and/or vitamin(s).

The total amount of a compound or composition to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the plasma expander used to treat blood loss in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

Accordingly in another aspect, the invention provides a composition for treating NASH-driven hepatocellular carcinoma in a mammal. The composition includes an agent that mediates expression and/or activity of human TNF in a mammal.

The following examples are intended to illustrate but not limit the invention.

Example 1

Experimental Procedures

Animals—

MUP-uPA mice were kindly provided by the University of Wisconsin-Madison (Weglarz et al., 2000). As disclosed in Weglarz, the MUP-uPA transgene was generated by joining the mouse major urinary protein (MUP) promoter to a previously constructed genomic coding sequence from the mouse uPA gene that carried the 3' noncoding region and polyadenylation sequence from the human growth hormone gene. The parental MUP plasmid was a pUC18 derivative containing the MUP promoter sequence terminating in the first exon at +29 and flanked by a unique NdeI site upstream and by a KpnI site downstream within a polylinker. The 2.5-kb MUP promoter element was excised with NdeI and KpnI, then ligated into the NdeI/KpnI-cut plasmid vector puPA-human growth hormone/Nde. The resulting plasmid, pMUP-uPA, was digested with NdeI and NotI, and the excised transgene DNA was microinjected into fertilized C57BL/6 or FVB strain mouse eggs using standard methods.

Liver-specific Ikkβ$^{\Delta hep}$ mice were described (Maeda et al., 2005). Chop$^{\Delta hep}$ mice were generated by crossing Alb-Cre mice with Chop$^{F/F}$ mice. Tnfr1$^{-/-}$ mice were purchased from Jackson Laboratory (Bar Harbor, Me.). All mouse lines were either on a pure C57BL/6 genetic background or crossed into it for at least 10 generations. Studies were conducted on male mice maintained in filter-topped cages on autoclaved water and regular chow diet (LFD, composed of 12% fat, 23% protein, 65% carbohydrates based on caloric content) or HFD (composed of 59% fat, 15% protein, 26% carbohydrates based on caloric content; BioServ).

Sqstm1$^{F/F}$ and Tsc1$^{F/F}$ mice (Mori et al., 2009; Muller et al., 2013) were backcrossed to C57BL/6 mice for at least seven generations and then bred with Alb-Cre mice (also C57BL/6) to generate Sqstm1$^{F/F}$; Alb-Cre (Sqstm1$^{\Delta hep}$) and Tsc1$^{F/F}$; Alb-Cre (Tsc1$^{\Delta hep}$) mice, respectively. Sqstm1$^{\Delta hep}$ mice were crossed to Tsc1$^{\Delta hep}$ and MUP-uPA mice to generate Tsc1/Sqstm1$^{\Delta hep}$ and Sqstm1$^{\Delta hep}$/MUP mice, respectively. All studies used male mice, and were in accordance with NIH guidelines. Mice were maintained in filter-topped cages on autoclaved chow diet (lowfat diet (LFD), composed of 12% fat, 23% protein, 65% carbohydrates based on caloric content) or HFD, composed of 59% fat, 15% protein, and 26% carbohydrates based on caloric content) (Bio-Serv) and water.

HcPC Isolation and Transplantation—

DEN (Sigma) was i.p. injected into male mice (25 mg/kg) on postnatal day 14. After 5 months, HcPCs were isolated as described and transplanted into 4 weeks old MUP-uPA (He et al., 2013).

Primary Hepatocytes and Macrophage Cultures—

Primary hepatocytes were isolated (He et al., 2013) and cultured in William's E medium with 10% FBS on collagen-coated plates. PA (Sigma) was dissolved in ethanol at 50° C. and then diluted in bovine serum albumin-containing RPMI-1640 medium that was applied to primary hepatocytes at a final concentration of 200 (to analyze signal transduction) or 300 (to analyze cell death) μM.

Hepatic Lipid Profile—

Hepatic lipids were extracted with chloroform/methanol (2:1 v/v), and TG and total cholesterol contents were measured with Triglyceride Reagent Set (Pointe Scientific) and Cholesterol E (Wako), respectively. FA composition was analyzed by gas-chromatography at SRL Inc., Tokyo, Japan.

Human Liver Samples—

Human tissue specimens were retrospectively obtained from liver biopsies or liver resections, and fixed in buffered formalin and embedded in paraffin using standard methods. Corresponding clinical data were obtained from medical records and de-identified.

Accession Number—

The GEO accession number for RNA-seq data is GSE77323.

Biochemical Analyses and Reagents—

Immunoblotting and real-time Q-PCR were described (Maeda et al., 2005). Antibodies used were against: phospho-ERK, ERK1/2, phospho STAT3, STAT3, phospho-JNK, JNK1/2, phospho-S6, S6, p65, cyclinD1, YAP (all from Cell Signaling); K19, GRP78, SREBP1, CHOP, CCL7, TNFR1 (all from Santa Cruz Biotechnology); phospho-eIF2α (Upstate); tubulin (Sigma); F4/80 (Molecular Probes); Ki67 (Gene Tex); AFP (Biocare Medical); TNF (R&D Systems); B220 (BD Pharmingen). TUDCA and 4-PBA were from Calbiochem and Sigma, respectively. GSH:GSSG ratio was analyzed using GSSG/GSH Quantification Kit (Dojindo).

Histology—

Livers were fixed in 10% neutral-buffered formalin or 4% paraformaldehyde, embedded in paraffin, sectioned, and stained with hematoxylin and eosin (H&E), Sirius Red, and processed for IHC. For frozen block preparation, tissue was embedded in Tissue-Tek OCT compound (Sakura Finetek). IHC and IF analyses were described (He et al., 2013). Stained areas were quantitated with Image J software. Slides were incubated with primary antibodies, followed by secondary antibodies labeled with Alexa488 or Alexa594 (Molecular Probes). TUNEL staining was performed using an Apoalert DNA Fragmentation Assay kit (Clontech). Accumulation of superoxide anions was examined by DHE staining (Sakurai et al., 2008). Tissue sample preparation and EM analysis were described (Lee et al., 2012).

Infection of Recombinant Adenovirus—

Primary hepatocytes were infected with recombinant adenovirus encoding β-galactosidase (LacZ) and GRP78 at a titer of 50 plaque-forming unit/cell 4 hours after isolation.

Statistical Analyses—

Statistical analyses were performed using Student's t-test or one-way analysis of variance followed by the Tukey-Kramer test for multiple comparisons. A p value <0.05 indicated statistical significance.

Example 2

HFD Induces NASH Signs and Spontaneous HCC in MUP-uPA Mice

Figure 1B:
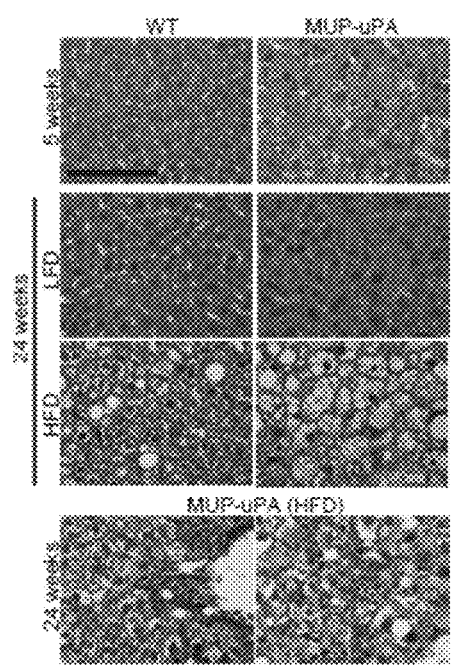
Figure 1C:
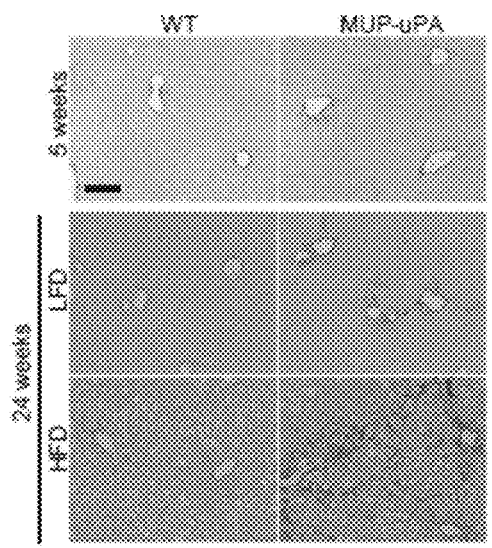
Figure 8A:
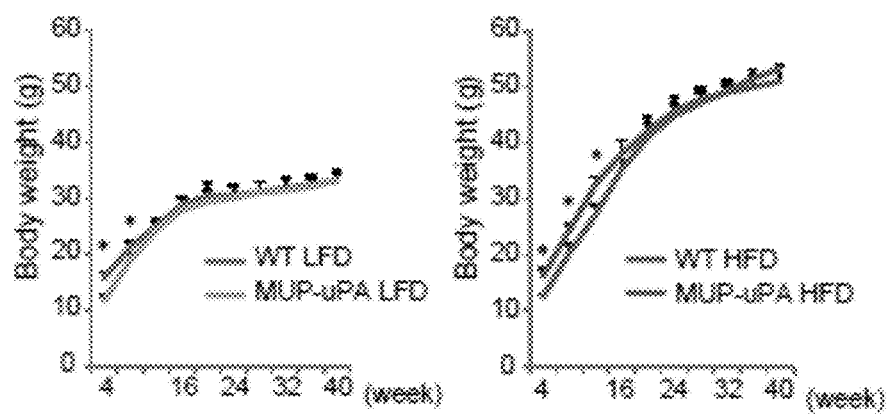
FIGS. 8A-8F are pictorial and graphical diagrams showing the effects of HFD on MUP-uPA mice.
Figure 8B:
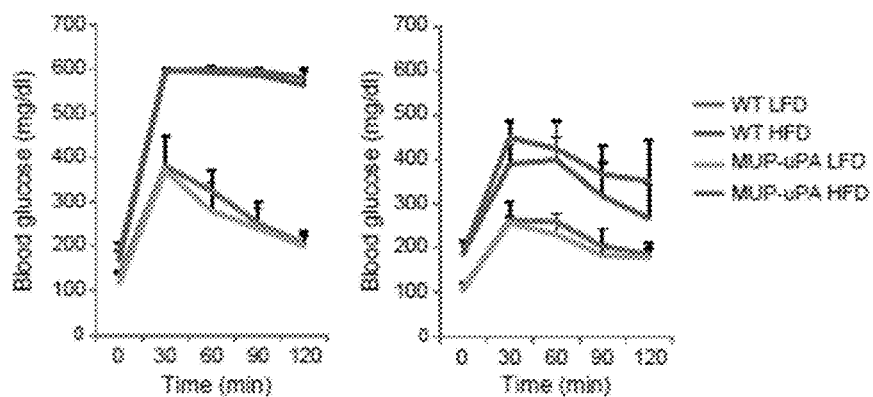
Figure 8C:
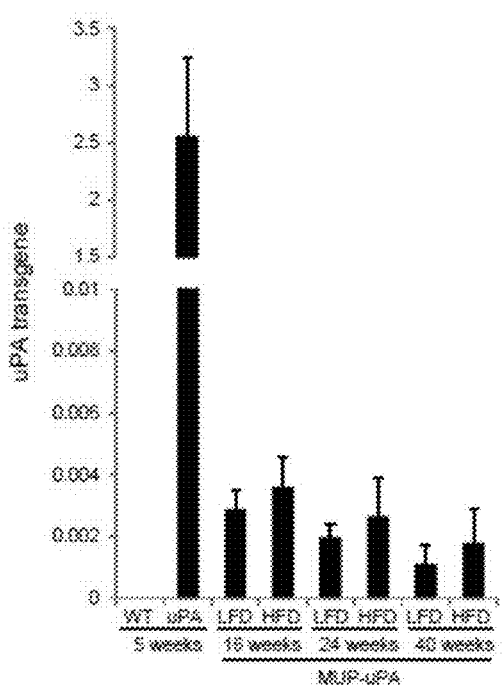
Figure 8D:
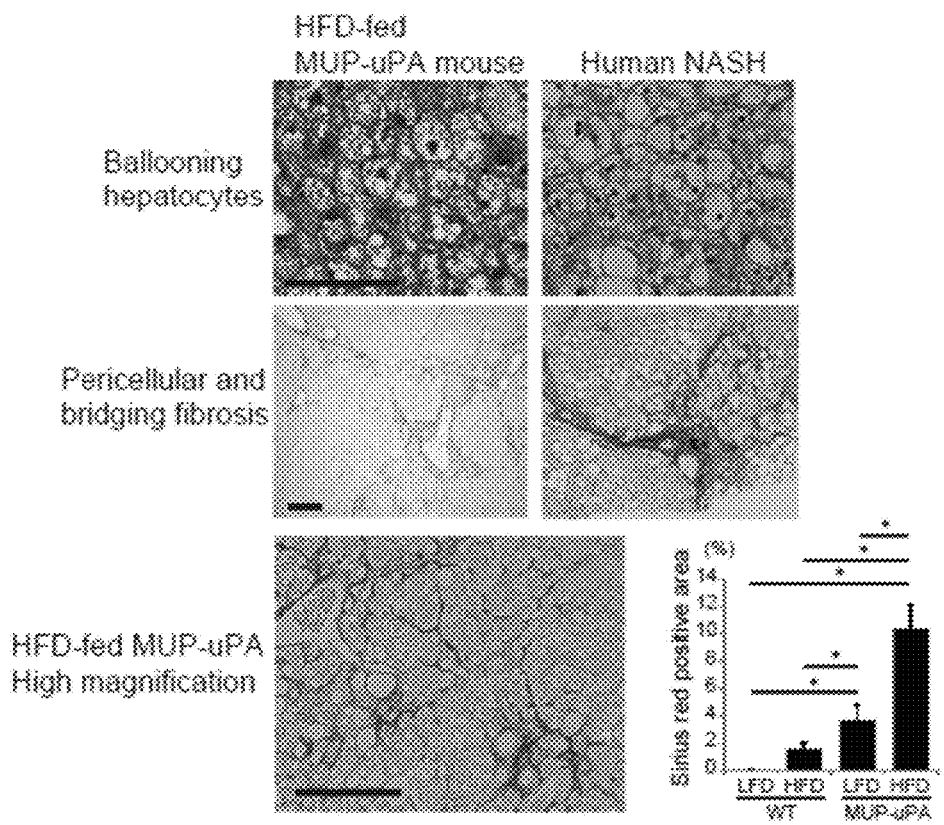
Figure 8E:
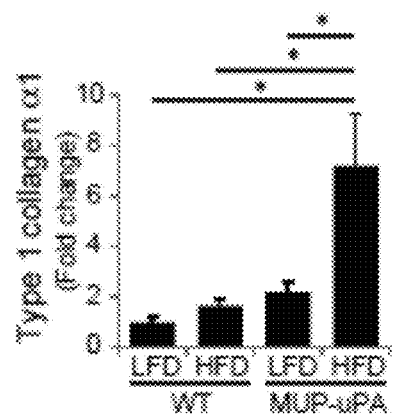

WT and MUP-uPA mice were placed on HFD (60% of calories are fat derived), starting at 6 weeks of age. Body weight and glucose intolerance did not differ between the two strains (FIGS. 8A and 8B). As previously reported (Weglarz et al., 2000), serum alanine aminotransferase (ALT) in MUP-uPA mice on normal chow diet (LFD) was markedly elevated at 5 weeks of age but rapidly declined, likely due to replacement of dying hepatocytes with new cells in which uPA expression is extinguished (Sandgren et al., 1991; Weglarz et al., 2000) (FIG. 8C). However, HFD feeding maintained high serum ALT throughout the observation period (FIG. 1A), even though it did not restore uPA expression (FIG. 8C). By contrast, in WT mice HFD substantially elevated ALT only after 32 weeks, reaching a level similar to MUP-uPA mice at 40 weeks. Examination of liver histology revealed hepatocyte damage, evidenced by tissue clearing, in 5 weeks old MUP-uPA mice but this had almost disappeared at 24 weeks on LFD, except for mild inflammation and spotty necrosis (FIG. 1B). As reported (Park et al., 2010), HFD-fed WT mice showed pronounced steatosis but little inflammation by 24 weeks (FIG. 1B). At that time, HFD-fed MUP-uPA mice exhibited extensive immune infiltration into the liver and numerous ballooning hepatocytes, both of which are important diagnostic features of human NASH (Brunt, 2001). Furthermore, HFD-fed MUP-uPA mice showed pericellular and bridging fibrosis, resembling the pattern in human NASH (FIGS. 1C and 8D). This was accompanied by increased expression of type 1 collagen al mRNA (FIG. 8E).

Figure 1D:
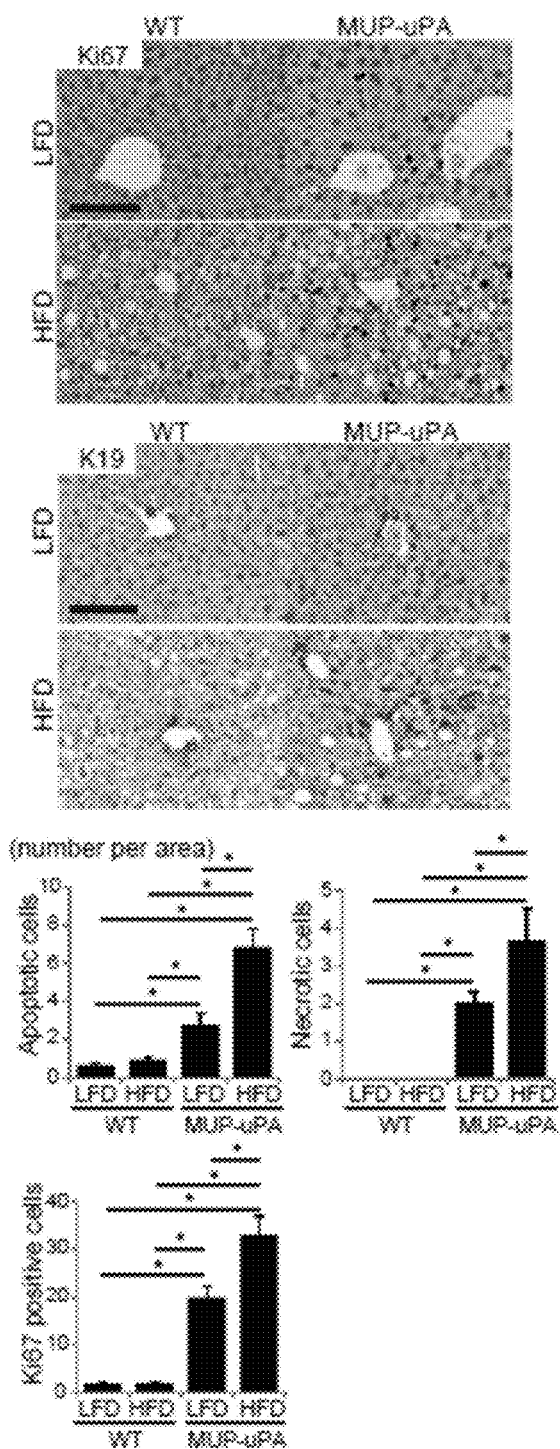
Figure 8F:

Terminal deoxynucleotidyl transferase-mediated dUTP nick-end labeling (TUNEL) staining showed that both apoptotic (nuclear fragmentation) and necrotic (diffuse cytoplasmic staining) cell death were significantly increased in HFD-fed MUP-uPA livers and as a result, the numbers of Ki67-positive proliferating hepatocytes and K19-positive cells were also elevated (FIG. 1D). Expression of cyclin D1 was also increased (FIG. 8F). Thus, HFD-fed MUP-uPA mice exhibit continuous hepatocyte death and compensatory proliferation, a critical process in hepatocarcinogenesis (Maeda et al., 2005).

Figure 2A:
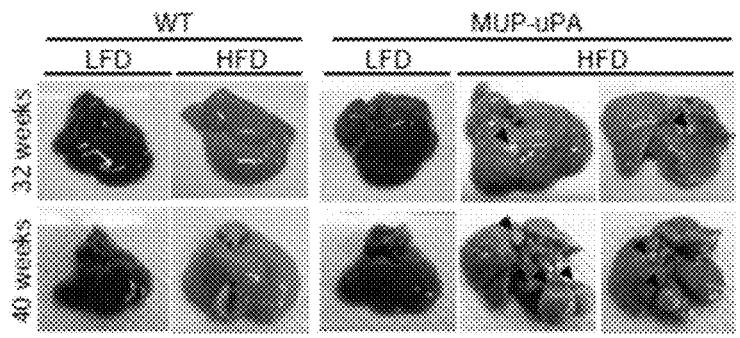
FIGS. 2A-2B are pictorial diagrams showing NASH to HCC progression in MUP-uPA mice.
Figure 2B:
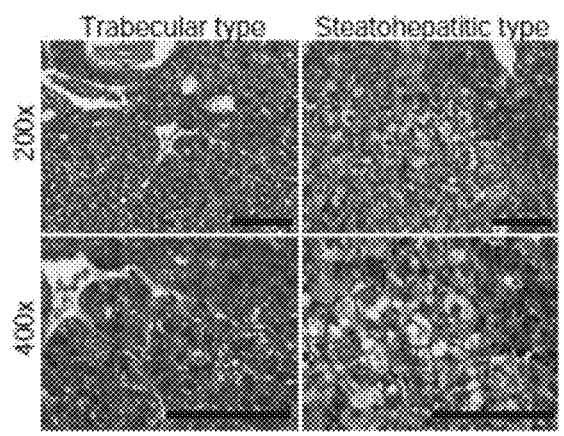
Figure 9A:
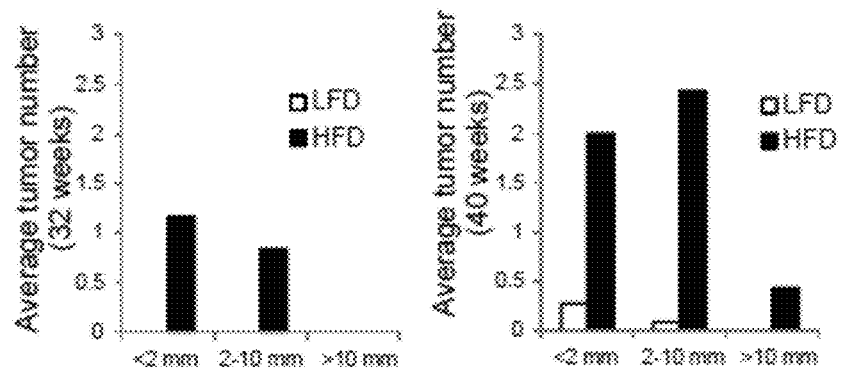
Figure 9E:
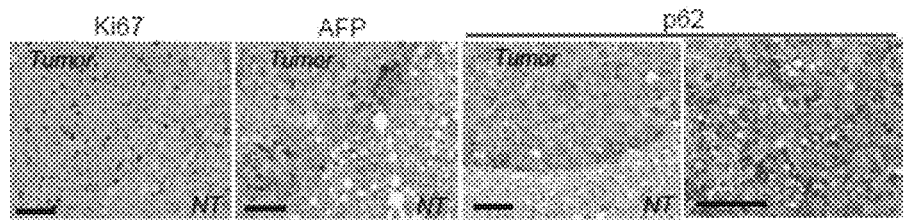
Figure 9F:
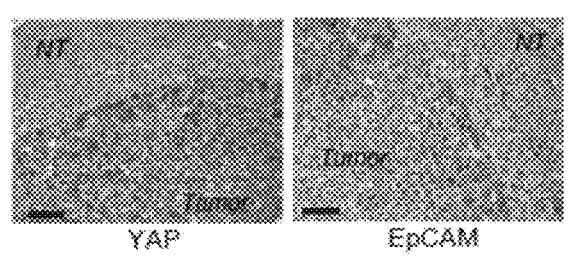
Figure 9G:
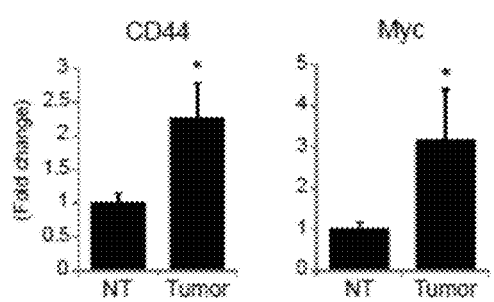
Figure 9H:
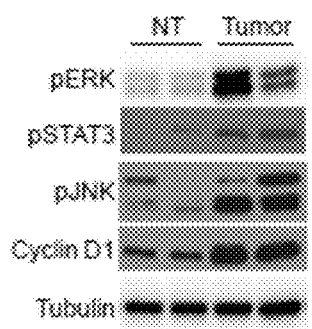
Figure 9I:
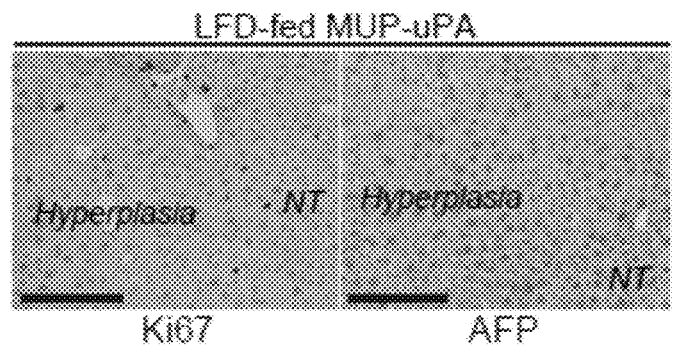
Figure 9J:
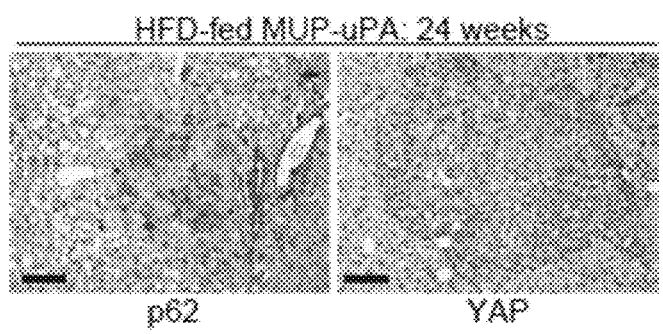

HFD-fed MUP-uPA mice developed small tumors on the liver surface by 32 weeks of age, and large tumors at 40 weeks (FIGS. 2A, 9A, and 9B), when 78.6% (11/14 mice) of HFD-fed MUP-uPA mice had tumors larger than 2 mm, and 35.7% (5/14 mice) had tumors larger than 10 mm. Histologically, 30% of tumors larger than 2 mm were HCCs, similar to human steatohepatitic HCC, a histotype describing NASH-related HCC with ballooning cancer cells and inflammatory cell infiltration (Salomao et al., 2012), but some displayed a classical thick trabecular pattern, whereas the remaining 70% were either typical or steatohepatic adenomas (FIGS. 2B, 9C, and 9D). Cancer cells were highly proliferative and frequently positive for α fetoprotein (AFP) with marked p62 aggregation (FIG. 9E), a sign of impaired autophagy frequently observed in human HCC (Inami et al., 2011). Several oncogenic mediators, e.g., ERK, STAT3, and JNK, as well as cyclin D1, the liver oncogenes YAP and Myc, and the cancer stem cell markers EpCAM and CD44, were activated or upregulated (FIGS. 9F-9H). By contrast, 30% LFD-fed MUP-uPA mice displayed a few tiny nodules in the liver even at 40 weeks of age, corresponding to simple hyperplasia (FIG. 9C). Although 1 of 11 LFD-fed MUP-uPA mice developed a small 3 mm tumor, it was also classified as hyperplasia, which is not proliferative and AFP negative (FIGS. 9C and 9I). In WT mice, neither LFD nor HFD induced any liver tumors by 40 weeks. Of note, HFD-fed MUP-uPA mice showed microscopically visible foci of p62- and YAP-positive cells already at 24 weeks (FIG. 9J). These foci may contain progenitors to the tumors detected at 32-40 weeks. Thus, HFD feeding of MUP-uPA mice induced complete NASH-like pathological features with continuous hepatocyte death and compensatory proliferation, and eventually led to spontaneous HCC and adenoma development that were not seen in LFD-maintained mice.

Example 3

ER Stress Enhances Lipogenesis and Aggravates Steatohepatitis

Figure 3A:
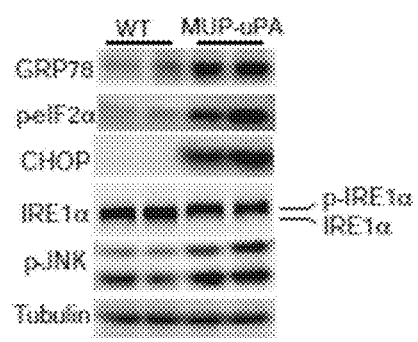
FIGS. 3A-3I are pictorial and graphical diagrams showing that ER stress enhances lipogenesis and promotes steatohepatitis.
Figure 3B:
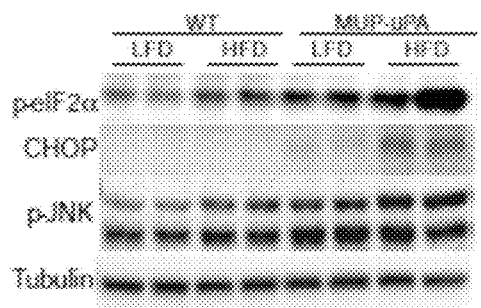
Figure 3C:
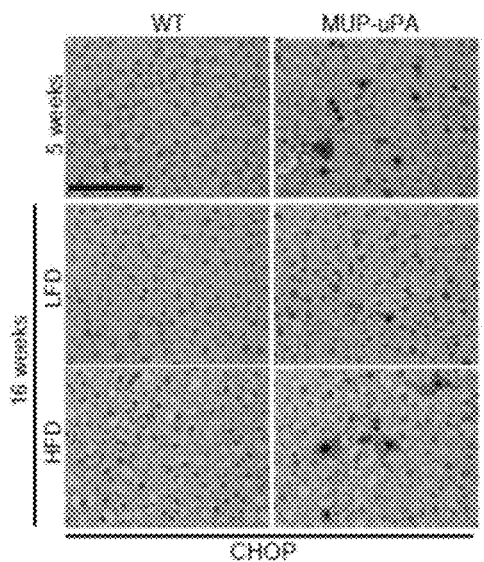
Figure 10A:
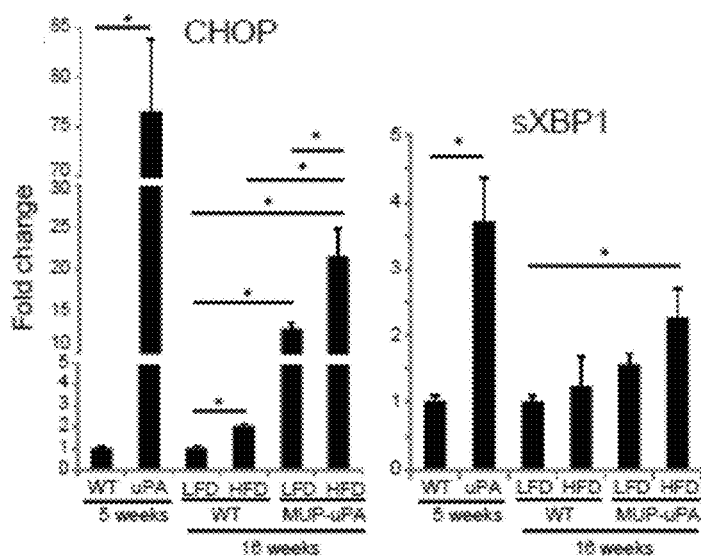
FIGS. 10A-10J are pictorial and graphical diagrams showing that ER stress is sustained by HFD in MUP-uPA mice.
Figure 10B:
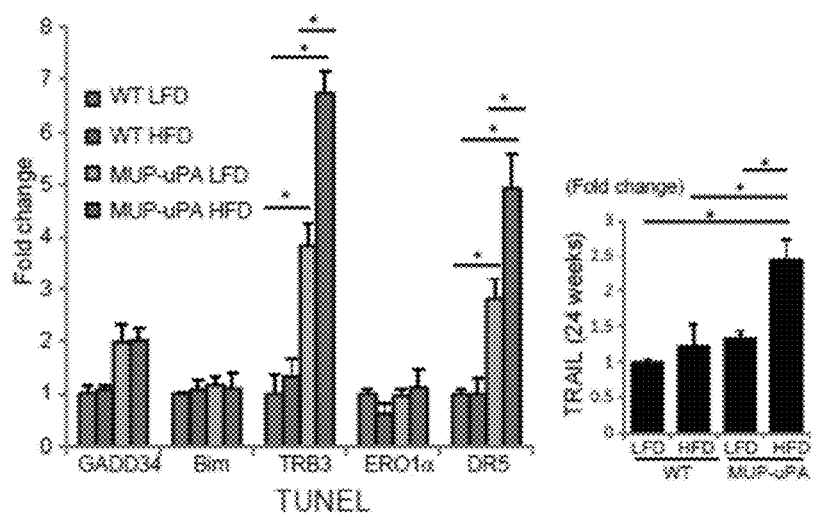
Figure 10C:
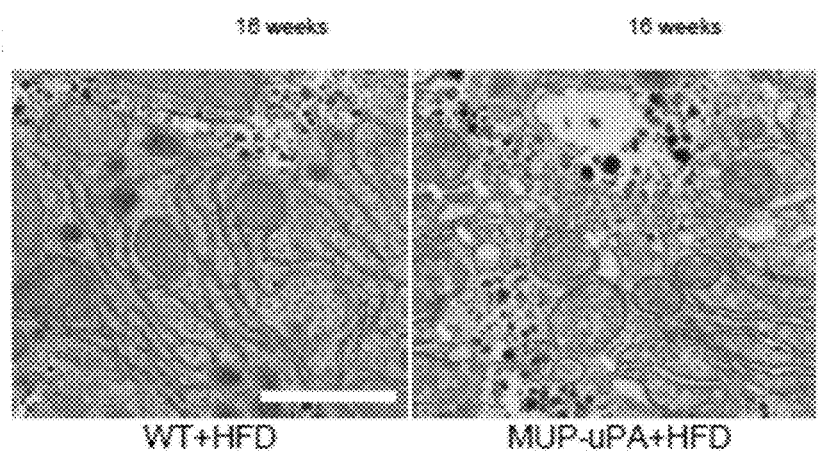
Figure 10D:
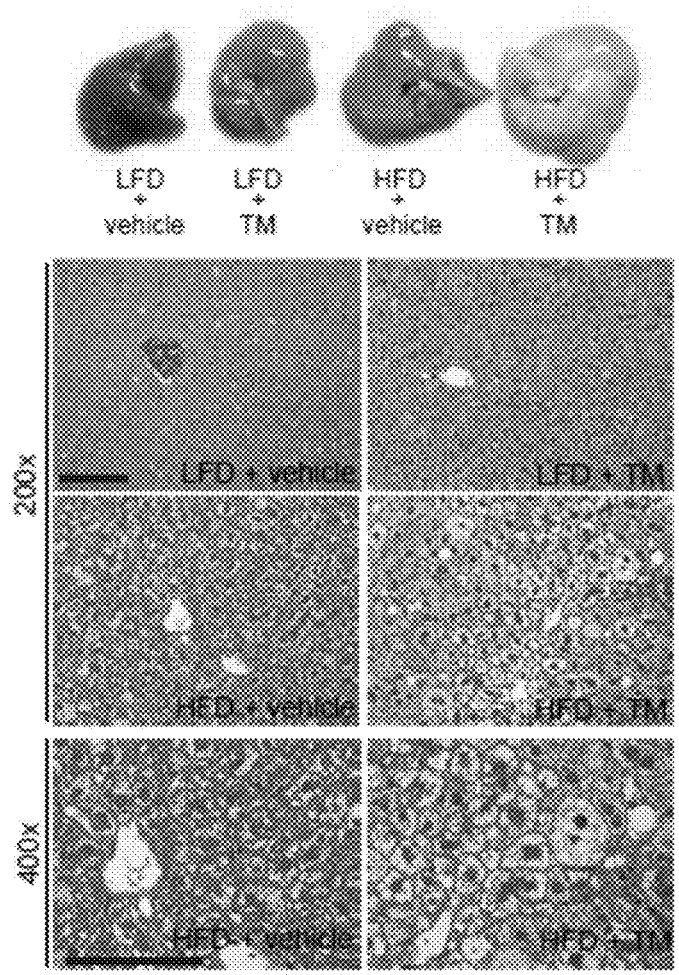
Figure 10E:
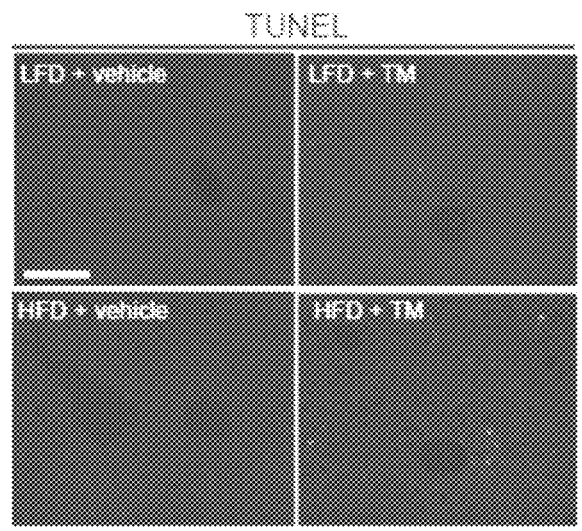
Figure 10F:
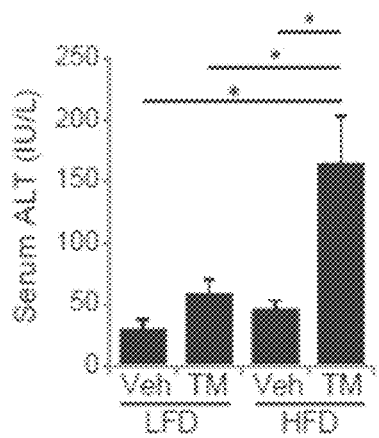

Although the mechanism responsible for hepatocyte death in young MUP-uPA mice is not entirely clear, their hepatocytes are ER stressed (Sandgren et al., 1991). Indeed, several ER stress markers, including CHOP, GRP78, spliced XBP1 (sXBP1), phosphorylated (p) eIF2α, p-IRE1α and p-JNK, were elevated in 5 weeks old MUP-uPA mice compared with WT (FIGS. 3A and 10A). While most markers declined in 16 week old MUP-uPA mice, paralleling the decline in uPA expression, HFD-fed MUP-uPA mice maintained strong eIF2α and JNK phosphorylation and CHOP expression, (FIGS. 3B and 10A). In WT mice, HFD feeding induced only a slight elevation in p-eIF2α and CHOP mRNA with no effect on CHOP protein (FIG. 3B). Immunohistochemistry (IHC) confirmed nuclear CHOP in hepatocytes of 5 weeks old MUP-uPA mice, which was sustained at 16 weeks of age only in HFD-fed MUP-uPA mice (FIG. 3C). TRB3 and DR5, two molecules capable of inducing cell death, were highly upregulated in MUP-uPA mice, especially after HFD feeding (FIG. 10B). After 24 weeks of HFD, expression of the DR5 ligand TRAIL was also elevated in the MUP-uPA liver. Electron microscopy revealed distended and dilated ER in HFD-fed MUP-uPA mice (FIG. 10C). Thus, whereas ER stress appears to be induced by uPA expression in 5 weeks old MUP-uPA mice, it declines due to transgene extinction. However, feeding these mice with HFD rekindles the stress response and induces several cell death mediators that are not expressed in HFD-fed WT mice. To determine whether ER stress can cause ballooning degeneration and hepatocyte death, we injected HFD-fed WT mice with the protein glycosylation inhibitor and ER stress elicitor tunicamycin. This treatment led to rapid (36 hrs) induction of ballooning degeneration, hepatocyte apoptosis and ALT release only in HFD-fed mice (FIGS. 10D-10F). The white appearance of the liver from HFD-fed mice treated with tunicamycin suggested that the liver had become more steatotic.

Figure 3D:
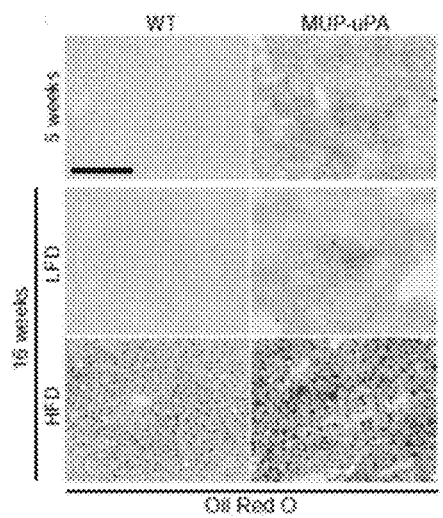
Figure 3E:
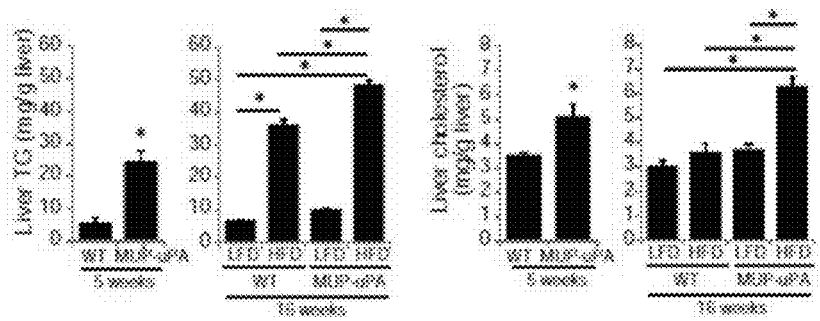
Figure 3F:
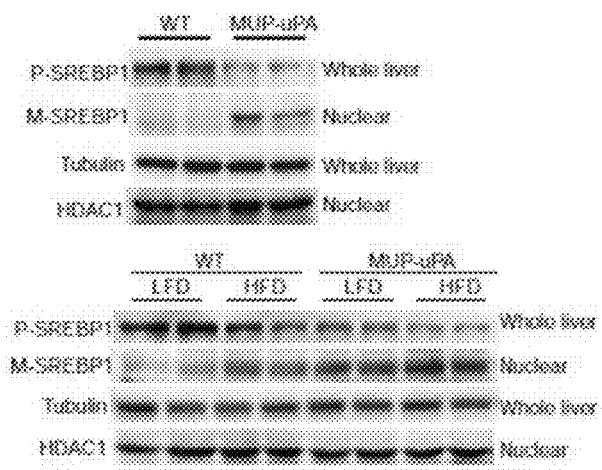
Figure 3G:
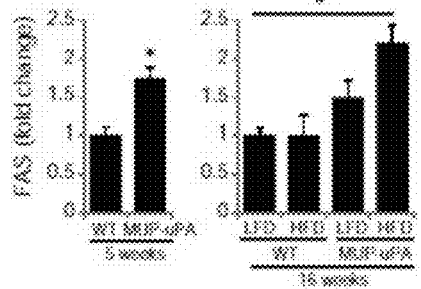
Figure 3H:
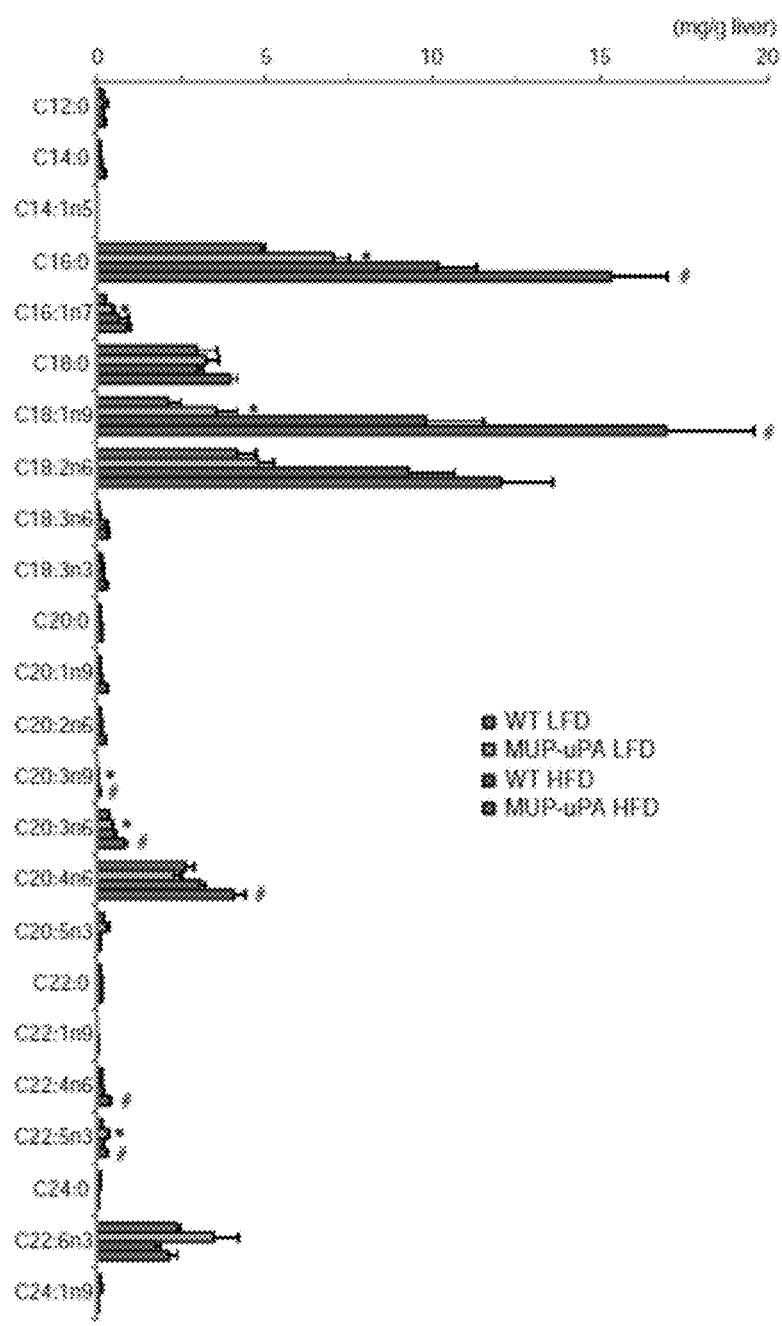
Figure 3I:
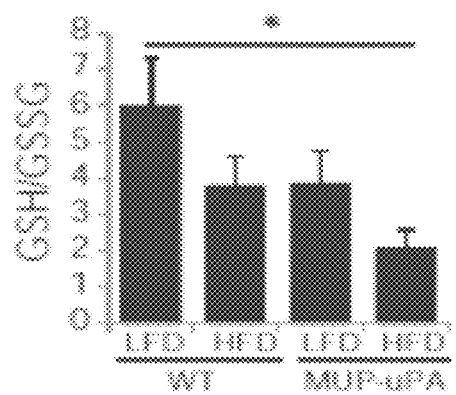
Figure 10G:
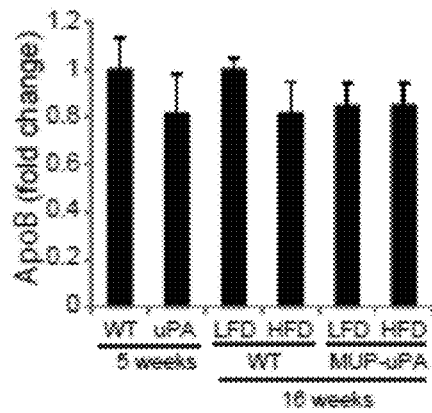
Figure 10H:
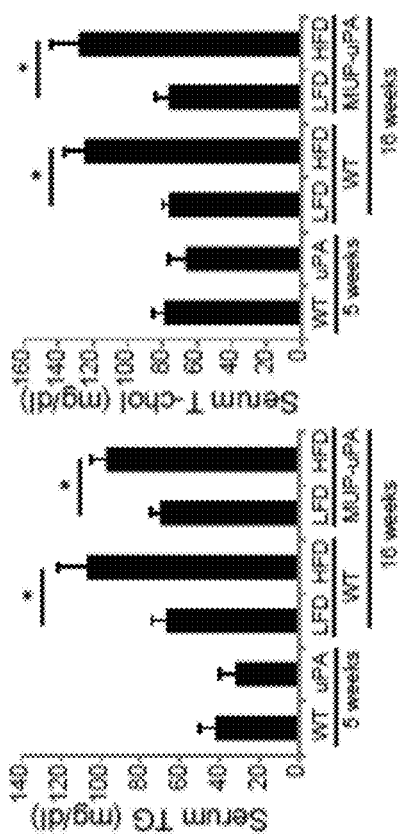
Figure 10I:
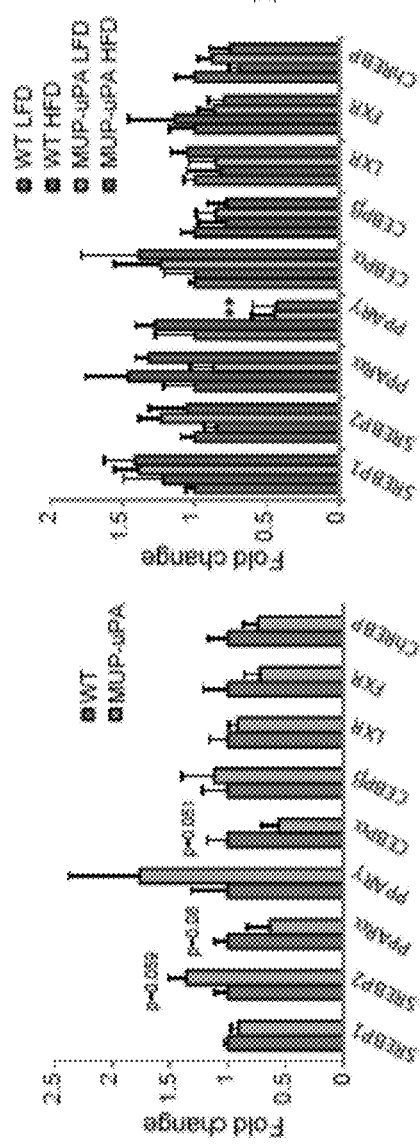

The above results are consistent with the ability of ER stress to cause liver steatosis (Rutkowski et al., 2008). Indeed, Oil Red O (ORO) staining showed mild spontaneous lipid accumulation in 5 weeks old MUP-uPA mice, that was diminished by 16 weeks of age under LFD (FIG. 3D). However, HFD feeding induced more extensive lipid accumulation in MUP-uPA than in WT mice. Liver triglycerides (TG) and cholesterol were also elevated (FIG. 3E). Decreased liver lipid export due to suppression of apoB expression/secretion and increased lipogenesis were suggested to be involved in ER stress-induced steatosis (Ota et al., 2008; Qiu et al., 2011; Rutkowski et al., 2008). Since apoB carries TG and cholesterol from the liver elsewhere, we examined serum TG and cholesterol and liver apoB mRNA. There were no differences in apoB mRNA between the four groups (FIG. 10G) and serum TG and total cholesterol were similarly elevated in HFD-fed WT and MUP-uPA mice (FIG. 10H), suggesting that liver lipid export was not fully impaired in MUP-uPA mice. Next, we examined mRNAs of lipogenic regulators. Although SREBP2 mRNA was slightly increased and PPARα and c/EBPα mRNAs were slightly decreased in 5 weeks old MUP-uPA mice compared with WT mice, these trends were not seen in 16 weeks old mice (FIG. 10I). Expression of PPARγ was decreased in 16 weeks old MUP-uPA mice, but not in 5 weeks old mice. Therefore, enhanced lipogenesis in MUP-uPA mice could not be explained by differential expression of these molecules. However, among lipogenic regulators, SREBP1 is controlled not only by synthesis but also by cleavage and subsequent nuclear translocation (Goldstein et al., 2006), which are stimulated by ER stress (Kammoun et al., 2009). Indeed, SREBP1 precursor abundance was decreased in 5 weeks old MUP-uPA livers and mature, nuclear SREBP1, was elevated (FIG. 3F). HFD feeding further accelerated SREBP1 processing in MUP-uPA mice, but also induced some SREBP1 processing in WT mice. mRNA expression of the SREBP1 target fatty acid synthase (FAS), was increased in 5 weeks old and HFD-fed MUP-uPA mice (FIG. 3G). Consistent with elevated lipogenesis, gas-chromatography determination of hepatic FA composition revealed a significant increase in C16:0 palmitic acid (PA) and longer chain FA, in MUP-uPA mice compared with WT mice, which was further enhanced by HFD feeding (FIG. 3H). Excess lipid accumulation leads to oxidative stress due to mitochondrial $H_2O_2$ production, which can induce cell death (Anderson et al., 2009). Accordingly, HFD-fed MUP-uPA mice displayed strong dihydroethidium (DHE) staining of hepatocytes and a decrease in liver GSH:GSSG ratio (FIGS. 3I and 3J). Oxidative stress in HFD-fed MUP-uPA mice may contribute to CHOP expression, JNK activation, lipotoxic hepatocyte death and oncogenic mutations.

Figure 10J:
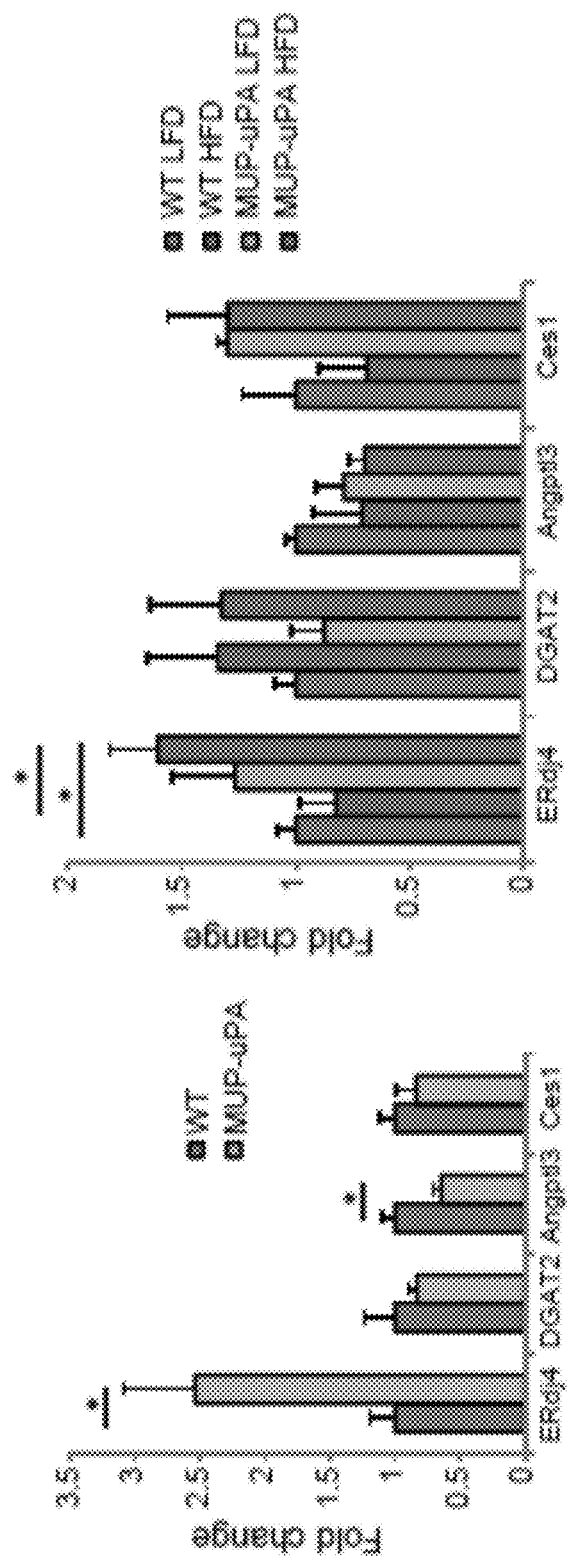

The IRE1α-XBP1 pathway has been reported to regulate hepatic lipid metabolism via XBP1-mediated induction of lipogenic enzymes and regulated IRE1-dependent mRNA decay (RIDD) (Lee et al., 2008; So et al., 2012). Although expression of the XBP1 target gene ERdj4 was unregulated in 5 weeks old and HFD-fed MUP-uPA mice, there were no differences in expression of DGAT2, a lipogenic enzyme regulated by XBP1 but not by SREBP1 (FIG. 10J). RIDD-mediated downregulation of Angptl3 and Ces1 mRNAs can induce hypolipidemia and hepatosteatosis due to decreased lipid secretion from the liver. Although expression of Angptl3 mRNA was decreased in 5 weeks old MUP-uPA mice (FIG. 10J), there were no differences in serum TG and total cholesterol levels between 5 weeks old WT and MUP-uPA mice and Angptl3 mRNA expression recovered in 16 weeks old MUP-uPA mice (FIGS. 10H and 10J). These results suggest that the IRE1α-XBP1 pathway does not play a major role in NASH development in MUP-uPA mice.

Example 4

Figure 4A:
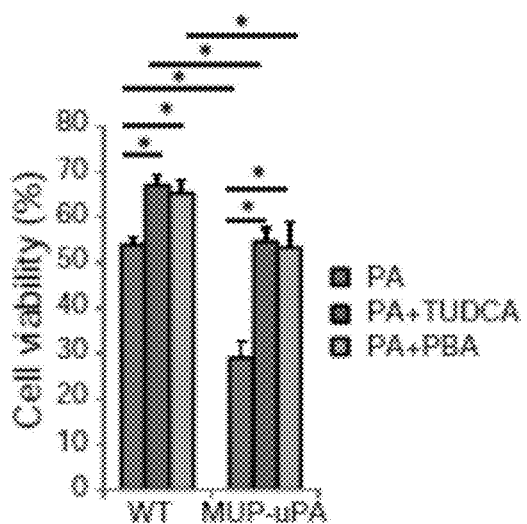
FIGS. 4A-4I are pictorial and graphical diagrams showing that chemical chaperons attenuate lipotoxicity and liver damage in MUP-uPA mice.
Figure 4B:
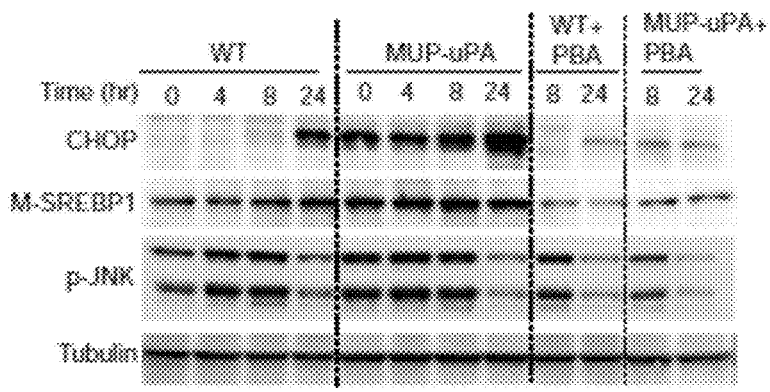
Figure 4C:
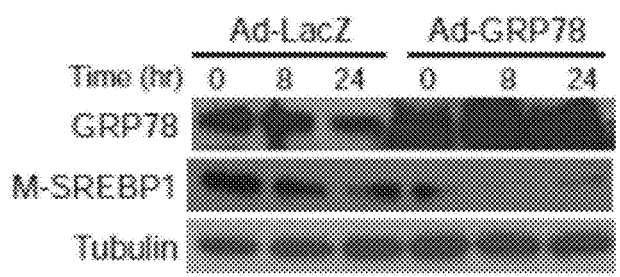
Figure 4D:
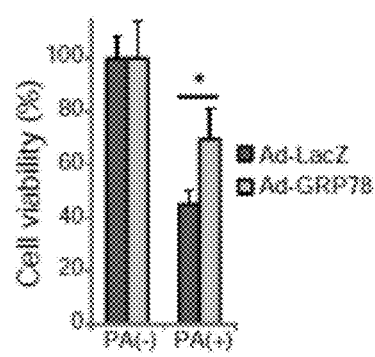
Figure 4E:
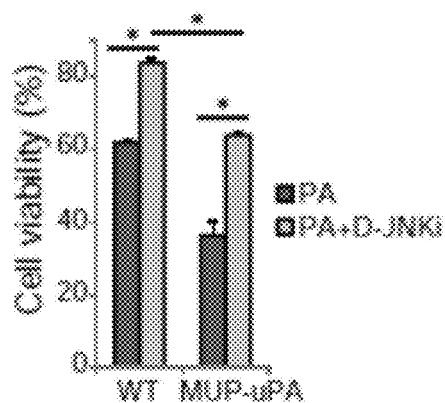

Chemical Chaperons and GRP78 Attenuate Lipotoxicity and Lipogenesis in MUP-uPA Mice To examine whether ER stress enhances lipotoxicity in MUP-uPA hepatocytes, we incubated WT and MUP-uPA hepatocytes with PA. After 24 hrs, lipotoxic cell death was seen in both WT and MUP-uPA hepatocytes, but was more extensive in the latter (FIG. 4A). PA increased CHOP expression and SREBP1 maturation in WT hepatocytes, but these effects were more pronounced in MUP-uPA hepatocytes, which expressed both proteins prior to PA addition (FIG. 4B). To examine the contribution of ER stress to these phenomena, we treated hepatocytes with the chemical chaperons 4-phenylbutyrate (4-PBA) and tauro-ursodeoxycholic acid (TUDCA), which reduce ER stress (Ozcan et al., 2006). Both compounds attenuated PA-induced cell death, but their pro-survival effect was more pronounced in MUP-uPA hepatocytes (FIG. 4A). CHOP induction and SREBP1 maturation upon PA treatment were also reduced by 4-PBA (FIG. 4B). Overexpression of the ER protein chaperon GRP78 in MUP-uPA hepatocytes also inhibited SREBP1 maturation and PA-induced cell death (FIGS. 4C and 4D), further supporting the role of ER stress in both phenomena. PA treatment activated JNK, but consistent with previous results that ER stress has only a partial role in JNK activation by PA (Holzer et al., 2011), the effect was restricted to WT hepatocytes and PBA treatment only partially reduced JNK phosphorylation (FIG. 4B). Nonetheless, the JNK inhibitor D-JNKi protected both cell types from PA induced death (FIG. 4E).

Figure 4F:
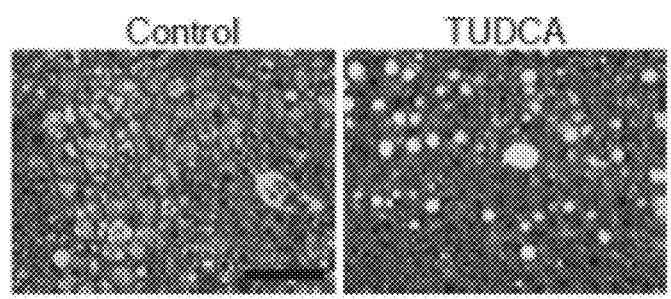
Figure 4G:
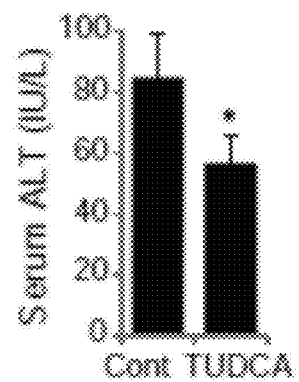
Figure 4H:
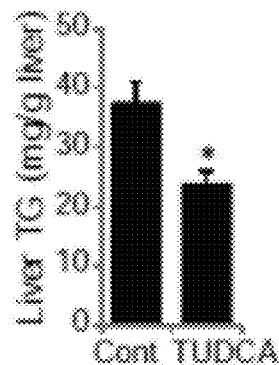
Figure 4I:
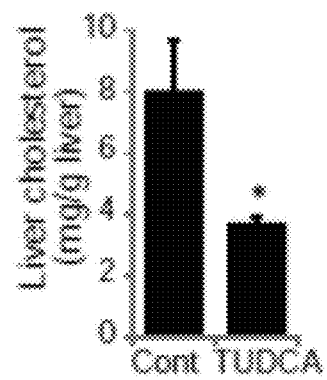
Figure 11A:
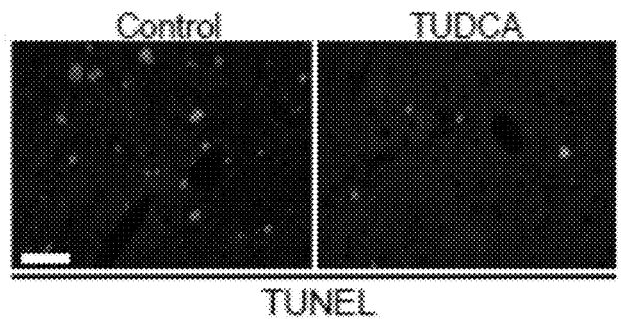
FIGS. 11A-11M are pictorial and graphical diagrams showing the effects of TUDCA and GRP78 overexpression and CHOP ablation on NASH and HCC development.
Figure 11B:
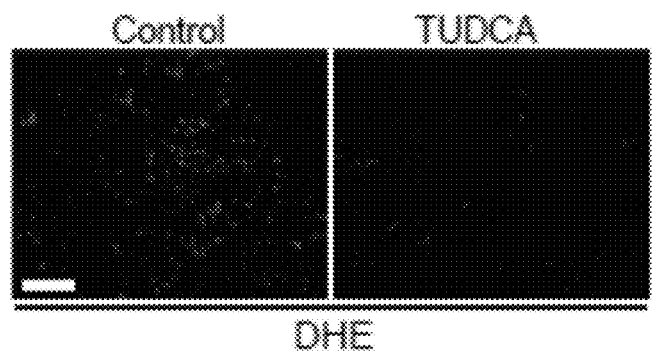
Figure 11C:
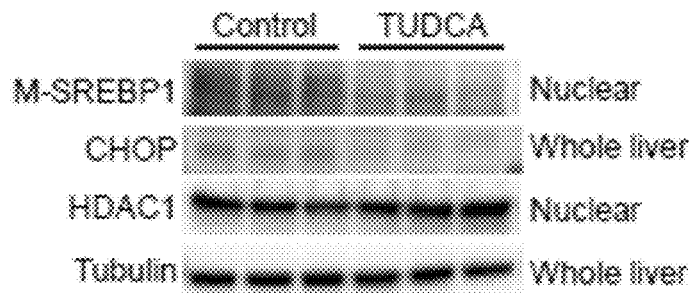
Figure 11D:
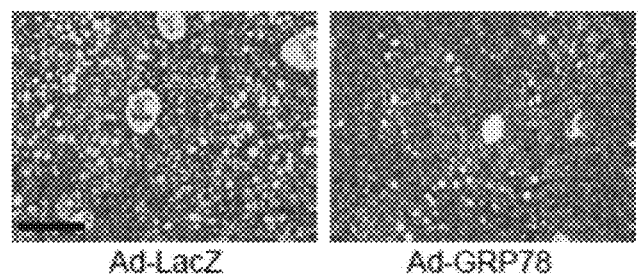
Figure 11E:
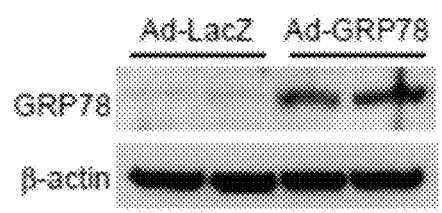

We examined the effect of TUDCA on NASH development. We initiated daily i.p. injections of TUDCA (250 mg/kg) or phosphate-buffered saline (PBS; vehicle control) to HFD-fed MUP-uPA mice at 16 weeks of age. After 4 weeks, hepatosteatosis and hepatocyte ballooning were attenuated (FIG. 4F), and serum ALT and hepatic TG and cholesterol were significantly reduced (FIGS. 4G-4I). Hepatocyte death and ROS accumulation were also suppressed (FIGS. 11A and 11B). TUDCA treatment also inhibited CHOP expression and SREBP1 maturation in livers of HFD-fed MUP-uPA mice (FIG. 11C). We also found that in vivo overexpression of GRP78 using an adenovirus vector attenuated hepatic steatosis in HFD-fed MUP-uPA mice (FIGS. 11D and 11E). However, due to enhanced adenovirus toxicity in MUP-uPA mice we could not assess the effect on NASH and HCC development. Nonetheless, the results suggest that increased lipotoxicity caused by a positively reinforced cycle of ER stress, oxidative stress, and lipogenesis aggravates fatty liver disease in HFD-fed MUP-uPA mice.

Figure 11F:
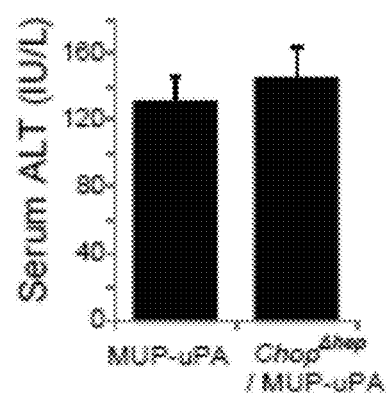
Figure 11G:
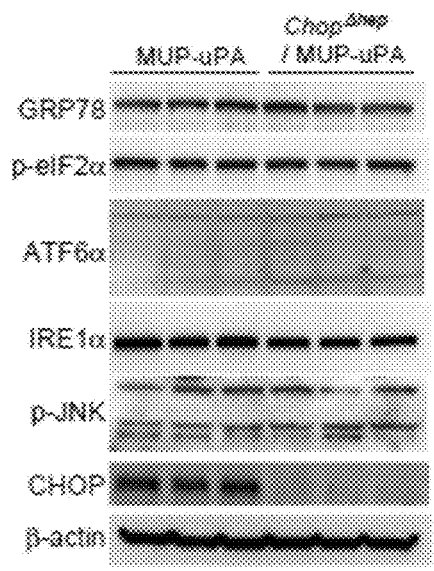
Figure 11H:
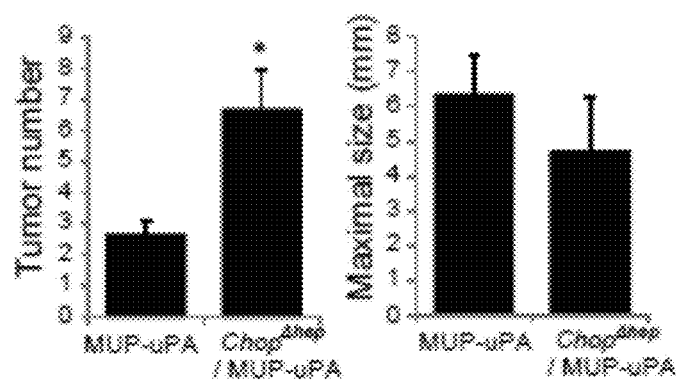
Figure 11I:
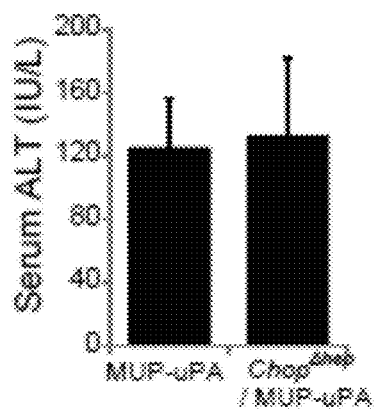
Figure 11J:
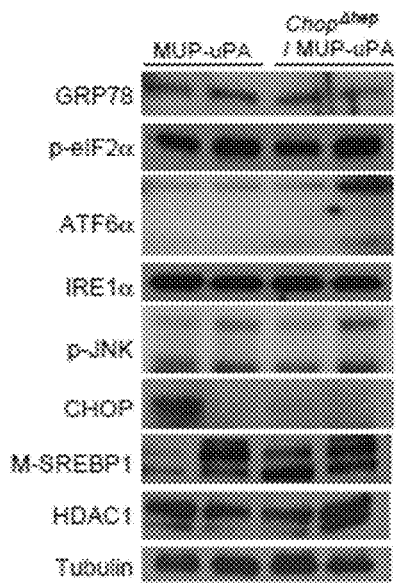
Figure 11K:
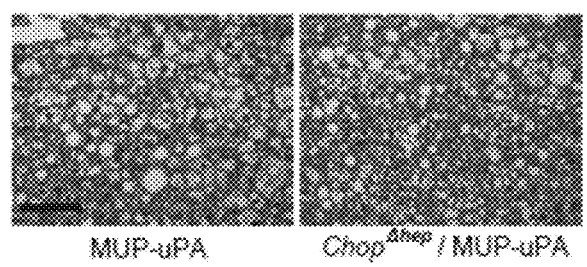
Figure 11L:
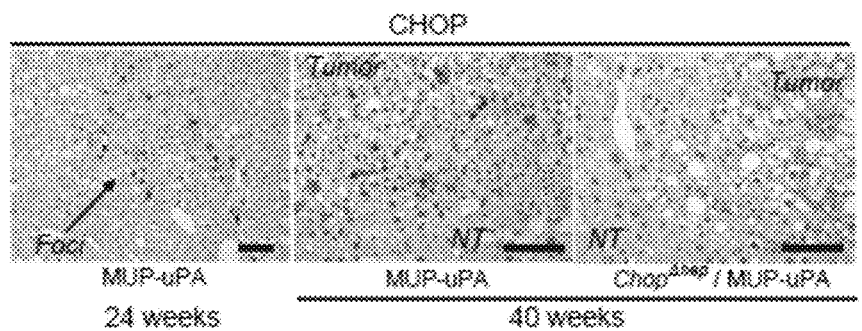
Figure 11M:
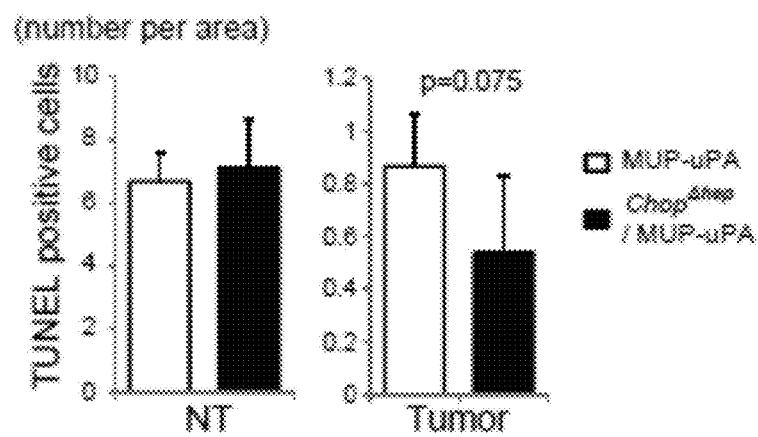

Given the pronounced expression of CHOP in MUP-uPA mice and its postulated role in apoptosis (Malhi and Kaufman, 2011) we crossed MUP-uPA mice to $Chop^{\Delta hep}$ mice in which CHOP was deleted in hepatocytes. Despite efficient CHOP ablation, there was no reduction in liver damage, JNK and eIF2α phosphorylation or GRP78 expression in young $Chop^{\Delta hep}$/MUP-uPA mice (FIGS. 11F and 11G). Correspondingly, CHOP ablation did not inhibit HCC development (FIG. 11H). In fact, CHOP ablation increased tumor multiplicity without affecting tumor size, ER stress markers or NASH severity (FIGS. 11I-11K), results that stand in marked contrast to the protective effect of whole body Chop ablation in DEN-induced hepatocarcinogenesis (DeZwaan-McCabe et al., 2013). CHOP was strongly expressed in some tumors and preneoplastic lesions of HFD-fed MUP-uPA mice but not in $Chop^{\Delta hep}$/MUP-uPA mice, and the number of TUNEL-positive cells tended to be reduced in the tumor tissues of $Chop^{\Delta hep}$/MUP-uPA mice (Figure S4L-M), suggesting that hepatocyte CHOP is not positively involved in NASH progression and HCC development, similar to what was observed in whole body $Chop^{-/-}$ mice on methionine-choline-deficient (MCD) diet (Soon et al., 2010). Nonetheless, CHOP may play a tumor suppressive role by inducing apoptosis of initiated hepatocytes.

Example 5

TNF from Liver Macrophages Promotes Lipogenesis, NASH and HCC Development

Figure 5A:
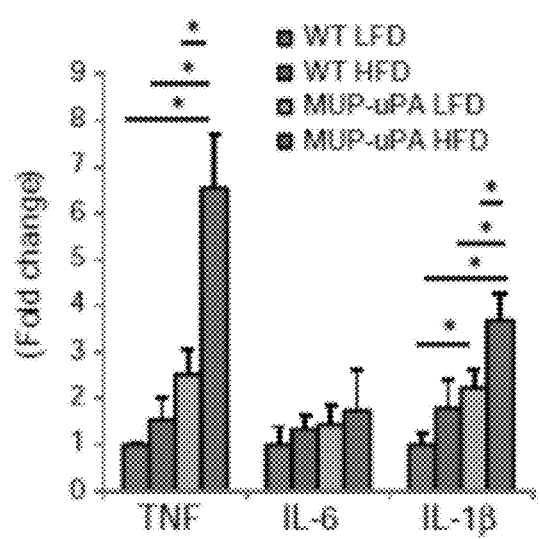
FIGS. 5A-5I are pictorial and graphical diagrams showing that TNFR1 signaling promotes tumor growth.
Figure 5B:
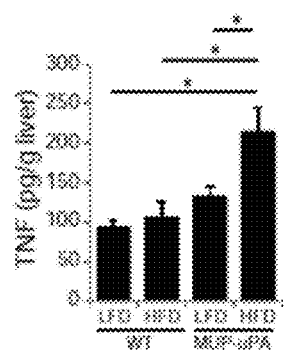
Figure 5C:
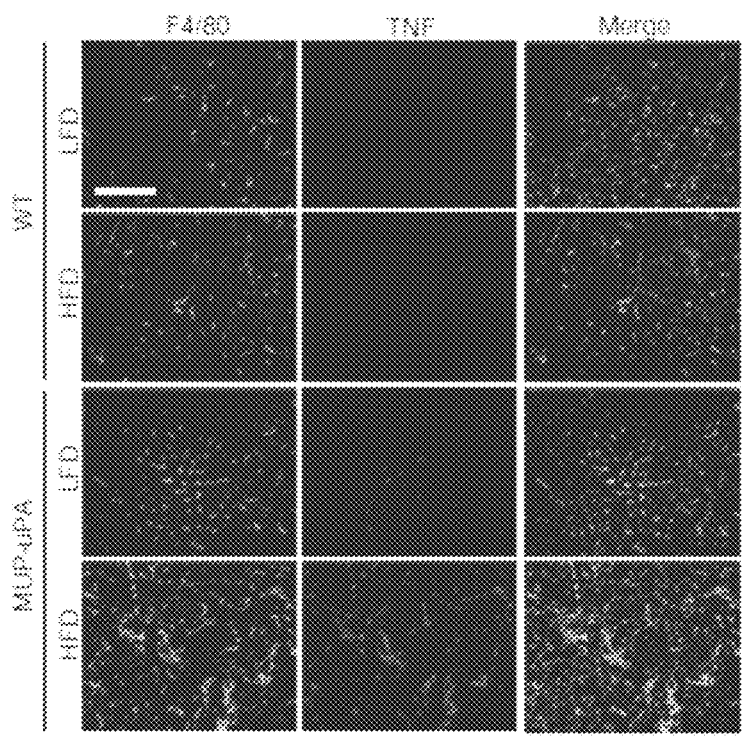
Figure 12A:
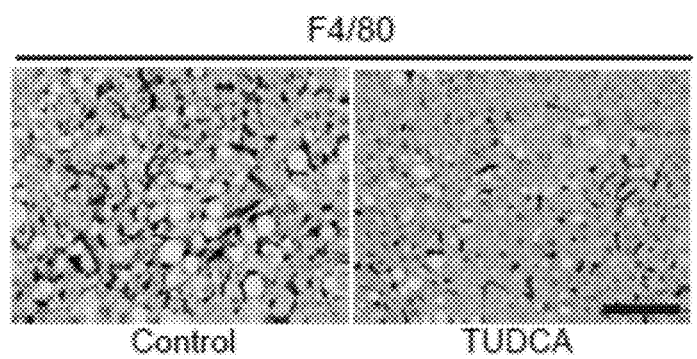
FIGS. 12A-12F are pictorial and graphical diagrams showing characteristics of $Tnfr1^{-/-}$/MUP-uPA mice.
Figure 12B:
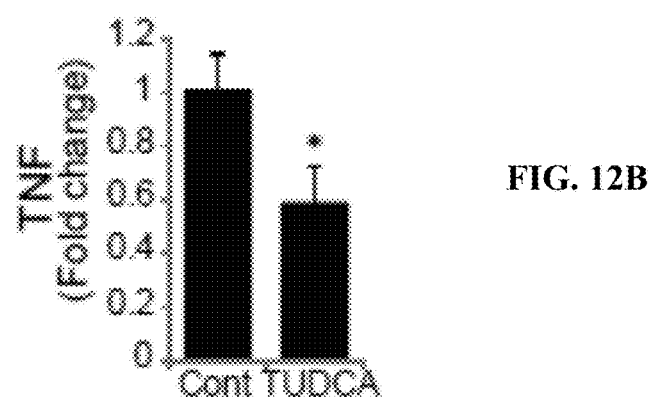
Figure 12C:
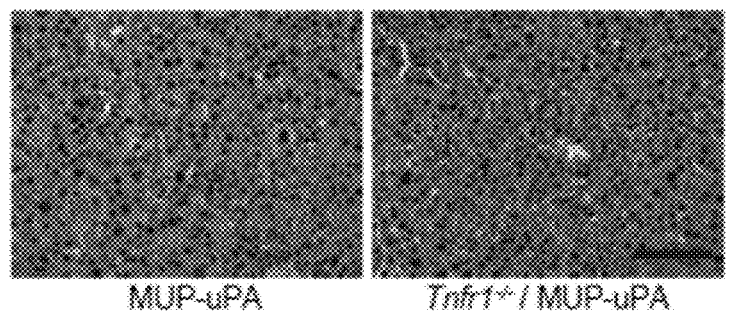
Figure 12D:
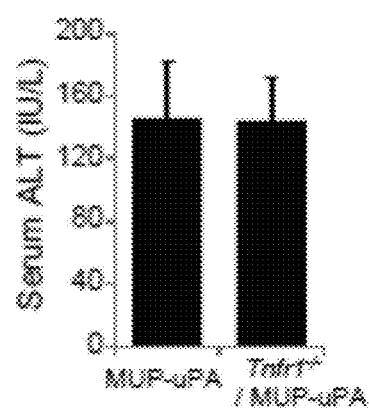
Figure 12E:
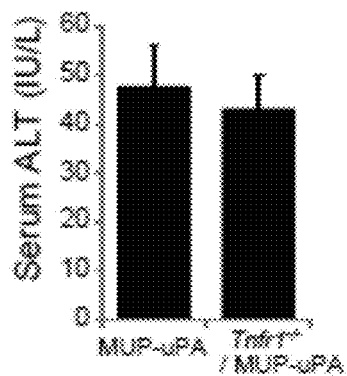
Figure 12F:
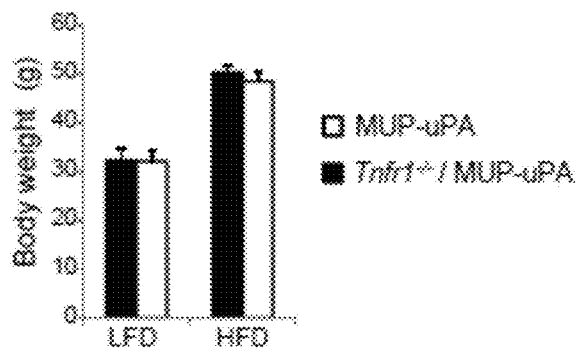

Next, we examined involvement of inflammatory cytokines in hepatosteatosis and steatohepatitis. In 24 weeks old mice, TNF and IL-1β, but not IL-6, mRNAs were elevated in HFD-fed MUP-uPA livers (FIG. 5A). TNF production was confirmed by ELISA (FIG. 5B) and immunofluorescence (IF) analysis localized it to F4/80-positive macrophages, whose number was elevated in HFD-fed MUP-uPA mouse livers (FIG. 5C). The increase in macrophage infiltration and TNF expression was inhibited by TUDCA treatment (FIGS. 12A and 12B), suggesting it is stimulated, in part, by hepatocyte ER and oxidative stress.

Figure 5D:
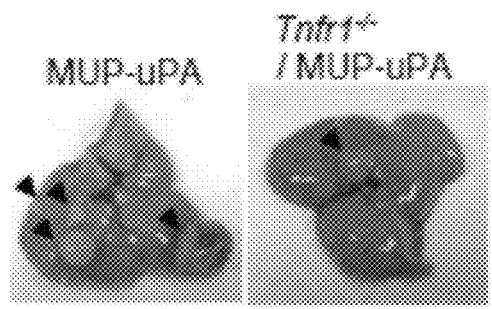
Figure 5E:
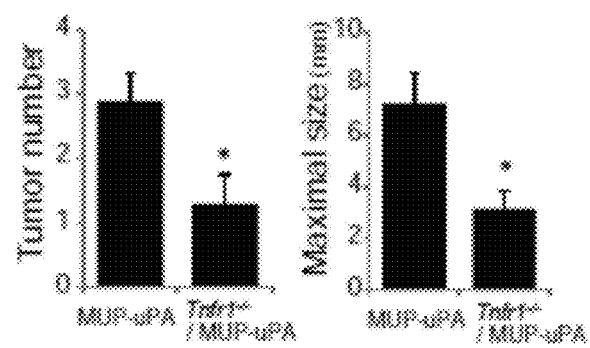
Figure 5F:
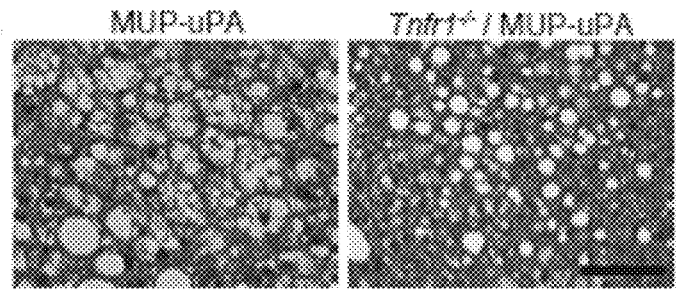
Figure 5G:
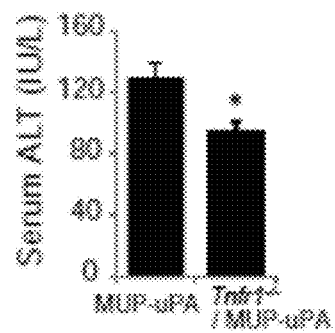
Figure 5H:
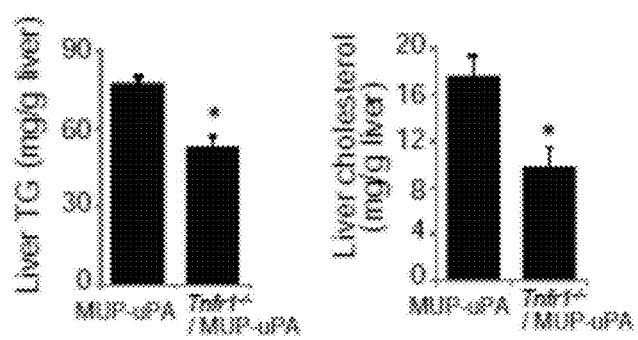
Figure 5I:
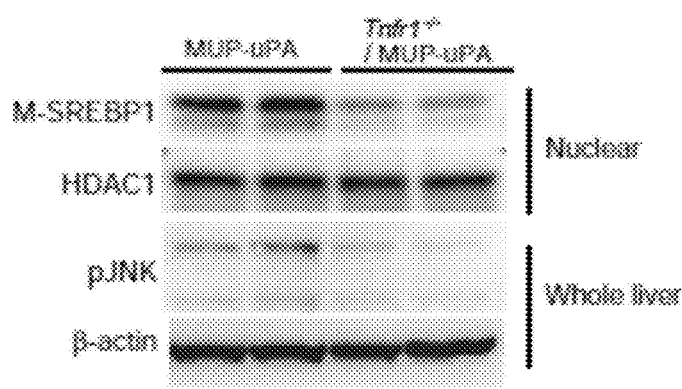

To investigate the role of TNF in NASH progression and HCC development, we generated TNF receptor 1 (TNFR1)-deficient MUP-uPA ($Tnfr1^{-/-}$/MUP-uPA) mice. At 5 and 40 weeks of age, there were no differences in liver injury and body weights between MUP-uPA and $Tnfr1^{-/-}$/MUP-uPA mice (FIGS. 12C-12F). We placed these mice on HFD from 6 to 40 weeks of age, and assessed liver histology and tumorigenesis. Body weight gain at 40 weeks of age was similar between MUP-uPA and $Tnfr1^{-/-}$/MUP-uPA mice (FIG. 12F), but tumor development was substantially reduced upon TNFR1 ablation (FIGS. 5D and 5E). Importantly, hepatocyte ballooning, ALT release, liver TG and cholesterol, as well as SREBP1 and JNK activation, were reduced in $Tnfr1^{-/-}$/MUP-uPA mice (FIGS. 5F-5I). Therefore, TNFR1 signaling perpetuates NASH pathogenesis and HCC progression.

Example 6

TNFR1 Signaling Directly Promotes Tumor Growth

Figure 6A:
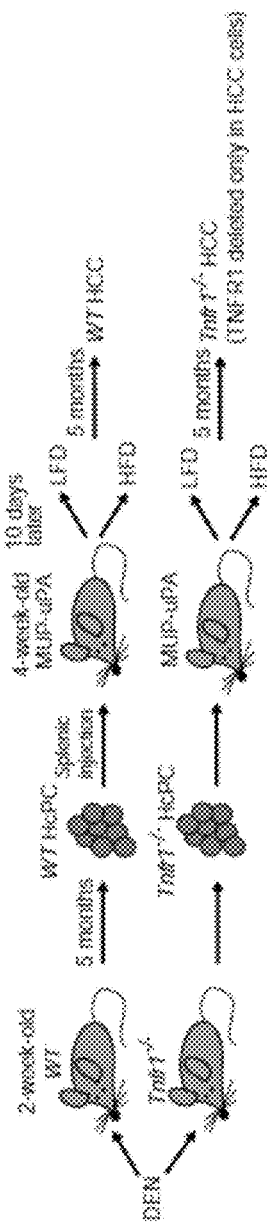
FIGS. 6A-6G are pictorial and graphical diagrams showing that TNFR1 signaling promotes tumor growth.
Figure 6C:
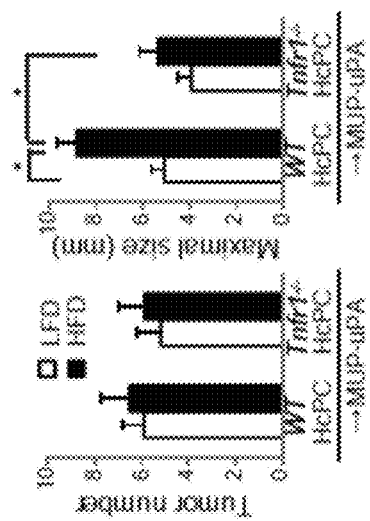
Figure 6B:
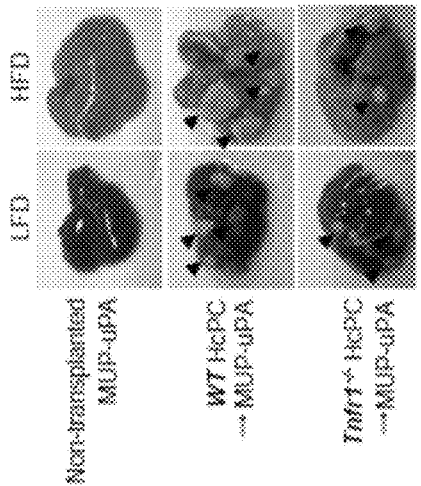
Figure 13A:
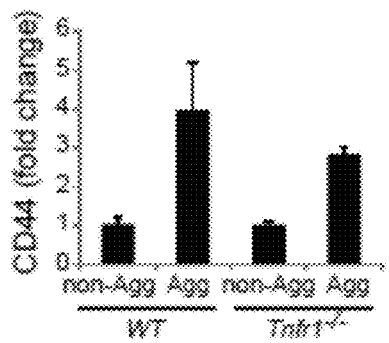
FIGS. 13A-13J are pictorial and graphical diagrams showing analyses of HcPC transplanted MUP-uPA mice.
Figure 13B:
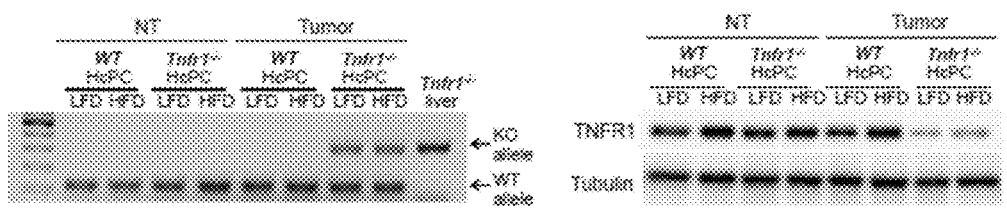
Figure 13C:
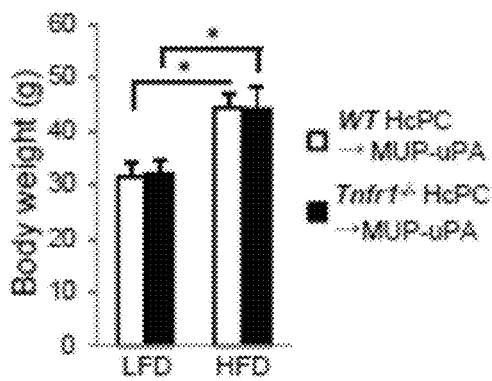
Figure 13D:
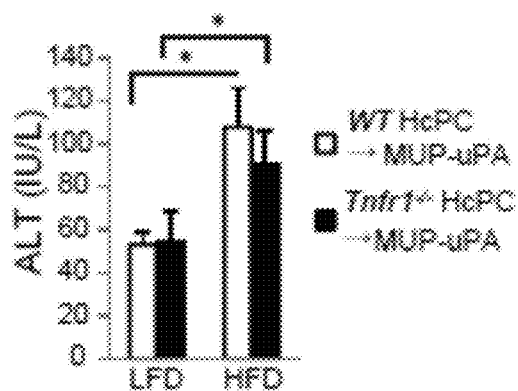
Figure 13E:
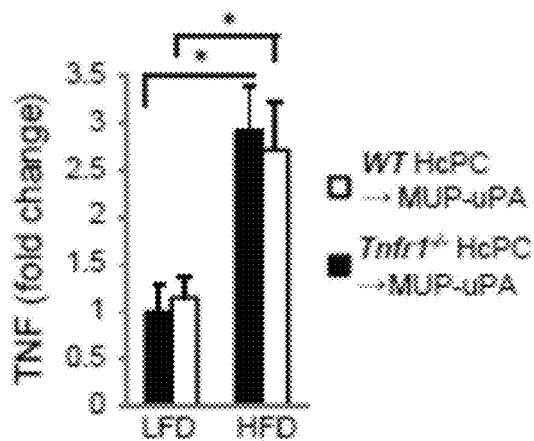
Figure 13F:
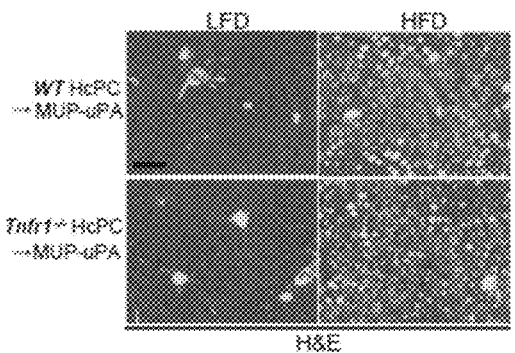
Figure 13G:
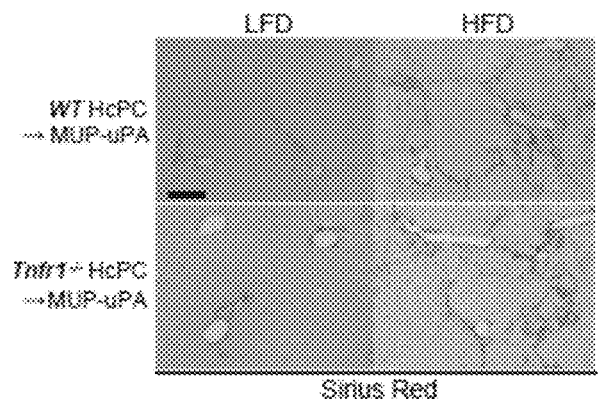
Figure 13H:
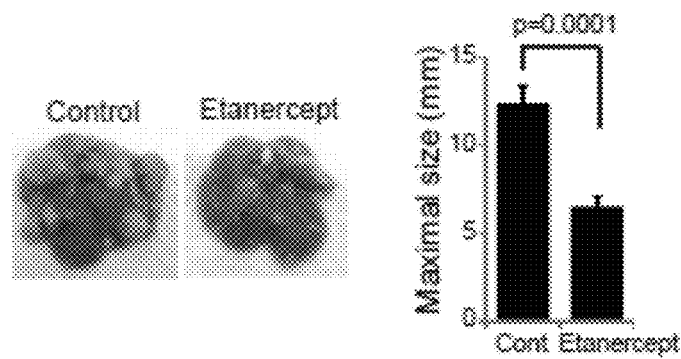
Figure 13I:
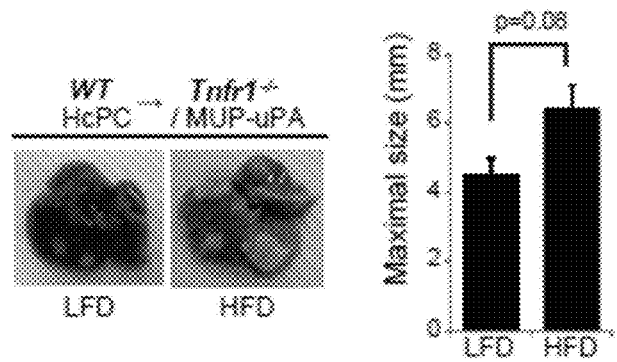

To determine whether TNFR1 signaling promotes HCC development by acting within HCC progenitor cells (HcPC), whose isolation we recently described (He et al., 2013), we transplanted HcPC from DEN-treated WT or $Tnfr1^{-/-}$ mice into MUP-uPA mice, that were placed on LFD or HFD (FIG. 6A). Expression of the HcPC marker CD44 was comparable between WT or $Tnfr1^{-/-}$ HcPC (FIG. 13A). After 5 months, non-transplanted MUP-uPA mice did not have any tumors larger than 2 mm, even after HFD feeding, whereas HcPC-transplanted mice developed multiple HCC nodules (FIG. 6B). HFD feeding did not affect tumor number (which is determined by the number of transplanted HcPC), but significantly increased tumor size in mice transplanted with WT HcPC, but not in mice receiving $Tnfr1^{-/-}$ HcPC (FIGS. 6B and 6C). Thus, although TNFR1 signaling is dispensable for HcPC induction by DEN it strongly stimulates tumor growth in a cell autonomous manner. Control experiments confirmed that TNFR1 was deleted in HCC cells but not in non-tumor liver tissues (FIG. 13B). In addition, there were no differences in NASH-like pathology and TNF expression in the background liver harboring either WT or $Tnfr1^{-/-}$ HcPC (FIGS. 13C-13G). To further investigate the role of TNF signaling in these effects, we treated WT HcPCs-transplanted MUP-uPA mice with the TNF antagonist etanercept under HFD feeding. Etanercept treatment significantly suppressed HCC growth (FIG. 13H). We also transplanted WT HcPC into $Tnfr1^{-/-}$/MUP-uPA hosts and found that HFD still led to increased tumor size, albeit to a lower extent than the 2-fold effect seen in MUP-uPA hosts (FIG. 13I).

Figure 6D:
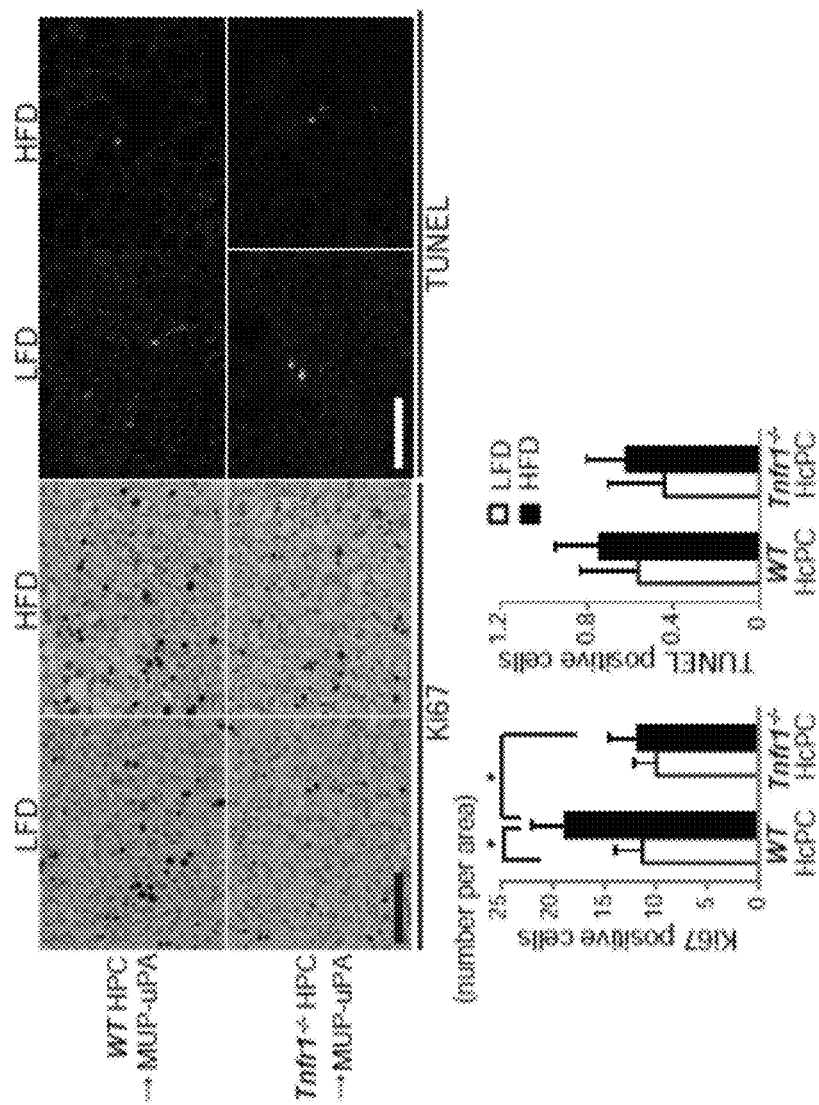
Figure 6E:
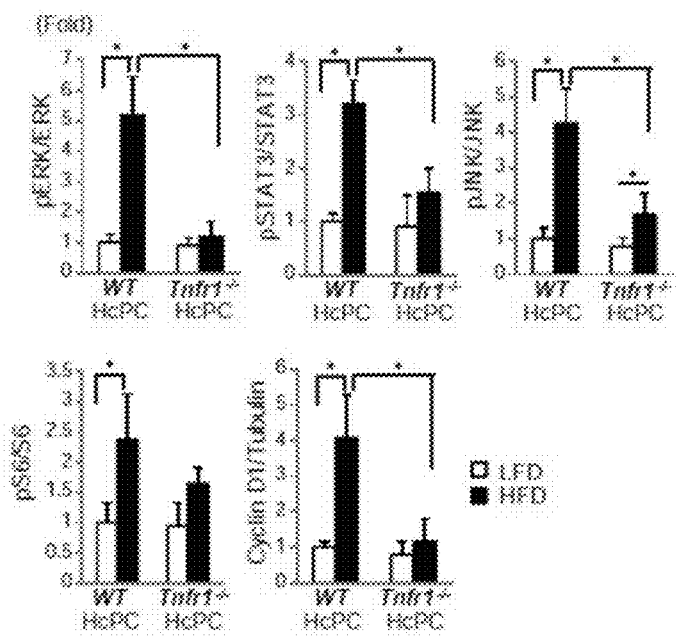
Figure 6F:
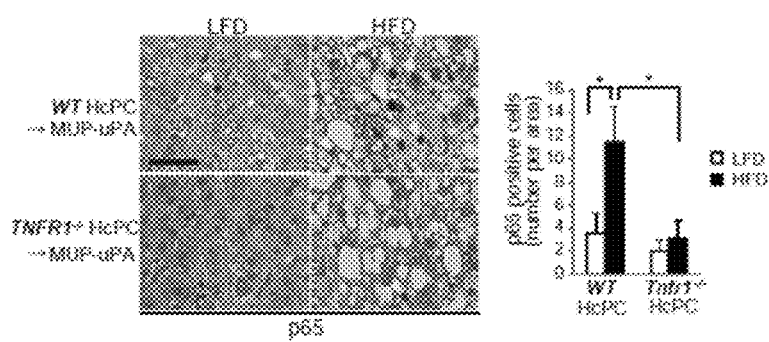
Figure 6G:
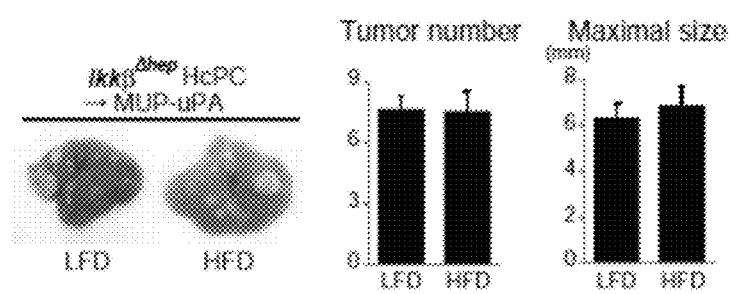
Figure 13J:
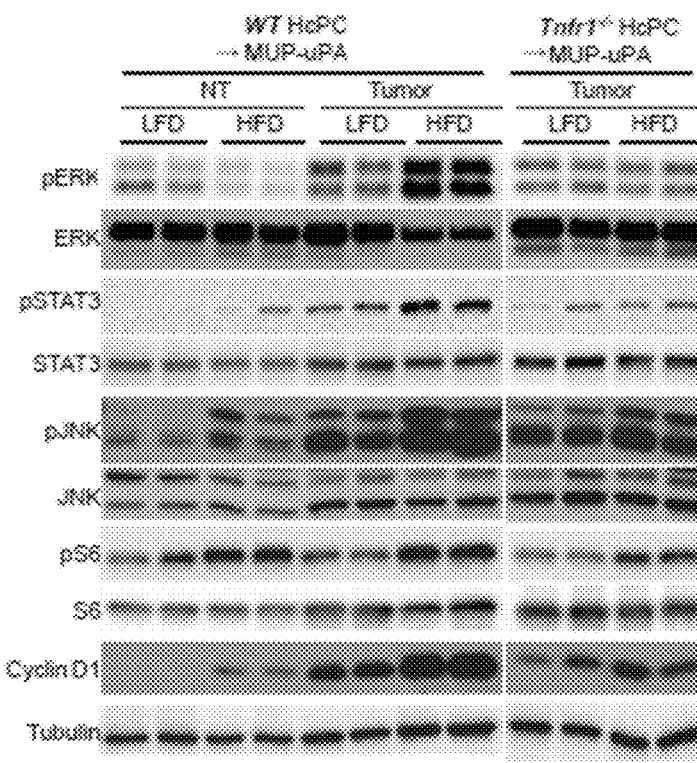

We assessed cell proliferation and apoptosis in HcPC-derived tumors. While no significant effects on apoptosis were observed, HFD enhanced cell proliferation in tumors formed by WT HcPC and this effect was diminished upon TNFR1 ablation (FIG. 6D). Cyclin D1 expression and phosphorylation of ERK, STAT3, JNK, and S6 were enhanced by HFD feeding in WT HcPCs derived tumors (FIGS. 6E and 13J). Apart from S6 phosphorylation, these responses were abolished upon TNFR1 ablation. TNFR1 in HcPC was also required for NF-κB activation in tumors that developed in HFD-fed MUP-uPA mice (FIG. 6F) and IKKβ ablation in HcPC prevented HFD-enhanced tumor growth (FIG. 6G). Thus the TNF-TNFR1-IKKβ-NF-κB pathway is an important mediator of HCC growth in HFD-fed mice.

Example 7

TNFR1 Signaling Promotes Tumor-Associated Inflammation

Figure 7A:
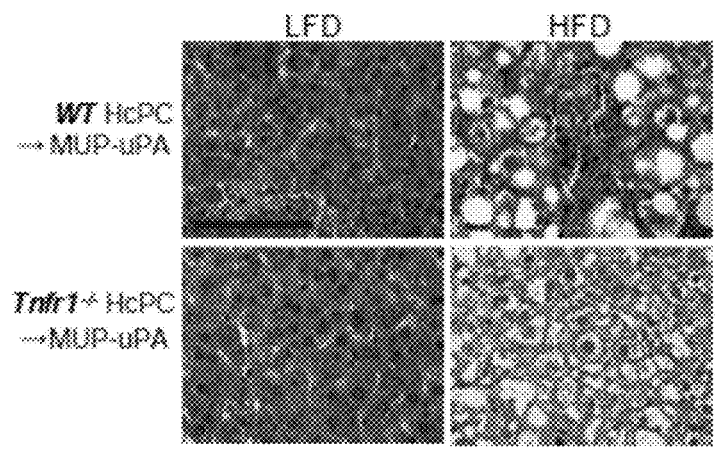
FIGS. 7A-7D are pictorial and graphical diagrams showing that TNFR1 signaling in cancer cells promotes tumor-elicited inflammation.
Figure 7B:
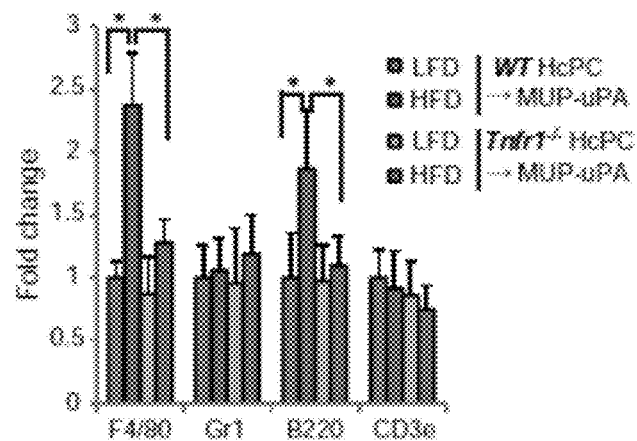
Figure 7C:
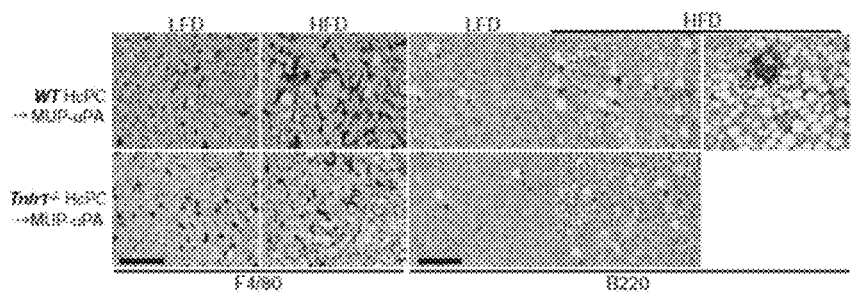
Figure 7D:
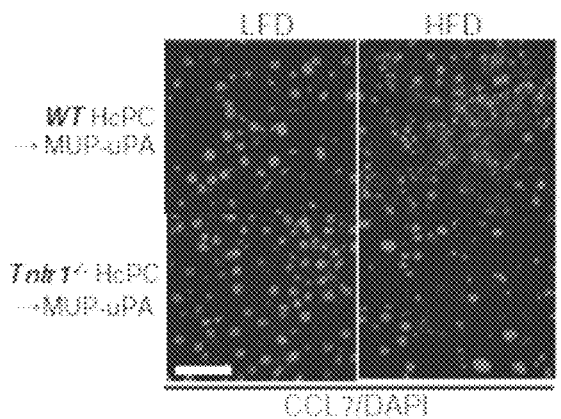
Figure 14:
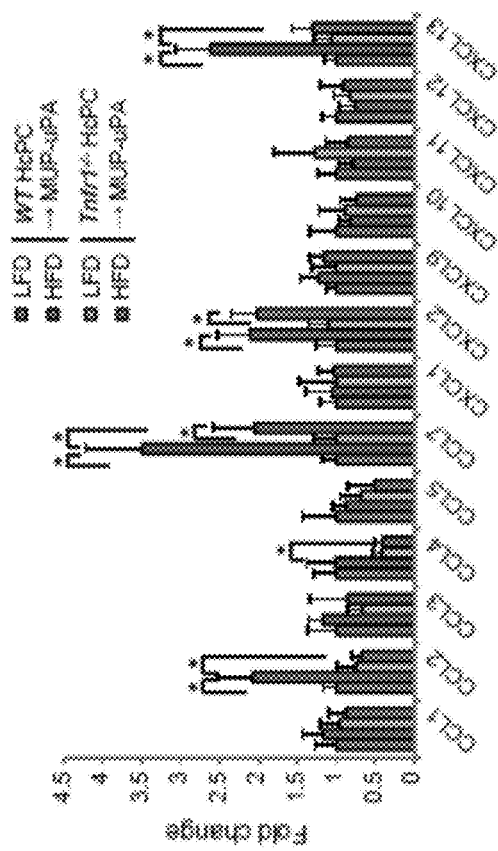
FIG. 14 is a graphical diagram showing expression of inflammatory cytokines and chemokines in tumor tissues. Relative mRNA amounts of inflammatory cytokines and chemokines in HCC tissues from MUP-uPA mice transplanted with either WT or Tnfr1$^{-/-}$ HcPC and kept on LFD or HFD were determined by real-time Q-PCR. (n=5 per group). *p<0.05. Results are shown as means±S.D.
Figure 14:
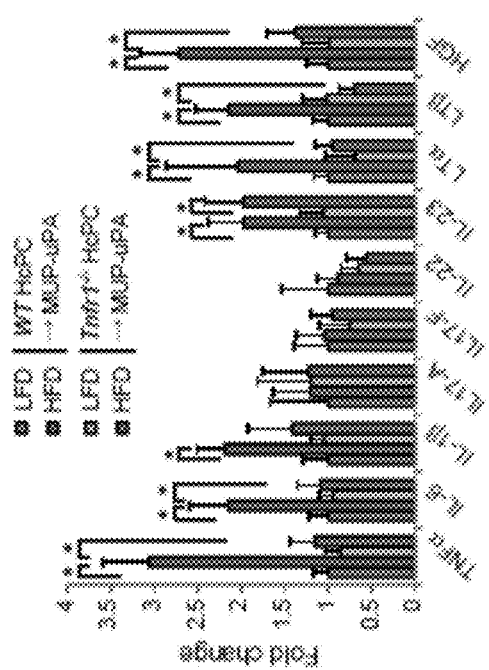

Some of the signaling effectors that are activated in HFD-fed mice are not directly regulated by TNFR1. We postulated that autocrine or paracrine signaling may mediate some of the observed responses and analyzed tumors generated by WT and Tnfr1$^{-/-}$ HcPC more closely. In HFD-fed mice, both WT and Tnfr1$^{-/-}$ HCCs were composed of steatotic cells, but immune infiltration was less extensive in Tnfr1$^{-/-}$ HCCs (FIG. 7A). Real-time PCR and IHC analysis indicated that macrophage and B cell markers were significantly increased by HFD in WT but not in Tnfr1$^{-/-}$ HCCs (FIGS. 7B and 7C). In addition, mRNAs for numerous inflammatory cytokines, chemokines, and growth factors were upregulated by HFD in WT but not in Tnfr1$^{-/-}$ HCCs (FIG. 14). IF analysis confirmed that expression of CCL7, which attracts macrophages and monocytes, was increased by HFD in WT but not in Tnfr1$^{-/-}$ HCCs (FIG. 7D). Thus, TNFR1 signaling in HCC cells promotes tumor-associated inflammation, which can account for ERK and STAT3 activation in malignant cells.

Example 8 p62 Accelerates NASH to HCC Progression

Figure 15A:
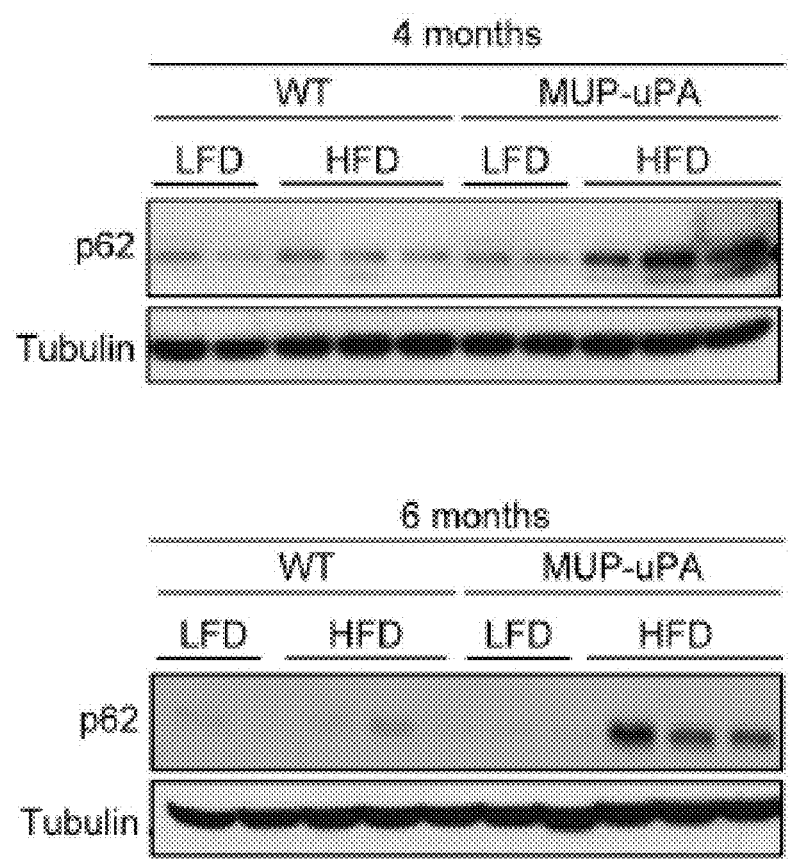
FIGS. 15A-15D are graphical and pictorial diagrams showing that p62 ablation inhibits HCC development but not steatosis in MUP-uPA mice.
Figure 15B:
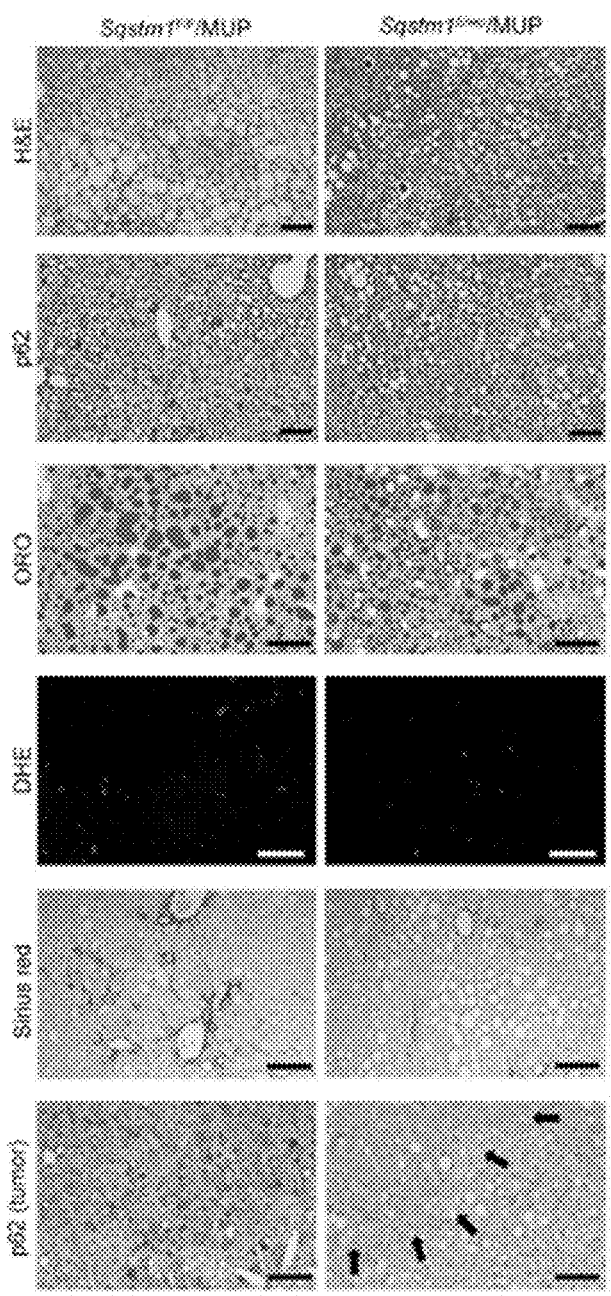
Figure 15C:
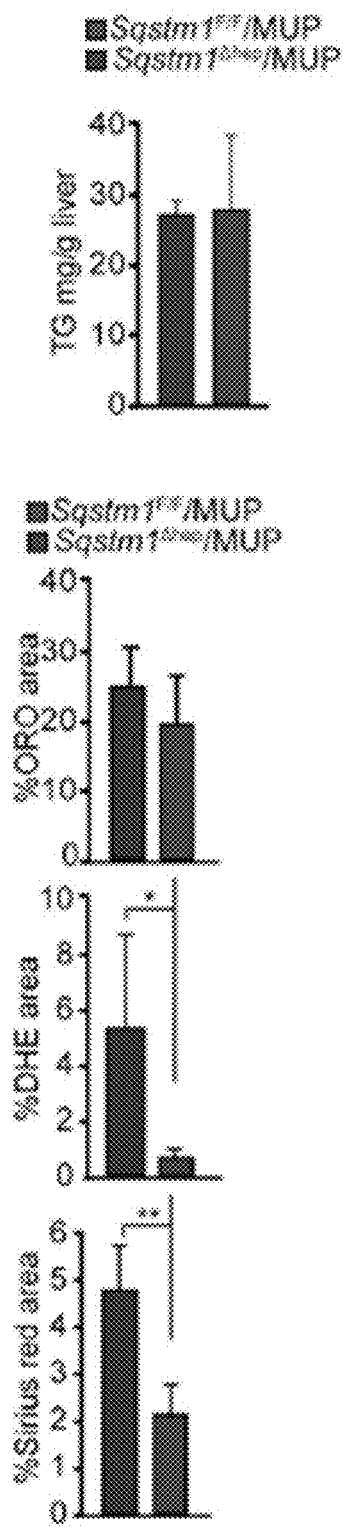
Figure 15D:
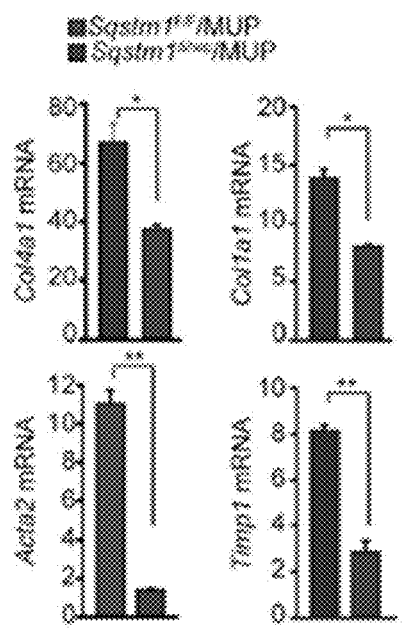
Figure 15E:
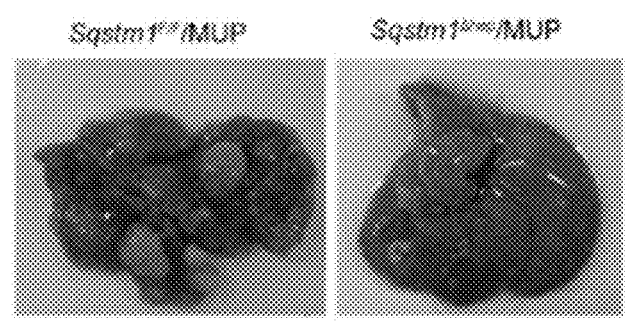
FIG. 15E shows gross liver morphology (upper) and tumor numbers and maximal sizes (lower) in 10-month-old mice kept on HFD. Results are mean±SEM (n=7-11). *p<0.05, p<0.01, *p<0.001.
Figure 15E:
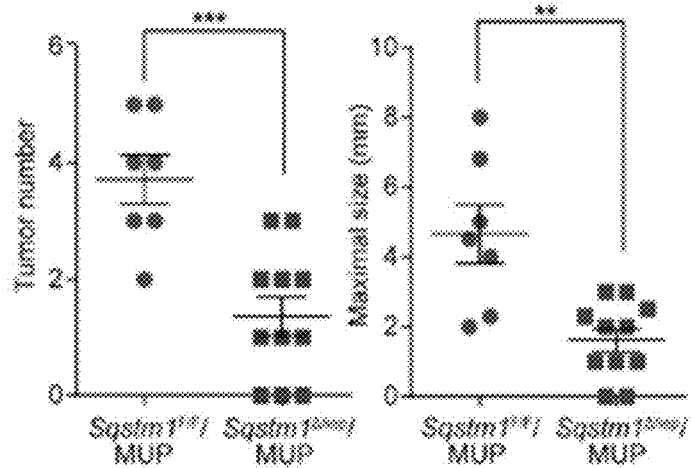

Hypernutrition activates mTORC1 resulting in inhibitory ULK1/2 phosphorylation, reduced autophagic flux, and p62 accumulation. A new mouse model of NASH-driven HCC was therefore developed by feeding MUP-uPA mice with HFD, which induces p62 accumulation in non-tumor liver and HCCs (Nakagawa et al., 2014). Surprisingly, HFD feeding to wild-type (WT) B6 mice, which do not develop NASH or HCC, did not induce p62 accumulation (FIG. 15A). In contrast, HFD induced strong p62 expression in MUP-uPA mice (FIG. 15A), suggesting that p62 accumulation is tightly linked to NASH and HCC development. To probe the pathogenic role of p62, MUP-uPA and Sqstm1$^{\Delta hep}$ (Sqstm1$^{\Delta hep}$/MUP) mice were crossed and male progeny were placed on HFD. Although p62 ablation did not decrease liver lipid droplets or triglycerides, it led to reduced fibrosis and nearly complete absence of cells that accumulate superoxides, which are DHE positive (FIGS. 15B-15D). Notably, p62 ablation substantially suppressed HCC development (FIG. 15E). Both tumor number and maximal size were reduced in Sqstm1$^{\Delta hep}$/MUP mice, and no p62 expression was seen in the remaining tumors (FIG. 15B).

NASH development and HCC progression is also seen in the STZ-HFD model, based on induction of type 1 diabetes (β-cell destruction) with streptozotocin (STZ) followed by HFD feeding. STZ-HFD mice develop HCC, whose histological features were similar to those of HCC in MUP-uPA mice, including p62 accumulation. Although p62 deletion in the STZ-HFD model did not suppress fibrosis, steatosis, or triglyceride accumulation, it strongly suppressed HCC development.

REFERENCES

The following references are incorporated herein by reference in their entireties.

Anderson, et al. (2009). Mitochondrial H2O2 emission and cellular redox state link excess fat intake to insulin resistance in both rodents and humans. J Clin Invest 119, 573-581.

Brunt, E. M. (2001). Nonalcoholic steatohepatitis: definition and pathology. Semin Liver Dis 21, 3-16.

Caldwell, et al. (2010). Hepatocellular ballooning in NASH. J Hepatol 53, 719-723.

Calle, E. E., Teras, L. R., and Thun, M. J. (2005). Obesity and mortality. N Engl J Med 353, 2197-2199.

Chandler, et al. (2015). Vector design influences hepatic genotoxicity after adeno-associated virus gene therapy. J. Clin. Invest. 125, 870-880.

Chen, et al. (2008). Metabolic factors and risk of hepatocellular carcinoma by chronic hepatitis B/C infection: a follow-up study in Taiwan. Gastroenterology 135, 111-121.

Cohen, J. C., Horton, J. D., and Hobbs, H. H. (2011). Human fatty liver disease: old questions and new insights. Science 332, 1519-1523.

Day, C. P., and James, O. F. (1998). Steatohepatitis: a tale of two "hits"? Gastroenterology 114, 842-845.

Denk, et al. (2006). Are the Mallory bodies and intracellular hyaline bodies in neoplastic and non-neoplastic hepatocytes related? J. Pathol. 208, 653-661.

DeZwaan-McCabe, et al. (2013). The stress-regulated transcription factor CHOP promotes hepatic inflammatory gene expression, fibrosis, and oncogenesis. PLoS Genet 9, e1003937.

El-Serag, H. B. (2011). Hepatocellular carcinoma. N Engl J Med 365, 1118-1127.

Farrell, et al. (2012). NASH is an Inflammatory Disorder: Pathogenic, Prognostic and Therapeutic Implications. Gut and liver 6, 149-171.

Goldstein, et al. (2006). Protein sensors for membrane sterols. Cell 124, 35-46.

Haybaeck, et al. (2009). A lymphotoxin-driven pathway to hepatocellular carcinoma. Cancer Cell 16, 295-308.

Hayes, J. D., and McMahon, M. (2006). The double-edged sword of Nrf2: subversion of redox homeostasis during the evolution of cancer. Mol. Cell 21, 732-734.

Hayes, J. D., and McMahon, M. (2009). NRF2 and KEAP1 mutations: permanent activation of an adaptive response in cancer. Trends Biochem. Sci. 34, 176-188.

He, et al. (2013). Identification of liver cancer progenitors whose malignant progression depends on autocrine IL-6 signaling. Cell 155, 384-396.

Holzer, et al. (2011). Saturated fatty acids induce c-Src clustering within membrane subdomains, leading to JNK activation. Cell 147, 173-184.

Hotamisligil, G. S. (2010). Endoplasmic reticulum stress and the inflammatory basis of metabolic disease. Cell 140, 900-917.

Ichimura, et al. (2013). Phosphorylation of p62 activates the Keap1-Nrf2 pathway during selective autophagy. Mol. Cell 51, 618-631.

Inami, et al. (2011). Persistent activation of Nrf2 through p62 in hepatocellular carcinoma cells. J Cell Biol 193, 275-284.

Jain, et al. (2010). p62/SQSTM1 is a target gene for transcription factor NRF2 and creates a positive feedback loop by inducing antioxidant response element-driven gene transcription. J. Biol. Chem. 285, 22576-22591.

Kammoun, et al. (2009). GRP78 expression inhibits insulin and ER stress-induced SREBP-1c activation and reduces hepatic steatosis in mice. J Clin Invest 119, 1201-1215.

Kaposi-Novak, et al. (2009). Central role of c-Myc during malignant conversion in human hepatocarcinogenesis. Cancer Res. 69, 2775-2782.

Komatsu, et al. (2007). Homeostatic levels of p62 control cytoplasmic inclusion body formation in autophagy-deficient mice. Cell 131, 1149-1163.

Komatsu, et al. (2012). p62/SQSTM1/A170: physiology and pathology. Pharmacol. Res. 66, 457-462.

Lee, et al. (2008). Regulation of hepatic lipogenesis by the transcription factor XBP1. Science 320, 1492-1496.

Lee, et al. (2012). Maintenance of metabolic homeostasis by Sestrin2 and Sestrin3. Cell Metab 16, 311-321.

Li, et al. (2013). SQSTM1 is a pathogenic target of 5q copy number gains in kidney cancer. Cancer Cell 24, 738-750.

Maeda, et al. (2005). IKKbeta couples hepatocyte death to cytokine-driven compensatory proliferation that promotes chemical hepatocarcinogenesis. Cell 121, 977-990.

Malhi, H., and Kaufman, R. J. (2011). Endoplasmic reticulum stress in liver disease. J Hepatol 54, 795-809.

Menon, et al. (2012). Chronic activation of mTOR complex 1 is sufficient to cause hepatocellular carcinoma in mice. Sci. Signal. 5, ra24.

Mori, et al. (2009). Critical role for hypothalamic mTOR activity in energy balance. Cell Metab. 9, 362-374.

Muller, et al. (2013). p62 links beta-adrenergic input to mitochondrial function and thermogenesis. J. Clin. Invest. 123, 469-478.

Nakagawa, et al. (2014). ER stress cooperates with hypernutrition to trigger TNF-dependent spontaneous HCC development. Cancer Cell 26, 331-343.

Ota, et al. (2008). Inhibition of apolipoprotein B100 secretion by lipid-induced hepatic endoplasmic reticulum stress in rodents. J Clin Invest 118, 316-332.

Ozcan, et al. (2006). Chemical chaperones reduce ER stress and restore glucose homeostasis in a mouse model of type 2 diabetes. Science 313, 1137-1140.

Park, et al. (2010). Dietary and genetic obesity promote liver inflammation and tumorigenesis by enhancing IL-6 and TNF expression. Cell 140, 197-208.

Puri, et al. (2008). Activation and dysregulation of the unfolded protein response in nonalcoholic fatty liver disease. Gastroenterology 134, 568-576.

Qiu, et al. (2011). Hepatic autophagy mediates endoplasmic reticulum stress-induced degradation of misfolded apolipoprotein B. Hepatology 53, 1515-1525.

Rutkowski, et al. (2008). UPR pathways combine to prevent hepatic steatosis caused by ER stress-mediated suppression of transcriptional master regulators. Dev Cell 15, 829-840.

Sakurai, et al. (2008). Hepatocyte necrosis induced by oxidative stress and IL-1 alpha release mediate carcinogen-induced compensatory proliferation and liver tumorigenesis. Cancer Cell 14, 156-165.

Salomao, et al. (2012). The steatohepatitic variant of hepatocellular carcinoma and its association with underlying steatohepatitis. Hum Pathol 43, 737-746.

Sandgren, et al. (1991). Complete hepatic regeneration after somatic deletion of an albumin-plasminogen activator transgene. Cell 66, 245-256.

Sanz, et al. (2000). The atypical PKC-interacting protein p62 channels NF-kappaB activation by the IL-1-TRAF6 pathway. EMBO J. 19, 1576-1586.

Schramm, et al. (2008). Adalimumab could suppress the activity of non alcoholic steatohepatitis (NASH). Zeitschrift fur Gastroenterologie 46, 1369-1371.

So, et al. (2012). Silencing of lipid metabolism genes through IRE1alpha-mediated mRNA decay lowers plasma lipids in mice. Cell metabolism 16, 487-499.

Soon, et al. (2010). Stress signaling in the methionine-choline-deficient model of murine fatty liver disease. Gastroenterology 139, 1730-1739, 1739 e1731.

Suzuki, et al. (2013). Toward clinical application of the Keap1-Nrf2 pathway. Trends Pharmacol. Sci. 34, 340-346.

Tilg, H., and Moschen, A. R. (2010). Evolution of inflammation in nonalcoholic fatty liver disease: the multiple parallel hits hypothesis. Hepatology 52, 1836-1846.

Toffanin, S., Friedman, S. L., and Llovet, J. M. (2010). Obesity, inflammatory signaling, and hepatocellular carcinoma—an enlarging link. Cancer Cell 17, 115-117.

Umemura, et al. (2014). Liver damage, inflammation, and enhanced tumorigenesis after persistent mTORC1 inhibition. Cell Metab. 20, 133-144.

Valencia, et al. (2014). Metabolic reprogramming of stromal fibroblasts through p62-mTORC1 signaling promotes inflammation and tumorigenesis. Cancer Cell 26, 121-135.

Wang, et al. (2010). Endoplasmic reticulum stress response in cancer: molecular mechanism and therapeutic potential. American journal of translational research 2, 65-74.

Weglarz, et al. (2000). Hepatocyte transplantation into diseased mouse liver. Kinetics of parenchymal repopulation and identification of the proliferative capacity of tetraploid and octaploid hepatocytes. Am J Pathol 157, 1963-1974.

Xu, et al. (2005). Endoplasmic reticulum stress: cell life and death decisions. J Clin Invest 115, 2656-2664.

While the disclosure has been described with reference to the above examples it will be understood that it is capable of further modifications. This application is intended to cover any variations, uses, or adaptations of the disclosure following, in general, the disclosed principles and including such departures from the disclosure as come within known or customary practice within the art to which the disclosure pertains and as may be applied to the essential features hereinbefore set forth. Accordingly, the invention is limited only by the following claims.

What is claimed is:

1. A method of inducing hepatocellular carcinoma (HCC) or HCC-like symptoms in a transgenic mouse comprising transplanting HCC progenitor cells (HcPCs) into a transgenic mouse and subjecting the transgenic mouse to a high fat diet (HFD), wherein the transgenic mouse comprises major urinary protein-urokinase plasminogen activator (MUP-uPA) gene.

2. The method of claim 1, wherein the transgenic mouse exhibits elevated expression or activity of p62, NRF2, mTORC1, or c-Myc, as compared to non-transgenic wild-type control mice.

3. The method of claim 1, wherein the transgenic mouse exhibits increased expression of type 1 collagen al mRNA, as compared to a non-transgenic wild-type control mouse.

4. The method of claim 1, wherein the transgenic mouse exhibits increased hepatocyte ballooning, serum alanine aminotransferase, liver triglycerides (TG) and cholesterol, as compared to a non-transgenic wild-type control mouse.

* * * * *